(12) United States Patent
Marie-Nelly et al.

(10) Patent No.: US 11,423,256 B2
(45) Date of Patent: Aug. 23, 2022

(54) BIOLOGICAL IMAGE TRANSFORMATION USING MACHINE-LEARNING MODELS

(71) Applicant: Insitro, Inc., South San Francisco, CA (US)

(72) Inventors: Herve Marie-Nelly, San Francisco, CA (US); Jeevaa Velayutham, Puchong (MY)

(73) Assignee: Insitro, Inc., South San Francisco, CA (US)

( * ) Notice: Subject to any disclaimer, the term of this patent is extended or adjusted under 35 U.S.C. 154(b) by 0 days.

(21) Appl. No.: 17/480,047

(22) Filed: Sep. 20, 2021

(65) Prior Publication Data
US 2022/0076067 A1    Mar. 10, 2022

Related U.S. Application Data

(63) Continuation of application No. PCT/US2021/049327, filed on Sep. 7, 2021.
(Continued)

(51) Int. Cl.
*G06K 9/62* (2022.01)
*G06T 7/00* (2017.01)
(Continued)

(52) U.S. Cl.
CPC .......... *G06K 9/6256* (2013.01); *G06K 9/628* (2013.01); *G06N 3/0454* (2013.01); *G06N 3/088* (2013.01);
(Continued)

(58) Field of Classification Search
CPC ...... G06K 9/6256; G06K 9/628; G06K 9/258; G06N 3/0454; G06N 3/088; G06T 7/0012;
(Continued)

(56) References Cited

U.S. PATENT DOCUMENTS

2018/0286040 A1*  10/2018  Sashida ............... G06V 10/454
2021/0043331 A1*   2/2021  Ozcan ................. G06K 9/6259
(Continued)

FOREIGN PATENT DOCUMENTS

KR      20190095901 A      8/2019
WO   WO-2007121454 A1 *  10/2007  ............. A61B 5/726

OTHER PUBLICATIONS

Ounkomol et al., "Label-free prediction of three-dimensional fluorescence images from transmitted light microscopy", Nat. Methods, Nov. 2018; 15(11): 917-920, pp. 1-13 (Year: 2018).*
(Continued)

*Primary Examiner* — Nay A Maung
*Assistant Examiner* — Jose M Torres
(74) *Attorney, Agent, or Firm* — Morrison & Foerster LLP

(57) ABSTRACT

Described are systems and methods for training a machine-learning model to generate image of biological samples, and systems and methods for generating enhanced images of biological samples. The method for training a machine-learning model to generate images of biological samples may include obtaining a plurality of training images comprising a training image of a first type, and a training image of a second type. The method may also include generating, based on the training image of the first type, a plurality of wavelet coefficients using the machine-learning model; generating, based on the plurality of wavelet coefficients, a synthetic image of the second type; comparing the synthetic image of the second type with the training image of the second type; and updating the machine-learning model based on the comparison.

28 Claims, 26 Drawing Sheets

Related U.S. Application Data

(60) Provisional application No. 63/143,707, filed on Jan. 29, 2021, provisional application No. 63/075,751, filed on Sep. 8, 2020.

(51) Int. Cl.
| | |
|---|---|
| *G06T 7/10* | (2017.01) |
| *G06N 3/08* | (2006.01) |
| *G06N 3/04* | (2006.01) |
| *A61B 10/00* | (2006.01) |
| *A61B 5/00* | (2006.01) |

(52) U.S. Cl.
CPC ............ *G06T 7/0012* (2013.01); *G06T 7/10* (2017.01); *A61B 5/7267* (2013.01); *A61B 10/00* (2013.01); *G06T 2207/10056* (2013.01); *G06T 2207/10064* (2013.01); *G06T 2207/10152* (2013.01); *G06T 2207/20081* (2013.01); *G06T 2207/20084* (2013.01)

(58) Field of Classification Search
CPC ............ G06T 7/10; G06T 2207/10056; G06T 2207/10064; G06T 2207/10152; G06T 2207/20081; G06T 2207/20084; G06T 5/001; G06T 2207/20064; G06T 2207/30024; A61B 5/7267; A61B 10/00; G06V 10/52; G06V 10/774; G06V 10/80; G06V 10/82; G06V 20/69
See application file for complete search history.

(56) References Cited

U.S. PATENT DOCUMENTS

2021/0304401 A1* 9/2021 Lau ..................... G06T 7/0012
2021/0325308 A1* 10/2021 Kannan ................ G06N 3/0454

OTHER PUBLICATIONS

Christiansen et al., "In silico labeling: Predicting fluorescent labels in unlabeled images", Cell, Apr. 19, 2018, 173(3): 792-803, pp. 1-37 (Year: 2018).*

De Haan et al., "Deep-Learning-Based Image Reconstruction and Enhancement in Optical Microscopy", Proceedings of the IEEE, vol. 108, Issue 1, Jan. 2020, pp. 30-50 (Year: 2020).*

Bernet et al., (2006). "Quantitative imaging of complex samples in spiral phase contrast microscopy," Optics Express, 14(9):3792-3805.

Cooke et al., (2020). "Physics-enhanced machine learning for virtual fluorescence microscopy," available online at <https://arxiv.org/pdf/2004.04306.pdf>, 12 pages.

Fürhapter et al., (2005). "Spiral phase contrast imaging in microscopy," Optics Express, 13(3):689-694.

Gardner et al., (2018). "CellPAINT: Interactive Illustration of Dynamic Mesoscale Cellular Environments," IEEE Comput Graph Appl., 38(6):51-66, 23 pages.

Guo et al., (2019). "Revealing architectural order with quantitative label-free imaging and deep learning," eLide, 9:e55502, 33 pages.

Ham, (2020). "Deep learning accurately stains digital biopsy slides," available online at <https://medicalxpress.com/news/2020-05-deep-accurately-digital-biopsy.html>, 4 pages.

Jesacher et al., (2005). "Shadow effects in spiral phase contrast microscopy," Phys Rev Lett., 94(23):233902, 4 pages.

Jesacher et al., (2007). "Wavefront correction of spatial light modulators using an optical vortex image," Optics Express, 15(9):5801-5808.

Kellman et al., (2015). "Physics-based Learned Design: Optimized Coded-Illumination for Quantitative Phase Imaging," Journal of Latex class files, 14(8):1-9.

Lu et al., (2016). "Quantitative phase imaging and complex field reconstruction by pupil modulation differential phase contrast," Optics Express, 24(22):25345-25361.

Maurer et al., (2008). "Phase contrast microscopy with full numerical aperture illumination," Optics Express, 16(24):19821-19829.

Maurer et al., (2008). "Upgrading a microscope with a spiral phase plate," J Microsc., 230:134-142. Abstract Only.

Maurer et al., (2010). "Depth-of-field-multiplexing in microscopy," Optics Express, 18(3)3023-3034.

McIntyre et al., (2009). "Differential interference contrast imaging using a spatial light modulator," 34(19):2988-2990.

McIntyre et al., (2010). "Quantitative SLM-based differential interference contrast Imaging," Optics Express, 18(13):14063-14078.

Ounkomol et al., (2018). "Label-free prediction of three-dimensional fluorescence images from transmitted-light microscopy," Nature Methods, 15:917-920, 25 pages.

Ouyang et al., (2018). "Deep learning massively accelerates super-resolution localization microscopy," Nature Biotechnology, 36:460-468, 109 pages.

Rivenson et al., (2019). "PhaseStain: the digital staining of label-free quantitative phase microscopy images using deep learning," Light: Science &Applications, 8:23, 11 pages.

Weigert et al., (2018). "Content-aware image restoration: pushing the limits of fluorescence microscopy," Nature Methods, 15:1090-1097, 17 pages.

Invitation to Pay Additional Fees and partial Search Report received for International Patent Application No. PCT/US2021/049327 dated Jan. 12, 2022, 11 pages.

Qu et al., (2019). "Wavelet-based Semi-supervised Adversarial Learning for Synthesizing Realistic 7T from 3T MRI," Med Image Comput Comput Assist Interv., 11767:786-794.

* cited by examiner

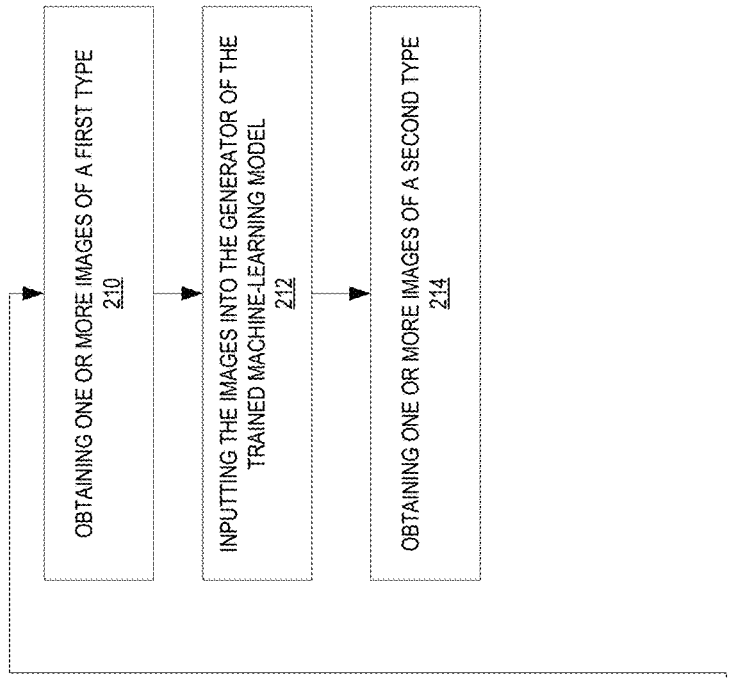
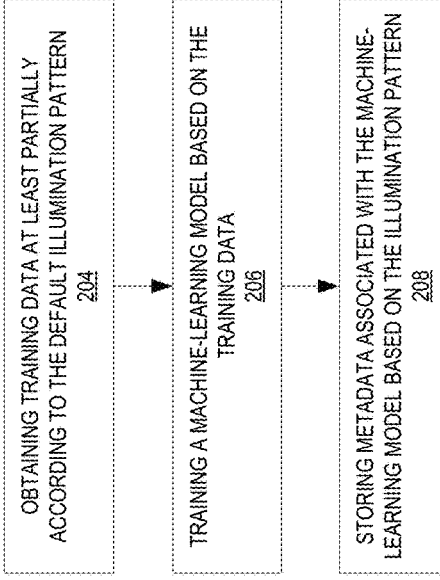
FIG. 2A (Illumination Pattern Not Updated During Training)

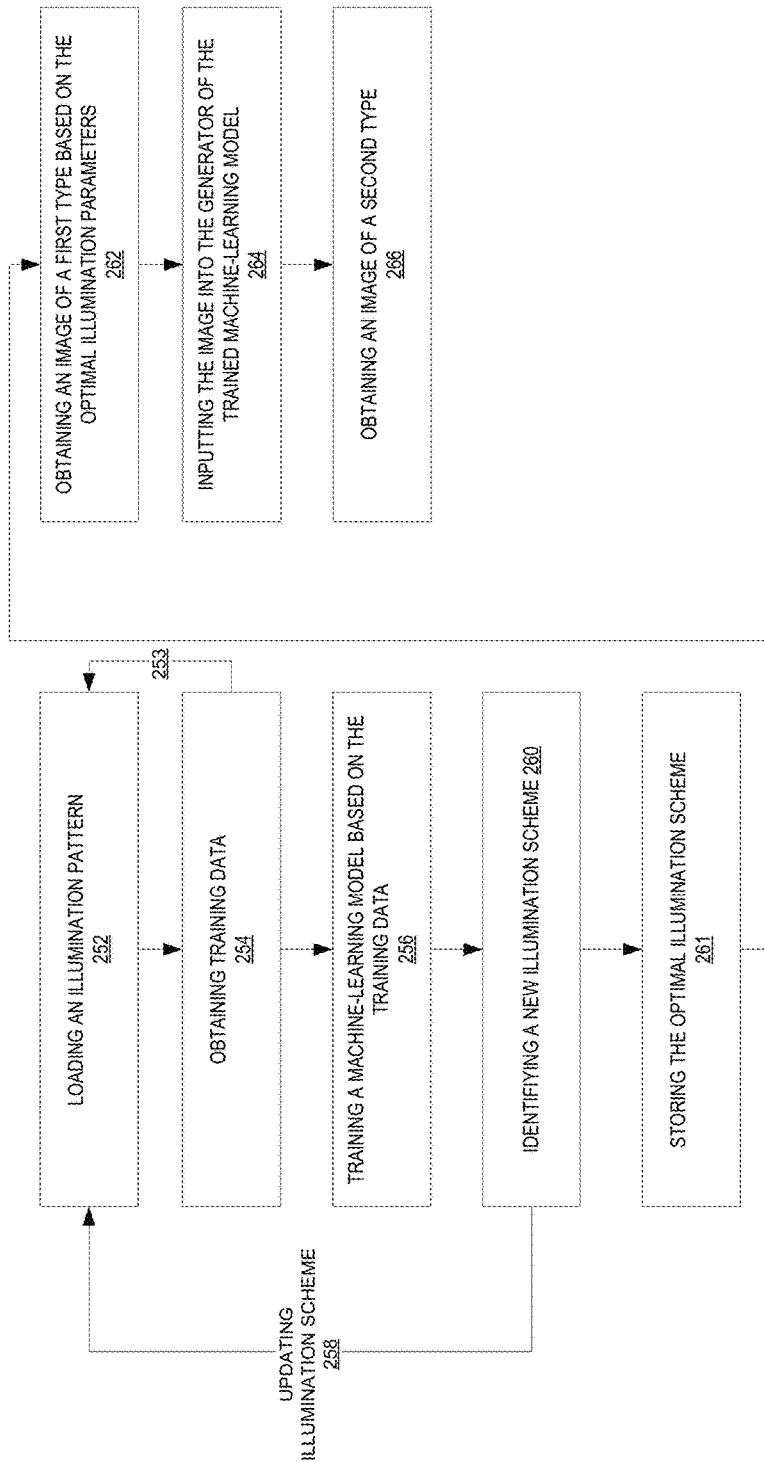
FIG. 2B (Illumination Pattern Updated During Training)

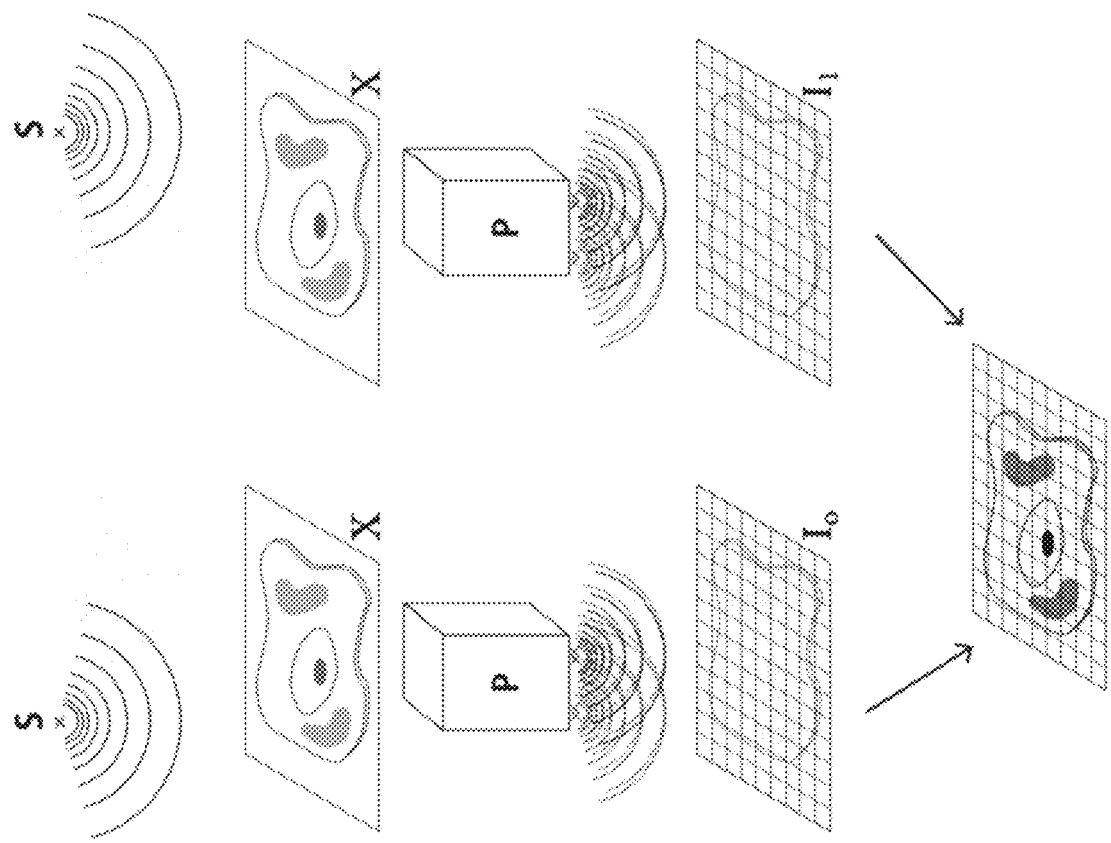

1000

1002
OBTAINING A PLURALITY OF IMAGES OF THE BIOLOGICAL SAMPLE USING A PLURALITY OF CONFIGURATIONS OF A SLM OF AN OPTICAL SYSTEM

1004
INPUTTING THE PLURALITY OF IMAGES OF THE BIOLOGICAL SAMPLE INTO A TRAINED MACHINE-LEARNING MODEL TO OBTAIN ONE OR MORE OUTPUTS

1100

1102
OBTAINING A PLURALITY OF IMAGES OF A BIOLOGICAL SAMPLE USING A PLURALITY OF CONFIGURATIONS OF AN SLM OF AN OPTICAL SYSTEM

1104
TRAINING THE MACHINE-LEARNING MODEL USING THE PLURALITY OF IMAGES

1106
(A) TRAINING THE MACHINE-LEARNING MODEL USING A FIRST IMAGE, WHEREIN THE FIRST IMAGE IS OBTAINED USING A FIRST CONFIGURATION OF THE SLM OF THE OPTICAL SYSTEM;

1108
(B) EVALUATING THE TRAINED MACHINE-LEARNING MODEL

1110
(C) BASED ON THE EVALUATION, IDENTIFYING A SECOND CONFIGURATION OF THE SLM

1112
(D) TRAINING THE MACHINE-LEARNING MODEL USING A SECOND IMAGE, WHEREIN THE SECOND IMAGE IS OBTAINED USING THE SECOND CONFIGURATION OF THE SLM OF THE OPTICAL SYSTEM

FIG. 11

Batch 1
Batch 2
Batch 3

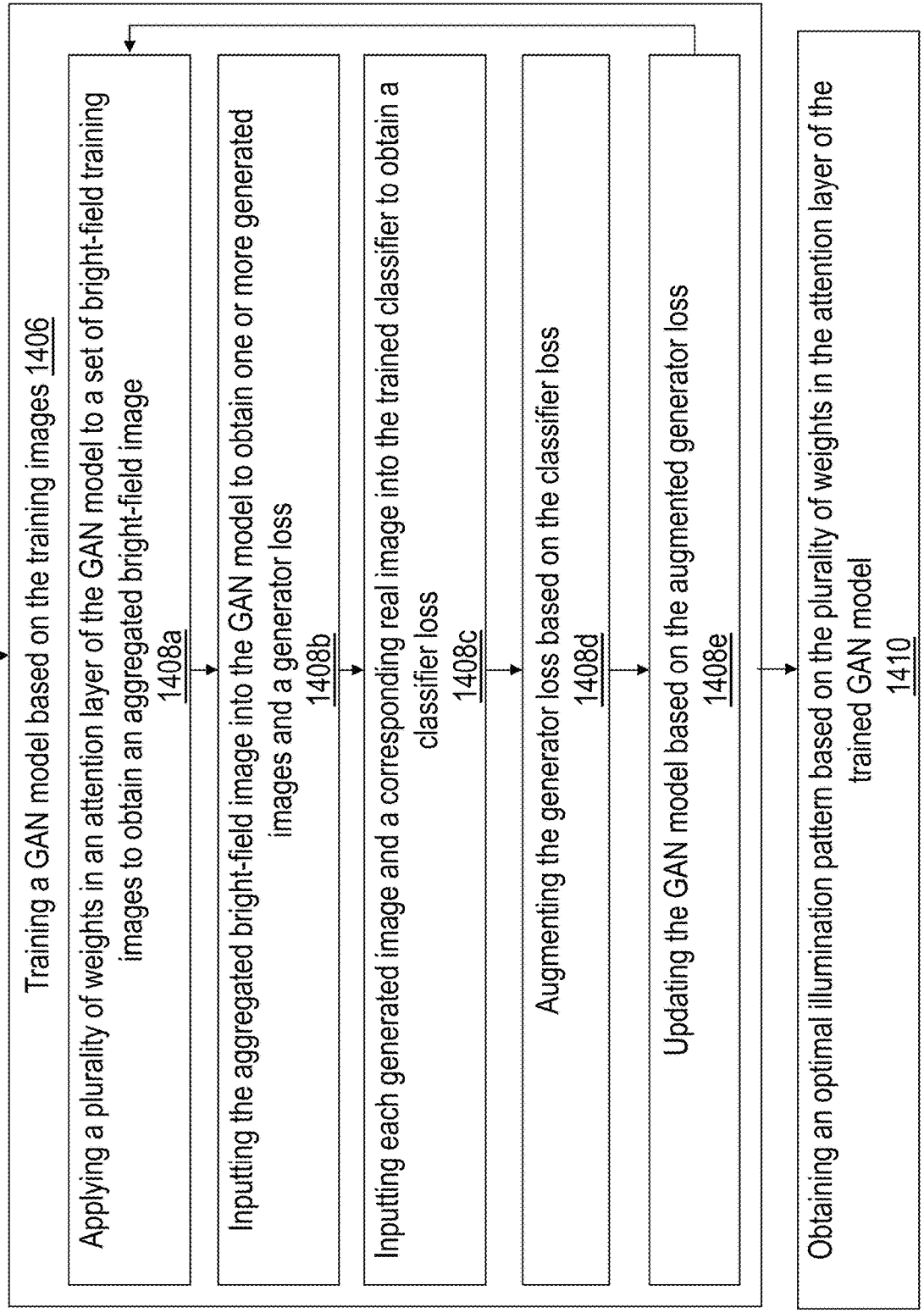

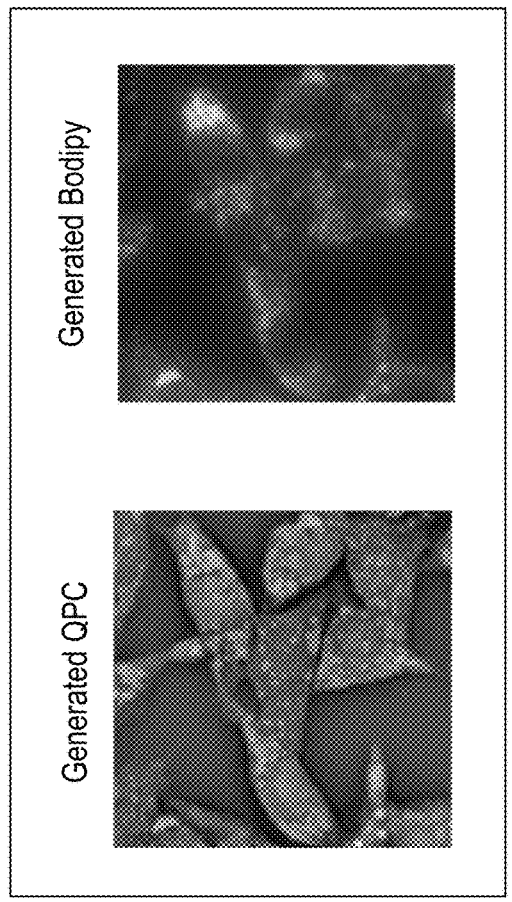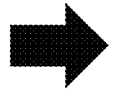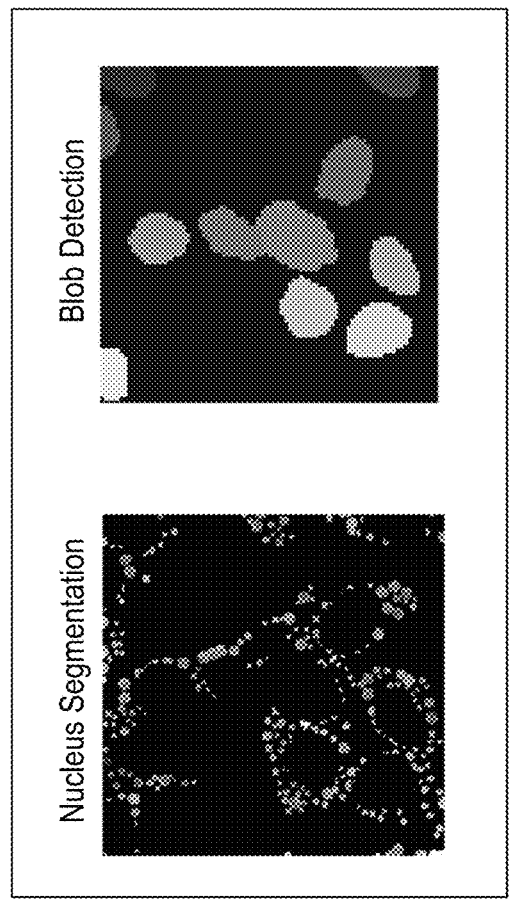
FIG. 16A
FIG. 16B

BIOLOGICAL IMAGE TRANSFORMATION USING MACHINE-LEARNING MODELS

CROSS-REFERENCE TO RELATED APPLICATIONS

This application is a continuation application of International Application No. PCT/US2021/049327, filed Sep. 7, 2021, which claims priority to U.S. Provisional Application No. 63/075,751, filed Sep. 8, 2020, and U.S. Provisional Application No. 63/143,707, filed Jan. 29, 2021, the contents of which are incorporated by reference herein in their entirety.

FIELD OF THE INVENTION

The present disclosure relates generally to machine-learning techniques, and more specifically to low-cost, machine-learning-based generation of image data at scale. The generated image data (e.g., image data of biological samples) can provide sufficient richness and depth optimized for downstream processing (e.g., phenotyping). Some embodiments of the system comprise a programmable spatial light modulator ("SLM") to produce data optimized for downstream processing (e.g., phenotyping) at a high speed without mechanical modifications to the system. Some embodiments of the system comprise a machine-learning model with an attention layer comprising a plurality of weights corresponding to a plurality of illumination settings (e.g., different illumination emitters of an illumination source) for identifying an optimal illumination pattern for capturing the image data. Some embodiments of the system comprise techniques for evaluating candidate treatments with respect to a disease of interest.

BACKGROUND

Bright-field images of biological samples can be obtained at scale and at low cost due to inexpensive equipment, ease of clinical deployment, and low processing and storage resource requirements for captured images. Obtaining bright-field images is generally non-invasive and involves low photo-toxicity. However, low-contrast images lack rich visual details, thus making them unsuitable for many downstream analyses (e.g., phenotypic exploration of microscopic samples). In comparison, other image modalities (e.g., fluorescence images) can provide rich visual information of the captured samples. However, obtaining fluorescence images requires additional equipment and materials and can be time-consuming and computing resource intensive. Thus, fluorescence images can be difficult to obtain at scale and in a low-cost manner.

Transforming bright-field images of biological samples into enhanced, high-quality images can be difficult for a number of reasons. First, the bright-field images suffer from the inherent class imbalance problem (i.e., abundant low frequency signals but fewer high frequency signals). Further, the overall geometry of the bright-field images needs to be extracted and maintained through the transformation. Furthermore, many factors such as the illumination pattern under which the bright-field images are taken can impact the effectiveness of the transformation. Further still, the robustness of the transformation in supporting downstream analyses needs to be quantified and validated.

BRIEF SUMMARY

Described are systems and methods for training machine-learning models to generate images of biological samples. Also described are systems and methods for generating enhanced images of biological samples. The systems and methods can be used, for example to obtain images of a first type, for example, a bright-field image type. The obtained images of the first image type can then be used by the systems and methods to generate a synthetic image of a second type, for example, a fluorescence image.

In some embodiments, a method for training a machine-learning model to generate images of biological samples, comprises obtaining a plurality of training images. The plurality of images comprises a training image of a first type, and a training image of a second type. The method also comprises generating, based on the training image of the first type, a plurality of wavelet coefficients using the machine-learning model; generating, based on the plurality of wavelet coefficients, a synthetic image of the second type; comparing the synthetic image of the second type with the training image of the second type; and updating the machine-learning model based on the comparison.

In some embodiment, a method for generating enhanced images of biological samples, comprises obtaining, using a microscope, an image of a biological sample; and generating, based on the image, an enhanced image of the biological sample using a machine-learning model. The machine-learning model may be trained by: obtaining a plurality of training images comprising a training image of a first type, and a training image of a second type; generating, based on the training image of the first type, a plurality of wavelet coefficients using the machine-learning model; generating, based on the plurality of wavelet coefficients, a synthetic image of the second type; comparing the synthetic image of the second type with the training image of the second type; and updating the machine-learning model based on the comparison.

In some embodiments, a system for training a machine-learning model to generate images of biological samples, comprises: a computing system comprising one or more processors, and one or more memories storing a machine-learning model, wherein the computing system is configured to receive a plurality of training images of a first type and one a training image of a second type. The computing system may be configured to: generate, based on the training images of the first type, a plurality of wavelet coefficients using the machine-learning model; generate, based on the plurality of wavelet coefficients, a synthetic image of the second type; compare the synthetic image of the second type with the training image of the second type; and update the machine-learning model based on the comparison.

In some embodiments, a system for generating enhanced images of biological samples, comprises: a computing system comprising one or more processors, and one or more memories storing a machine-learning model. The computing system may be configured to receive an image of a biological sample obtained from a microscope and generate, based on the image, an enhanced image of the biological sample using a machine-learning model. The machine-learning model may be been trained by: obtaining a plurality of training images comprising a training image of a first type, and a training image of a second type; generating, based on the training image of the first type, a plurality of wavelet coefficients using the machine-learning model; generating, based on the plurality of wavelet coefficients, a synthetic image of the second type; comparing the synthetic image of the second type with the training image of the second type; and updating the machine-learning model based on the comparison.

An exemplary method for training a machine-learning model to generate images of biological samples comprises: obtaining a plurality of training images comprising: a training image of a first type, and a training image of a second type; generating, based on the training image of the first type, a plurality of wavelet coefficients using the machine-learning model; generating, based on the plurality of wavelet coefficients, a synthetic image of the second type; comparing the synthetic image of the second type with the training image of the second type; and updating the machine-learning model based on the comparison.

In some embodiments, the training image of the first type is a bright-field image of a biological sample.

In some embodiments, the training image of the second type is a fluorescence image of the biological sample.

In some embodiments, the machine-learning model comprises a generator and a discriminator.

In some embodiments, the machine-learning model comprises a conditional GAN model.

In some embodiments, the generator comprises a plurality of neural networks corresponding to a plurality of frequency groups.

In some embodiments, each neural network of the plurality of neural networks is configured to generate wavelet coefficients for a respective frequency group.

In some embodiments, the plurality of neural networks comprises a plurality of U-Net neural networks.

In some embodiments, the discriminator is a PatchGAN neural network.

In some embodiments, the method further comprises: generating, based on the training image of the first type, an image of a third type.

In some embodiments, the image of the third type is a phase shift image.

In some embodiments, the method further comprises: generating, based on the training image of the first type, an image of a fourth type.

In some embodiments, the image of the fourth type comprises segmentation data.

In some embodiments, the training image of the first type is captured using a microscope according to a first illumination scheme.

In some embodiments, the first illumination scheme comprises one or more illumination patterns.

In some embodiments, the training image of the first type is part of a bright-field image array.

In some embodiments, the plurality of training images is a first plurality of training images, the method further comprising: based on the comparison, identifying a second illumination scheme; obtaining a second plurality of training images comprising one or more images of the first type, wherein the one or more images of the first type are obtained based on the second illumination scheme; training the machine-learning model based on the second plurality of training images.

In some embodiments, the method further comprises obtaining, using a microscope, a plurality of images of the first type; and generating, based on the obtained plurality of images, a plurality of synthetic images of the second type using the machine-learning model.

In some embodiments, the method further comprises training a classifier based on the plurality of synthetic images of the second type.

In some embodiments, the microscope is a first microscope, wherein the classifier is a first classifier, further comprising: obtaining, using a second microscope, a plurality of images of the second type; training a second classifier based on the plurality of images of the second type; comparing performance of the first classifier and the second classifier.

In some embodiments, the second microscope is a fluorescence microscope.

An exemplary method for generating enhanced images of biological samples comprises: obtaining, using a microscope, an image of a biological sample; and generating, based on the image, an enhanced image of the biological sample using a machine-learning model, wherein the machine-learning model has been trained by: obtaining a plurality of training images comprising a training image of a first type, and a training image of a second type; generating, based on the training image of the first type, a plurality of wavelet coefficients using the machine-learning model; generating, based on the plurality of wavelet coefficients, a synthetic image of the second type; comparing the synthetic image of the second type with the training image of the second type; and updating the machine-learning model based on the comparison.

In some embodiments, the training image of the first type is a bright-field image of a biological sample.

In some embodiments, the training image of the second type is a fluorescence image of the biological sample.

In some embodiments, the machine-learning model comprises a generator and a discriminator.

In some embodiments, the machine-learning model comprises a conditional GAN model.

In some embodiments, the generator comprises a plurality of neural networks corresponding to a plurality of frequency groups.

In some embodiments, each neural network of the plurality of neural networks is configured to generate wavelet coefficients for a respective frequency group.

In some embodiments, the plurality of neural networks comprises a plurality of U-Net neural networks.

In some embodiments, the discriminator is a PatchGAN neural network.

In some embodiments, the method further comprises: generating, based on the training image of the first type, an image of a third type.

In some embodiments, the image of the third type is a phase shift image.

In some embodiments, the method further comprises: generating, based on the training image of the first type, an image of a fourth type.

In some embodiments, the image of the fourth type comprises segmentation data.

In some embodiments, the training image of the first type is captured using a microscope according to a first illumination scheme.

In some embodiments, the first illumination scheme comprises one or more illumination patterns.

In some embodiments, the training image of the first type is part of a bright-field image array.

In some embodiments, the plurality of training images is a first plurality of training images, the method further comprising: based on the comparison, identifying a second illumination scheme; obtaining a second plurality of training images comprising one or more images of the first type, wherein the one or more images of the first type are obtained based on the second illumination scheme; training the machine-learning model based on the second plurality of training images.

In some embodiments, the method further comprises obtaining, using a microscope, a plurality of images of the first type; and generating, based on the obtained plurality of images, a plurality of synthetic images of the second type using the machine-learning model.

In some embodiments, the method further comprises: training a classifier based on the plurality of synthetic images of the second type.

In some embodiments, the microscope is a first microscope, wherein the classifier is a first classifier, further comprising: obtaining, using a second microscope, a plurality of images of the second type; training a second classifier based on the plurality of images of the second type; comparing performance of the first classifier and the second classifier.

In some embodiments, the second microscope is a fluorescence microscope.

An exemplary system for training a machine-learning model to generate images of biological samples comprises: a computing system comprising one or more processors, and one or more memories storing a machine-learning model, wherein the computing system is configured to receive a plurality of training images of a first type and one a training image of a second type, and wherein the computing system is configured to generate, based on the training images of the first type, a plurality of wavelet coefficients using the machine-learning model; generate, based on the plurality of wavelet coefficients, a synthetic image of the second type; compare the synthetic image of the second type with the training image of the second type; and update the machine-learning model based on the comparison.

In some embodiments, the training image of the first type is a bright-field image of a biological sample.

In some embodiments, the training image of the second type is a fluorescence image of the biological sample.

In some embodiments, the machine-learning model comprises a generator and a discriminator.

In some embodiments, the machine-learning model comprises a conditional GAN model.

In some embodiments, the generator comprises a plurality of neural networks corresponding to a plurality of frequency groups.

In some embodiments, each neural network of the plurality of neural networks is configured to generate wavelet coefficients for a respective frequency group.

In some embodiments, the plurality of neural networks comprises a plurality of U-Net neural networks.

In some embodiments, the discriminator is a PatchGAN neural network.

In some embodiments, the computing system is further configured to: generate, based on the training image of the first type, an image of a third type.

In some embodiments, the image of the third type is a phase shift image.

In some embodiments, the computing system is further configured to: generate, based on the training image of the first type, an image of a fourth type.

In some embodiments, the image of the fourth type comprises segmentation data.

In some embodiments, the training image of the first type is captured using a microscope according to a first illumination scheme.

In some embodiments, the first illumination scheme comprises one or more illumination patterns.

In some embodiments, the training image of the first type is part of a bright-field image array.

In some embodiments, the plurality of training images is a first plurality of training images, and wherein the computing system is further configured to: based on the comparison, identify a second illumination scheme; obtain a second plurality of training images comprising one or more images of the first type, wherein the one or more images of the first type are obtained based on the second illumination scheme; train the machine-learning model based on the second plurality of training images.

In some embodiments, the computing system is further configured to: obtain, using a microscope, a plurality of images of the first type; and generate, based on the obtained plurality of images, a plurality of synthetic images of the second type using the machine-learning model.

In some embodiments, the computing system is further configured to: train a classifier based on the plurality of synthetic images of the second type.

In some embodiments, the microscope is a first microscope, wherein the classifier is a first classifier, wherein the computing system is further configured to: obtain, using a second microscope, a plurality of images of the second type; train a second classifier based on the plurality of images of the second type; compare performance of the first classifier and the second classifier.

In some embodiments, the second microscope is a fluorescence microscope.

An exemplary system for generating enhanced images of biological samples comprises: a computing system comprising one or more processors, and one or more memories storing a machine-learning model, wherein the computing system is configured to receive an image of a biological sample obtained from a microscope and generate, based on the image, an enhanced image of the biological sample using a machine-learning model, wherein the machine-learning model has been trained by: obtaining a plurality of training images comprising a training image of a first type, and a training image of a second type; generating, based on the training image of the first type, a plurality of wavelet coefficients using the machine-learning model; generating, based on the plurality of wavelet coefficients, a synthetic image of the second type; comparing the synthetic image of the second type with the training image of the second type; and updating the machine-learning model based on the comparison.

In some embodiments, the training image of the first type is a bright-field image of a biological sample.

In some embodiments, the training image of the second type is a fluorescence image of the biological sample.

In some embodiments, the machine-learning model comprises a generator and a discriminator.

In some embodiments, the machine-learning model comprises a conditional GAN model.

In some embodiments, the generator comprises a plurality of neural networks corresponding to a plurality of frequency groups.

In some embodiments, each neural network of the plurality of neural networks is configured to generate wavelet coefficients for a respective frequency group.

In some embodiments, the plurality of neural networks comprises a plurality of U-Net neural networks.

In some embodiments, the discriminator is a PatchGAN neural network.

In some embodiments, the machine learning model is further trained by generating, based on the training image of the first type, an image of a third type.

In some embodiments, the image of the third type is a phase shift image.

In some embodiments, the machine-learning model has been trained by: generating, based on the training image of the first type, an image of a fourth type.

In some embodiments, the image of the fourth type comprises segmentation data.

In some embodiments, the training image of the first type is captured using a microscope according to a first illumination scheme.

In some embodiments, the first illumination scheme comprises one or more illumination patterns.

In some embodiments, the training image of the first type is part of a bright-field image array.

In some embodiments, the plurality of training images is a first plurality of training images, wherein the machine-learning model has been trained by: based on the comparison, identifying a second illumination scheme; obtaining a second plurality of training images comprising one or more images of the first type, wherein the one or more images of the first type are obtained based on the second illumination scheme; training the machine-learning model based on the second plurality of training images.

In some embodiments, the machine-learning model has been trained by: obtaining, using a microscope, a plurality of images of the first type; and generating, based on the obtained plurality of images, a plurality of synthetic images of the second type using the machine-learning model.

In some embodiments, the machine-learning model has been trained by: training a classifier based on the plurality of synthetic images of the second type.

In some embodiments, the microscope is a first microscope, wherein the classifier is a first classifier, wherein the machine-learning model has been trained by: obtaining, using a second microscope, a plurality of images of the second type; training a second classifier based on the plurality of images of the second type; comparing performance of the first classifier and the second classifier.

In some embodiments, the second microscope is a fluorescence microscope.

An exemplary method of processing images of a biological sample to obtain one or more output images comprises: obtaining a plurality of images of the biological sample using a plurality of configurations of a SLM of an optical system, wherein the SLM is located in an optical path between the biological sample and an image recording device; and inputting the plurality of images of the biological sample into a trained machine-learning model to obtain the one or more outputs images.

In some embodiments, at least one configuration of the plurality of configurations of the SLM is to generate one or more optical aberrations.

In some embodiments, generating one or more optical aberrations comprises a spherical aberration, astigmatism, defocus, distortion, tilt, or any combination thereof.

In some embodiments, at least one configuration of the plurality of configurations of the SLM is to enhance one or more features.

In some embodiments, the one or more features comprise a cell border, an actin filament, nuclear shape, cytoplasm segmentation, or any combination thereof.

In some embodiments, at least one configuration of the plurality of configurations of the SLM is to reduce optical aberrations.

In some embodiments, the plurality of SLM configurations is to obtain images of the biological sample at different depths.

In some embodiments, the machine-learning model is configured to generate, based on an image of a first type, an image of a second type.

In some embodiments, the first type of images are bright-field images.

In some embodiments, the second type of images are fluorescence images.

In some embodiments, the second type of images are enhanced versions of the first type of images.

In some embodiments, the machine-learning model is a GAN model or a self-supervised model.

In some embodiments, the plurality of images are obtained using a plurality of configurations of a light source of the optical system.

In some embodiments, the light source is a LED array of the optical system.

In some embodiments, at least one configuration of the plurality of SLM configurations is obtained by: training the machine-learning model; evaluating the trained machine-learning model; and identifying the at least one configuration based on the evaluation.

In some embodiments, the trained machine-learning model is configured to receive an input image and output an enhanced version of the input image.

In some embodiments, the enhanced version of the input image comprises one or more enhanced cellular phenotypes.

An exemplary electronic device for processing images of a biological sample to obtain one or more output images comprises: one or more processors; a memory; and one or more programs, wherein the one or more programs are stored in the memory and configured to be executed by the one or more processors, the one or more programs including instructions for: obtaining a plurality of images of the biological sample using a plurality of configurations of a SLM of an optical system, wherein the SLM is located in an optical path between the biological sample and an image recording device; and inputting the plurality of images of the biological sample into a trained machine-learning model to obtain the one or more output images.

An exemplary non-transitory computer-readable storage medium stores one or more programs for processing images of a biological sample to obtain one or more output images, the one or more programs comprising instructions, which when executed by one or more processors of an electronic device, cause the electronic device to: obtain a plurality of images of the biological sample using a plurality of configurations of a SLM of an optical system, wherein the SLM is located in an optical path between the biological sample and an image recording device; and input the plurality of images of the biological sample into a trained machine-learning model to obtain the one or more output images.

An exemplary method of classifying images of a biological sample comprises: obtaining a plurality of images of the biological sample using a plurality of configurations of an SLM of an optical system, wherein the SLM is located in an optical path between the biological sample and an image recording device; and inputting the plurality of images of the biological sample into a trained machine-learning model to obtain one or more classification outputs.

In some embodiments, at least one configuration of the plurality of configurations of the SLM is to generate one or more optical aberrations.

In some embodiments, generating one or more optical aberrations comprises a spherical aberration, astigmatism, defocus, distortion, tilt, or any combination thereof.

In some embodiments, at least one configuration of the plurality of configurations of the SLM is to enhance one or more features.

In some embodiments, the one or more features comprise a cell border, an actin filament, nuclear shape, cytoplasm segmentation, or any combination thereof.

In some embodiments, at least one configuration of the plurality of configurations of the SLM is to reduce optical aberrations.

In some embodiments, the plurality of SLM configurations is to obtain images of the biological sample at different depths.

In some embodiments, the plurality of images are obtained using a plurality of configurations of a light source of the optical system.

In some embodiments, the light source is a LED array of the optical system.

In some embodiments, at least one configuration of the plurality of SLM configurations is obtained by: training the machine-learning model; evaluating the trained machine-learning model; and identifying the at least one configuration based on the evaluation.

In some embodiments, the trained machine-learning model is configured to receive an input image and detect one or more pre-defined objects in the input image.

In some embodiments, the pre-defined objects include a diseased tissue.

An exemplary electronic device for classifying images of a biological sample comprises: one or more processors; a memory; and one or more programs, wherein the one or more programs are stored in the memory and configured to be executed by the one or more processors, the one or more programs including instructions for: obtaining a plurality of images of the biological sample using a plurality of configurations of an SLM of an optical system, wherein the SLM is located in an optical path between the biological sample and an image recording device; and inputting the plurality of images of the biological sample into a trained machine-learning model to obtain one or more classification outputs.

An exemplary non-transitory computer-readable storage medium stores one or more programs for classifying images of a biological sample, the one or more programs comprising instructions, which when executed by one or more processors of an electronic device, cause the electronic device to: obtain a plurality of images of the biological sample using a plurality of configurations of an SLM of an optical system, wherein the SLM is located in an optical path between the biological sample and an image recording device; and input the plurality of images of the biological sample into a trained machine-learning model to obtain one or more classification outputs.

An exemplary method for training a machine-learning model comprises: obtaining a plurality of images of a biological sample using a plurality of configurations of an SLM of an optical system, wherein the SLM is located in an optical path between the biological sample and an image recording device; and training the machine-learning model using the plurality of images.

In some embodiments, at least one configuration of the plurality of configurations of the SLM is to generate one or more optical aberrations.

In some embodiments, generating one or more optical aberrations comprises a spherical aberration, astigmatism, defocus, distortion, tilt, or any combination thereof.

In some embodiments, at least one configuration of the plurality of configurations of the SLM is to enhance one or more features.

In some embodiments, the one or more features comprise a cell border, an actin filament, nuclear shape, cytoplasm segmentation, or any combination thereof.

In some embodiments, at least one configuration of the plurality of configurations of the SLM is to reduce optical aberrations.

In some embodiments, at least one configuration of the plurality of configurations of the SLM is to obtain images of the biological sample at different depths.

In some embodiments, the machine-learning model is configured to generate, based on an image of a first type, an image of a second type.

In some embodiments, the first type of images are bright-field images.

In some embodiments, the second type of images are fluorescence images.

In some embodiments, the machine-learning model is a GAN model or a self-supervised model.

In some embodiments, the machine-learning model is a classification model.

In some embodiments, the plurality of images are obtained using a plurality of configurations of a light source of the optical system.

In some embodiments, the light source is a LED array of the optical system.

In some embodiments, training the machine-learning model comprises: (a) training the machine-learning model using a first image, wherein the first image is obtained using a first configuration of the SLM of the optical system; (b) evaluating the trained machine-learning model; (c) based on the evaluation, identifying a second configuration of the SLM; and (d) training the machine-learning model using a second image, wherein the second image is obtained using the second configuration of the SLM of the optical system.

In some embodiments, the evaluation is based on a loss function of the machine-learning model.

In some embodiments, the method further comprises: repeating steps (a)-(d) until a threshold is met.

In some embodiments, the threshold is indicative of convergence of the training.

In some embodiments, the trained machine-learning model is configured to receive an input image and output an enhanced version of the input image.

In some embodiments, the enhanced version of the input image comprises one or more enhanced cellular phenotypes.

In some embodiments, the trained machine-learning model is configured to receive an input image and detect one or more pre-defined objects in the input image.

In some embodiments, the pre-defined objects include a diseased tissue.

An exemplary electronic device for training a machine-learning model comprises: one or more processors; a memory; and one or more programs, wherein the one or more programs are stored in the memory and configured to be executed by the one or more processors, the one or more programs including instructions for: obtaining a plurality of images of a biological sample using a plurality of configurations of an SLM of an optical system, wherein the SLM is located in an optical path between the biological sample and an image recording device; and training the machine-learning model using the plurality of images.

An exemplary non-transitory computer-readable storage medium stores one or more programs for training a machine-learning model, the one or more programs comprising instructions, which when executed by one or more processors of an electronic device, cause the electronic device to: obtain a plurality of images of a biological sample using a plurality of configurations of an SLM of an optical system, wherein the SLM is located in an optical path between the biological sample and an image recording device; and train the machine-learning model using the plurality of images.

An exemplary method of generating enhanced images of biological samples comprises: obtaining, using a microscope, an image of a biological sample illuminated using an illumination pattern of an illumination source, wherein the illumination pattern is determined by: training a classification model configured to receive an input image and output a classification result, training, using the trained classification model, a machine-learning model having an plurality of weights corresponding to a plurality of illumination settings, and identifying the illumination pattern based on the plurality of weights of the trained machine-learning model; and generating an enhanced image of the biological sample by inputting the obtained image of the biological sample into the trained machine-learning model.

In some embodiments, the obtained image is a bright-field image.

In some embodiments, the enhanced image is a fluorescence image, a phase image, or a combination thereof.

In some embodiments, the illumination source comprises an array of illumination emitters.

In some embodiments, the illumination source is a LED array.

In some embodiments, the illumination pattern indicates whether each illumination emitter is turned on or off and the intensity of each illumination emitter.

In some embodiments, each illumination setting of the plurality of illumination settings corresponds to a respective illumination emitter of the illumination source; and wherein each weight corresponds to an intensity of the respective illumination emitter.

In some embodiments, the classification model is configured to receive an input phase image or an input fluorescence image and output a classification result indicative of one class out of a plurality of pre-defined classes.

In some embodiments, the plurality of pre-defined classes comprises a healthy class and a diseased class.

In some embodiments, the machine-learning model is a GAN model comprising an attention layer comprising the plurality of weights, a discriminator, and a generator.

In some embodiments, the machine-learning model is a conditional GAN model.

In some embodiments, the generator comprises a plurality of neural networks corresponding to a plurality of frequency groups.

In some embodiments, each neural network of the plurality of neural networks is configured to generate wavelet coefficients for a respective frequency group.

In some embodiments, the plurality of neural networks comprises a plurality of U-Net neural networks.

In some embodiments, the discriminator is a PatchGAN neural network.

In some embodiments, training, using the trained classification model, the machine-learning model comprises: applying the plurality of weights to a plurality of bright-field training images; aggregating the plurality of weighted bright-field training images into an aggregated bright-field image; inputting the aggregated bright-field training image into the machine-learning model to obtain an enhanced training image and a generator loss; inputting the enhanced training image into the trained classifier to obtain a classifier loss; augmenting the generator loss based on the classifier loss; and updating the plurality of weights based on the augmented generator loss.

In some embodiments, the method further comprises: classifying the enhanced image using the trained classifier.

In some embodiments, the method further comprises: displaying the enhanced image.

An exemplary system for generating enhanced images of biological samples comprises: one or more processors; a memory; and one or more programs, wherein the one or more programs are stored in the memory and configured to be executed by the one or more processors, the one or more programs including instructions for: obtaining, using a microscope, an image of a biological sample illuminated using an illumination pattern of an illumination source, wherein the illumination pattern is determined by: training a classification model configured to receive an input image and output a classification result, training, using the trained classification model, a machine-learning model having an plurality of weights corresponding to a plurality of illumination settings, and identifying the illumination pattern based on the plurality of weights of the trained machine-learning model; and generating an enhanced image of the biological sample by inputting the obtained image of the biological sample into the trained machine-learning model.

An exemplary non-transitory computer-readable storage medium stores one or more programs for generating enhanced images of biological samples, the one or more programs comprising instructions, which when executed by one or more processors of an electronic device, cause the electronic device to: obtain, using a microscope, an image of a biological sample illuminated using an illumination pattern of an illumination source, wherein the illumination pattern is determined by: training a classification model configured to receive an input image and output a classification result, training, using the trained classification model, a machine-learning model having an plurality of weights corresponding to a plurality of illumination settings, and identifying the illumination pattern based on the plurality of weights of the trained machine-learning model; and generate an enhanced image of the biological sample by inputting the obtained image of the biological sample into the trained machine-learning model.

An exemplary method of evaluating a treatment with respect to a disease of interest comprises: receiving a first plurality of images depicting a first set of healthy biological samples not affected by the disease of interest; receiving a second plurality of images depicting a second set of untreated biological samples affected by the disease of interest; receiving a third plurality of images depicting a third set of treated biological samples affected by the disease of interest and treated by the treatment; inputting the first plurality of images into a trained machine-learning model to obtain a first plurality of enhanced images; inputting the second plurality of images into the trained machine-learning model to obtain a second plurality of enhanced images; inputting the third plurality of images into the trained machine-learning model to obtain a third plurality of enhanced images; comparing the first plurality of enhanced images, the second plurality of enhanced images, and the third plurality of enhanced images to evaluate the treatment.

In some embodiments, the first plurality of images, the second plurality of images, and the third plurality of images are bright-field images.

In some embodiments, the first plurality of enhanced images, the second plurality of enhanced images, and the third plurality of enhanced images are fluorescence images.

In some embodiments, the first plurality of enhanced images, the second plurality of enhanced images, and the third plurality of enhanced images are phase images.

In some embodiments, comparing the first plurality of enhanced images, the second plurality of enhanced images, and the third plurality of enhanced images to evaluate the treatment comprises: identifying, in each image, a signal associated with a biomarker.

In some embodiments, comparing the first plurality of enhanced images, the second plurality of enhanced images, and the third plurality of enhanced images to evaluate the treatment further comprises: determining a first distribution based on signals of the biomarker in the first plurality of enhanced images; determining a second distribution based on signals of the biomarker in the second plurality of enhanced images; and determining a third distribution based on signals of the biomarker in the third plurality of enhanced images.

In some embodiments, comparing the first plurality of enhanced images, the second plurality of enhanced images, and the third plurality of enhanced images to evaluate the treatment further comprises: comparing the first distribution, the second distribution, and the third distribution to evaluate the treatment.

In some embodiments, comparing the first plurality of enhanced images, the second plurality of enhanced images, and the third plurality of enhanced images to evaluate the treatment comprises: determining, for each image, a score indicative of the statement of the disease of interest.

In some embodiments, comparing the first plurality of enhanced images, the second plurality of enhanced images, and the third plurality of enhanced images to evaluate the treatment further comprises: determining a first distribution based on scores of the first plurality of enhanced images; determining a second distribution based on scores of the second plurality of enhanced images; and determining a third distribution based on scores of the third plurality of enhanced images.

In some embodiments, comparing the first plurality of enhanced images, the second plurality of enhanced images, and the third plurality of enhanced images to evaluate the treatment further comprises: comparing the first distribution, the second distribution, and the third distribution to evaluate the treatment.

In some embodiments, the treatment is a first treatment, the method further comprising: receiving a fourth plurality of images depicting a fourth set of treated biological samples affected by the disease of interest and treated by a second treatment; inputting the fourth plurality of images into the trained machine-learning model to obtain a fourth plurality of enhanced images; comparing the first plurality of enhanced images, the second plurality of enhanced images, the third plurality of enhanced images, and the fourth plurality of enhanced images to compare the first treatment and the second treatment.

In some embodiments, the method further comprises: selecting a treatment out of the first treatment and the second treatment based on the comparison.

In some embodiments, the method further comprises: administering the selected treatment.

In some embodiments, the method further comprises: providing a medical recommendation based on the selected treatment.

In some embodiments, the trained machine-learning model is is a GAN model comprising a discriminator and a generator.

In some embodiments, the machine-learning model is a conditional GAN model.

In some embodiments, the generator comprises a plurality of neural networks corresponding to a plurality of frequency groups.

In some embodiments, each neural network of the plurality of neural networks is configured to generate wavelet coefficients for a respective frequency group.

In some embodiments, the discriminator is a PatchGAN neural network.

An exemplary system for evaluating a treatment with respect to a disease of interest comprises: one or more processors; a memory; and one or more programs, wherein the one or more programs are stored in the memory and configured to be executed by the one or more processors, the one or more programs including instructions for: receiving a first plurality of images depicting a first set of healthy biological samples not affected by the disease of interest; receiving a second plurality of images depicting a second set of untreated biological samples affected by the disease of interest; receiving a third plurality of images depicting a third set of treated biological samples affected by the disease of interest and treated by the treatment; inputting the first plurality of images into a trained machine-learning model to obtain a first plurality of enhanced images; inputting the second plurality of images into the trained machine-learning model to obtain a second plurality of enhanced images; inputting the third plurality of images into the trained machine-learning model to obtain a third plurality of enhanced images; comparing the first plurality of enhanced images, the second plurality of enhanced images, and the third plurality of enhanced images to evaluate the treatment.

An exemplary non-transitory computer-readable storage medium stores one or more programs for evaluating a treatment with respect to a disease of interest, the one or more programs comprising instructions, which when executed by one or more processors of an electronic device, cause the electronic device to: receiving a first plurality of images depicting a first set of healthy biological samples not affected by the disease of interest; receiving a second plurality of images depicting a second set of untreated biological samples affected by the disease of interest; receiving a third plurality of images depicting a third set of treated biological samples affected by the disease of interest and treated by the treatment; inputting the first plurality of images into a trained machine-learning model to obtain a first plurality of enhanced images; inputting the second plurality of images into the trained machine-learning model to obtain a second plurality of enhanced images; inputting the third plurality of images into the trained machine-learning model to obtain a third plurality of enhanced images; comparing the first plurality of enhanced images, the second plurality of enhanced images, and the third plurality of enhanced images to evaluate the treatment.

BRIEF DESCRIPTION OF THE DRAWINGS

FIG. 2A illustrates an exemplary process of training and applying the machine learning model, in accordance with some embodiments.

FIG. 2B illustrates an exemplary process of training and applying the machine learning model, in accordance with some embodiments.

FIG. 4 illustrates an exemplary image formation model, in accordance with some embodiments.

FIG. 11 illustrates an exemplary method for training a machine-learning model, in accordance with some embodiments.

FIGS. 14A and 14B illustrate an exemplary process for training a machine-learning model (e.g., a GAN model) configured to generate synthetic data (e.g., image data) and identifying an optimal illumination pattern for capturing input data for the machine-learning model, in accordance with some embodiments.

FIG. 16A illustrates synthetic images generated by an exemplary GAN model to study the NASH disease, in accordance with some embodiments FIG. 16B illustrates downstream analyses of the generated images, in accordance with some embodiments.

DETAILED DESCRIPTION OF THE INVENTION

Figure 1:
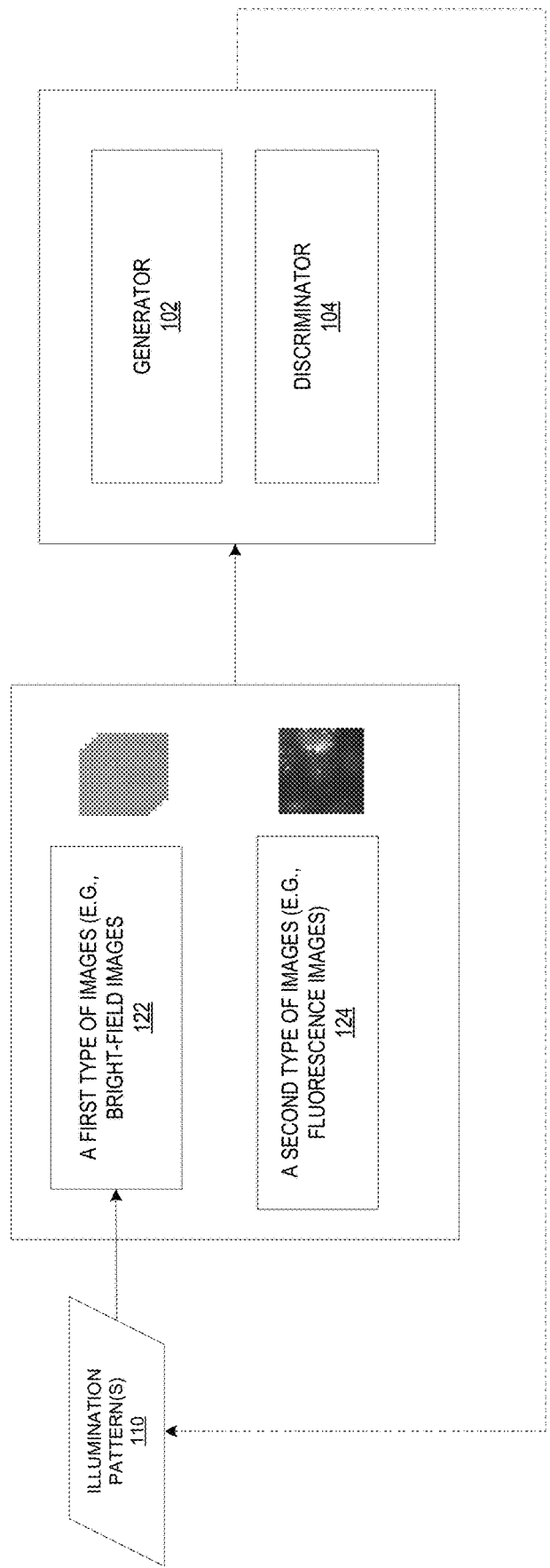
FIG. 1 illustrates an exemplary process for training a machine-learning model configured to generate synthetic data (e.g., image data) at scale in a low-cost manner, in accordance with some embodiments.

The present disclosure includes methods, systems, electronic devices, non-transitory storage media, and apparatuses for performing ML-based generation of image data at scale. The generated image data (e.g., image data of biological samples) can provide sufficient richness and depth for downstream processing (e.g., phenotyping). Further, embodiments of the present disclosure comprises a set of computational and hardware optimization methods that extends the current dimensionality of classic microscopy techniques.

Embodiments of the present disclosure can process multiple bright-field images of biological samples and produce enhanced images of the biological samples. The enhanced images include but are not limited to: fluorescence images, phase shift images, semantic map, polarization map, refractive map (2D and 3D), absorbance map, and other image modalities. Bright-field images of biological samples can be obtained at scale and at low cost due to inexpensive equipment (e.g., relative to fluorescence microscopes), ease of clinical deployment, and low processing and storage resource requirements. Obtaining bright-field images is generally non-invasive and involves low photo-toxicity. Thus, bright-field images can be obtained efficiently and at scale. The enhanced images provide sufficient richness and depth for downstream processing (e.g., phenotypic exploration).

Embodiments of the present disclosure include a machine-learning model that is trained to receive a first type of image and translate the input image into other imaging modalities. An exemplary machine-learning model can receive the first type of image and translate the input image into a second type of image (e.g., an enhanced image). In some embodiments, different image types refer to different imaging modalities. In some embodiments, the first type of images are bright-field images. For example, the bright-field images can be captured from illuminating in vitro (or biopsy) cell samples with an inexpensive LED array. The second type of images include fluorescence images. The generated fluorescence images exhibit high contrast features that are not directly visible in bright-field images and can be used for downstream processing (e.g., phenotyping).

Embodiments of the present disclosure reduce or eliminate the need to capture real fluorescence images (or other special image modalities) of biological samples for downstream analysis, and allow bright-field images to be widely used for a variety of purposes. This is particularly beneficial to live cell imaging. For example, the disclosed methods could be used for the monitoring and optimization of cell differentiation experimental protocols. In the context of chemical or genetic perturbation, time consuming activities linked to cells staining and fixation could be avoided. In some embodiments, the dosing time, which is the incubation time of a drug with the cells under observation could also be optimized by the software. Researchers would no longer to need to arbitrarily decide the best incubation time, as the software would be able to notify the researcher of the optimized incubation time. Further, the machine-learning techniques used to translate the bright-field images into other modalities require lower processing and storage resource utilization. Thus, embodiments of the present disclosure present technical improvements in the field of medical imaging while enhancing the operability and functioning of computing systems.

Embodiments of the present disclosure further include a machine-learning model that is trained to receive the first type of image and translate the input image into a third type of image. In some embodiments, the third type of image include image data indicative of various optical properties (e.g., phase shift) of the biological sample captured.

Embodiments of the present disclosure further include a machine-learning model that is trained to receive the first type of image and translate the input image into a fourth type of image. In some embodiments, the fourth type of image includes image data indicative of segmentation data (e.g., cell boundaries).

One of ordinary skill in the art should appreciate that embodiments of the present disclosure can further translate input images into numerous other types of image capturing a variety of imaging characteristics, such as a semantic map, a polarization map, a refractive map (2D or 3D), absorbance map, etc.

In some embodiments, a single machine-learning model is trained to perform multiple translation tasks simultaneously. For example, the same machine-learning model can receive the first type of image and generate multiple types of images (e.g., second type, third type, fourth type of image). The machine-learning model can be a Generative Adversarial Network ("GAN") model. For example, the GAN network can be a conditional GAN ("cGAN") model.

In some embodiments, the machine-learning model converts an input image into its corresponding wavelet coefficients and generates one or more output images in wavelet coefficients. The compact and multi-scale representation of images coupled with the intrinsic non-linear options of a neural network achieves multiple goals at once. First, the wavelet-based representation solves the inherent class imbalance problem that most of the generative models face. Specifically, most input image data comprise abundant low frequency signals but fewer high frequency signals. Second, the wavelet-based representation extracts and maintains the overall geometry of the input image data. The discriminator of the model ensures that the real and generated images (e.g., real v. generated fluorescence images) are indistinguishable. The generated fluorescence images, or other enhanced image modality, corresponds to the virtual staining of the sample. Because of the low photo-toxicity of the bright-field imaging modality, as well as its availability in the clinical setup, virtual staining by embodiments of the present disclosure can be performed on live cells as well as biopsy samples.

Embodiments of the present disclosure further includes hardware optimization methods. For example, embodiments of the present disclosure can further optimize the illumination schema of a microscope (e.g., the microscope that obtains the first type of images) dynamically. In some embodiments, the microscope that is used to capture the first type of images can be tuned or programmed to provide different illumination schemes during the training process. During training of the machine-learning model, an optimal illumination scheme for capturing the first type of images can be identified. The optimal illumination scheme can be used to capture the first type of images (e.g., bright-field images) so as to extract the best representation of the biological sample for wavelet-based image transformation (e.g., for downstream phenotypic exploration).

Embodiments of the present disclosure further includes evaluating the robustness of the generated images of the machine-learning model. In some embodiments, a first downstream classifier is trained using real images (e.g., real fluorescence images), and a second downstream classifier is trained using generated images (e.g., generated fluorescence images). The performance of the two classifiers can be compared to evaluate the robustness of the generated images as training data in downstream tasks.

Thus, embodiments of the present disclosure comprise an integrated platform that simultaneously solves many problems: image enhancement, phase retrieval, low photo-toxicity, realistic virtual painting of bright-field images, and robustness in downstream tasks. Embodiments of the present disclosure can evaluate the robustness of the generated images via downstream classification tasks. These tasks are integrated to the platform and close the loop of data generation from non-invasive bright-field images to fluorescent images. For example, the system may optimize parameters of the bright-field microscope acquisition system during use. Illumination patterns of the LED array, and other parameters of the bright-field microscope acquisition system, including, for example, the focus position of the microscope objective and activation timings of a spatial light modulator (SLM) may be optimized by back-propagation during downstream classification tasks.

Further still, in some embodiments the platform performs a cascade of perturbations to the cells and learn to optimize the illumination scheme to extract the best representation of the cells for phenotypic exploration.

Some embodiments of the present disclosure can identify one or more optimal illumination patterns for capturing image data. In some embodiments, an illumination pattern can indicate whether each illumination emitter of an illumination source (e.g., each LED on a LED array) is to be turned on or off and the intensity of each illumination emitter. The system can determine an optimal illumination pattern by training a machine-learning model having an attention layer comprising an plurality of weights corresponding to the intensities of a plurality of illumination emitters (e.g., a plurality of weights corresponding to the intensities of a plurality of LEDs on the LED array). During training of the machine-learning model, the plurality of weights are applied to a plurality of training images (e.g., bright-field images) illuminated by different illumination emitters. The aggregated image can be inputted into the machine-learning model to determine a loss and the model, including the weights in the attention layer, can be updated based on the loss accordingly. After training, an illumination pattern can be determined based on the weights in the attention layer of the trained machine-learning model, as each weight can correspond to the desired intensity level of the corresponding illumination emitter. Accordingly, the process involves only capturing images using a limited number of illumination settings (e.g., turning on a single illumination emitter at a time to capture images) and does not require physically adjusting the intensities of the illumination emitters in order to identify an optimal illumination pattern.

Some embodiments of the present disclosure can train a machine-learning model such that the synthetic image data generated by the machine-learning model can provide the same performance in downstream analyses as real images. In some embodiments, training the machine-learning model comprises first training a classifier corresponding to the downstream task (e.g., classifying healthy v. diseased tissues based on an image) and then using the outputs of the classifier to guide the training of the machine-learning model.

Some embodiments of the present disclosure can evaluate candidate treatments with respect to a disease of interest. In some embodiments, the system receives a first plurality of images depicting a first set of healthy biological samples not affected by the disease of interest; receives a second plurality of images depicting a second set of untreated biological samples affected by the disease of interest; and receives a third plurality of images depicting a third set of treated biological samples affected by the disease of interest and treated by the candidate treatment. The images are inputted into a machine-learning model to obtain enhanced images, and the enhanced images are compared to evaluate the treatment (e.g., by analyzing the distributions of the images).

The following description sets forth exemplary methods, parameters, and the like. It should be recognized, however, that such description is not intended as a limitation on the scope of the present disclosure but is instead provided as a description of exemplary embodiments.

In some embodiments, an exemplary optical system comprises a programmable spatial light modulator ("SLM"). The SLM of the optical system can improve the performance of a machine-learning model via the training stage (e.g., by providing a rich training dataset) and/or via the inference stage (e.g., by providing input data under a variety of optical settings or an optimal setting). The SLM is programmed without requiring any mechanical movement or mechanical modifications to the optical system.

The SLM provides additional degrees of freedom and sources of contrast to control the microscope in a programmable way. For example, the SLM can be programmed to generate optical aberrations that enhance critical phenotypes. As another example, the SLM can be programmed to provide different modulations, thus producing a variety of images that allow the exploration of deep samples at a high speed. The SLM also allows identification of an optimal imaging setup to infer cellular phenotypes and reconstruct alternative images modalities in a supervised fashion. Multi-focus acquisitions are possible without any mechanical movements, thus accelerating and improving the downstream tasks. Three-dimensional phase tomography and reconstruction are therefore accelerated and improved.

Although the following description uses terms "first," "second," etc. to describe various elements, these elements should not be limited by the terms. These terms are only used to distinguish one element from another. For example, a first graphical representation could be termed a second graphical representation, and, similarly, a second graphical representation could be termed a first graphical representation, without departing from the scope of the various described embodiments. The first graphical representation and the second graphical representation are both graphical representations, but they are not the same graphical representation.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1 illustrates an exemplary process for training a machine-learning model configured to generate enhanced images of biological samples, in accordance with some embodiments.

With reference to FIG. 1, training data 120 comprises a first type of images 122 and a second type of images 124. In some embodiments, the images are images of biological samples, and the biological samples can include one or more collections of stained, unstained, perturbed and/or unperturbed biological samples.

In some embodiments, the first type of image data 122 comprises a set of bright-field images, and the second type of image data 124 comprises images in a different modality (e.g., fluorescence images). The first type of images 122 can be obtained using a bright-field microscope, while the second type of images 124 can be obtained using a fluorescence microscope.

As shown in FIG. 1, the first type of images 122 are obtained based on one or more illumination pattern(s) 110. An illumination pattern is indicative of the settings with which an object is illuminated. In some embodiments, an illumination pattern can be defined by one or more parameters indicating the spatial relationship (e.g., distance, angle) between the object and the illumination source, one or more parameters indicating the setup of the illumination source, or a combination thereof. For example, an illumination pattern can indicate a set of activated LED light sources, a specific out-of-focus/polarization setup, etc.

In some embodiments, the microscope that captures the first type of images can be a microscope that supports multiple illumination patterns. For example, the microscope can provide a programmable illumination source (e.g., LED array, laser), an adaptive optics system (SLM, micro-mirrors), or a combination thereof. By updating the illumination pattern (e.g., controlling illumination sources and/or the pupil function of the optics system), many representations of the biological sample corresponding to multiple illumination patterns can be acquired.

In some embodiments, the training data 120 can be organized as three-dimensional image data (e.g., an image array). For example, the training data 120 can be of dimensions (B, C, H, W) in which B indicates the batch size, C indicates the number of channels (i.e., illumination patterns), H indicates the height, and W indicates the width. C equals 1 if there is only a single bright-field image, and C is larger than 1 if there is a stack of bright-field images.

In some embodiments, one or more images in the training data 120 can be normalized before they are used to train the machine-learning model 100. For example, fluorescence images can be normalized based on illumination or intensity parameters.

With reference to FIG. 1, the training data 120 is used to train the machine-learning model 100. In some embodiments, the model 100 is a Generative Adversarial Network ("GAN") model. For example, the GAN network can be a conditional GAN ("cGAN") model. As described in detail below, the GAN network comprises a generator and a discriminator. The generator is trained to receive the first type of images (e.g., bright-field images) and translate the input images into the second type of images (e.g., fluorescence images). The training step includes comparing real images of the first type 122 with real images of the second type 124 to determine a ground truth baseline for what a wavelet-based transformation of the first type of image 122 should seek to accomplish. During training, the generator output (i.e., the generated fluorescence images) can be connected directly to the discriminator input. The discriminator is trained to distinguish the generated images of the second type (e.g., generated fluorescence images) from real images of the second type (e.g., real fluorescence images). Through back-propagation, the discriminator's output can be used by the generator to update the generator's weights such that the generator learns to generate images that the discriminator will classify as real images.

In some embodiments, the illumination parameters can be updated during the training of the model 100. Thus, during training of the model 100, the illumination scheme can be continually updated and training data can be obtained according to the updated illumination scheme to further train the model 100, as described in detail below.

FIGS. 2A and 2B illustrate exemplary processes 200 and 250 for training and applying the machine learning model (e.g., model 100), in accordance with some embodiments. FIG. 2A illustrates the process when the parameters of the microscope cannot be changed during acquisition of the training data. FIG. 2B illustrates the process when the parameters of the microscope can be changed during acquisition of the training data and thus an optimal illumination pattern can be identified.

Each of the processes can be performed at least in part using one or more electronic devices. In some embodiments, the blocks of each process step depicted in FIGS. 2A and 2B can be divided up between multiple electronic devices. In each process, some blocks are, optionally, combined, the order of some blocks is, optionally, changed, and some blocks are, optionally, omitted. In some examples, additional steps may be performed in combination with the process. Accordingly, the operations as illustrated (and described in greater detail below) are exemplary by nature and, as such, should not be viewed as limiting.

In FIG. 2A, the parameters of the microscope cannot be changed during the acquisition of the bright-field images. Thus, all of the bright-field images in the training data (e.g., training data 120) are obtained based on the same illumination pattern.

At block 204, training data (e.g., training data 120 in FIG. 1) is obtained at least partially according to the default illumination pattern. As described above with reference to FIG. 1, the training data comprises a first type of images (e.g., bright-field images), which are obtained according to the default illumination pattern by a bright-field microscope, and a second type of images (e.g., fluorescence images) obtained by a fluorescence microscope.

At block 206, a machine-learning model (e.g., model 100 in FIG. 1) is trained based on the training data. The model can be a GAN model. For example, the GAN network can be a conditional GAN ("cGAN") model.

Figure 3A:
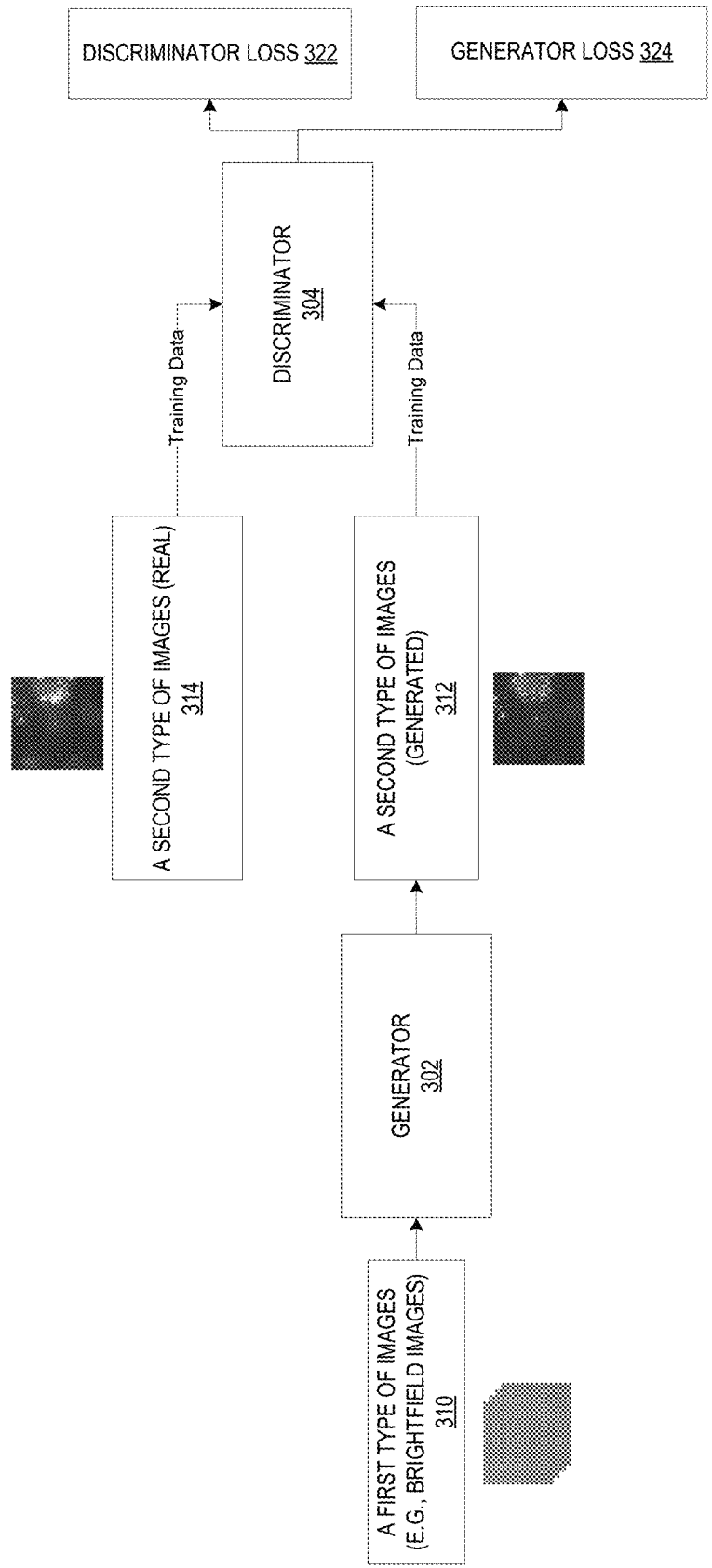
FIG. 3A illustrates the training process of the machine-learning model, in accordance with some embodiments.
Figure 3B:
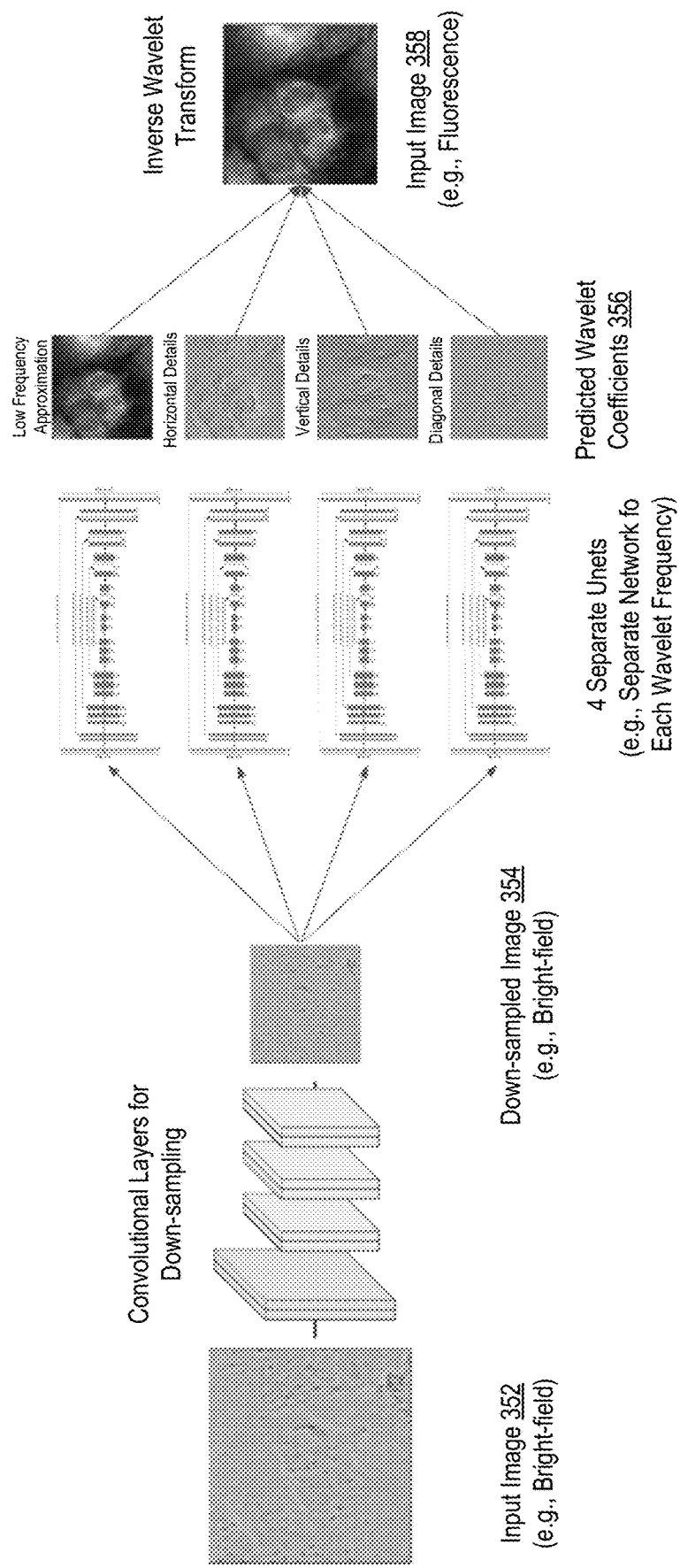
FIG. 3B illustrates operations of an exemplary generator, in accordance with some embodiments.
Figure 3C:
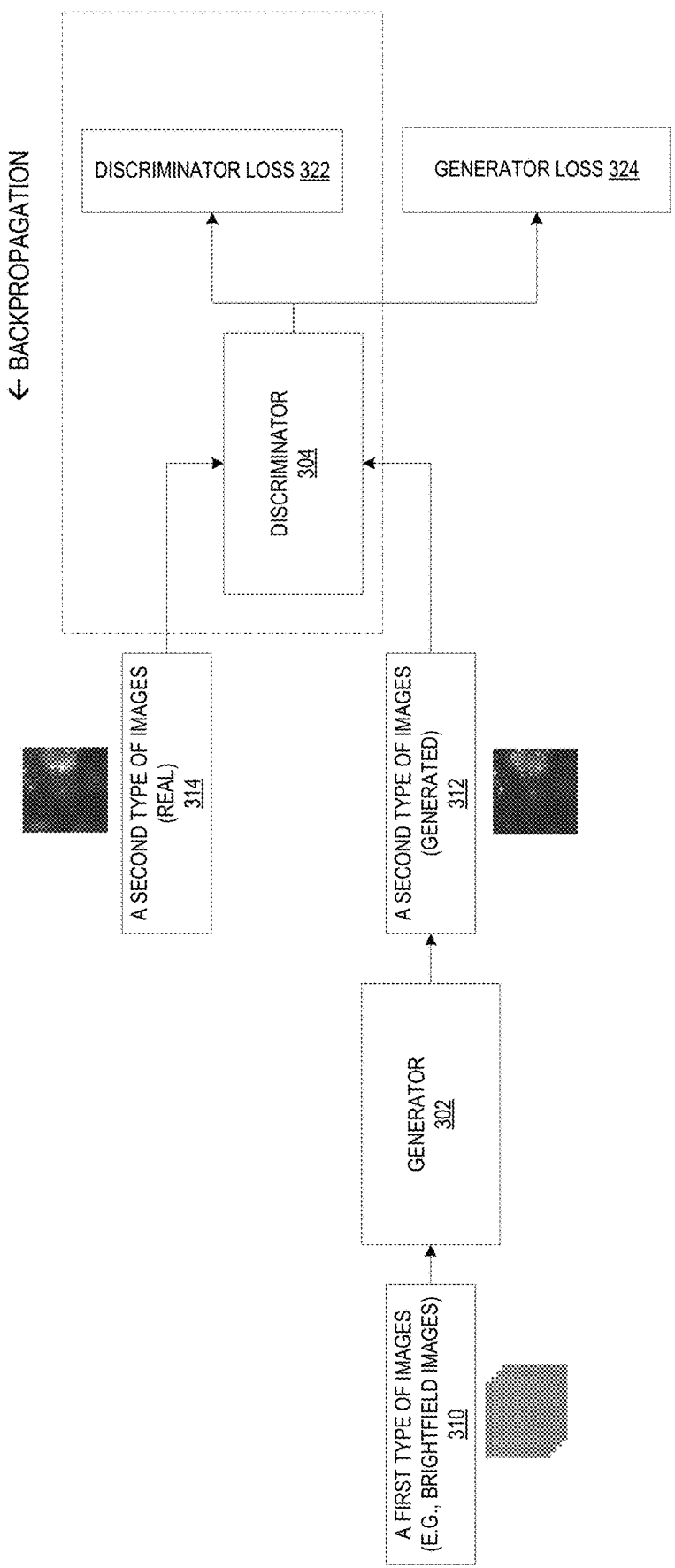
FIG. 3C illustrates the training process of the machine-learning model, in accordance with some embodiments.
Figure 3D:
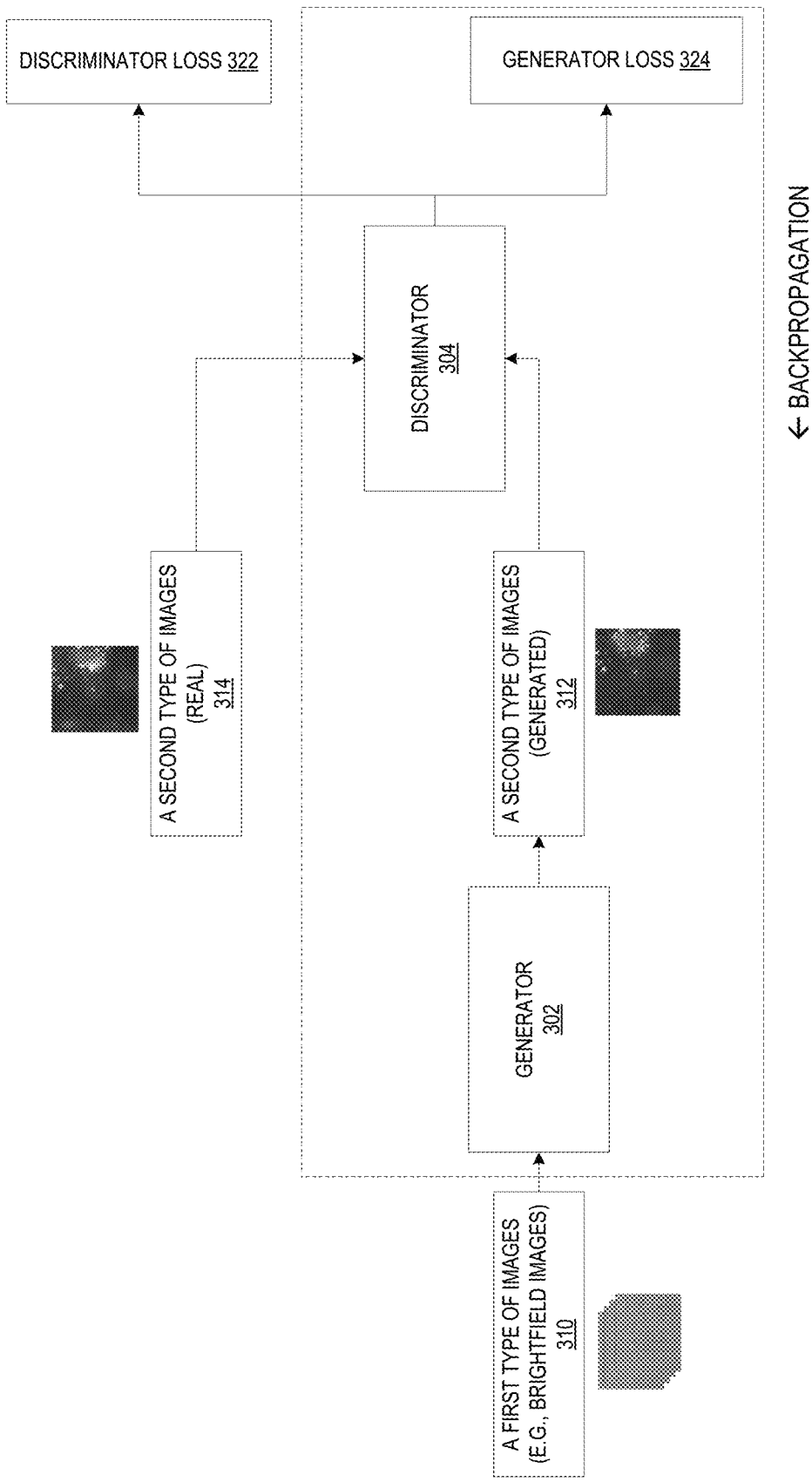
FIG. 3D illustrates the training process of the machine-learning model, in accordance with some embodiments.

FIGS. 3A, 3C, and 3D illustrates the training process of the machine-learning model, in accordance with some embodiments. The GAN model comprises the generator 302 and a discriminator 304. The generator 302 is trained to receive a first type of images 310 (e.g., bright-field images) and generate a second type of images 312 (e.g., fluorescence images). In some embodiments, the first type of images 310 comprises the bright-field image array described above.

During training, the generator output (i.e., the generated fluorescence images) can be connected directly to the discriminator input. The discriminator 304 is trained to distinguish the generated images of the second type 312 (e.g., generated fluorescence images) from real images of the second type 314 (e.g., real fluorescence images). In some embodiments, the real images of the second type 314 comprises the fluorescence image array described above.

Through back-propagation, the discriminator's output can be used by the generator to update the generator's weights such that the generator learns to generate images that the discriminator will classify as real images, as described in detail below. In some embodiments, the generator 302 and the discriminator 304 are neural networks.

FIG. 3B illustrates operations of an exemplary generator, in accordance with some embodiments. The input image 352 can be a single image from a bright-field image array or an entire bright-field image array. For example, the input image 352 can be of dimensions (B, C, H, W) in which B indicates the batch size, C indicates the number of channels, H indicates the height, and W indicates the width. C equals 1 if there is only a single bright-field image, and C is larger than 1 if there is a stack of bright-field images.

With reference to FIG. 3B, the generator comprises a series of convolutional layers for down-sampling the input image 352 to obtain a down-sampled input image 354. In some embodiments, the input image 353 can be down-sampled to half of its original size. For example, if the input is 256*256 in the spatial size, it will be reduced to 128*128.

The down-sampled image 354 is then passed to a plurality of neural networks. In the depicted example, the plurality of neural networks comprises four U-Net neural networks. A U-Net network is a convolutional network for image-to-image translation. Details of the design and implementation of a U-Net network can be found, for example, in Ronneberger et al., "U-Net: Convolutional Networks for Biomedical Image Segmentation," which is hereby incorporated by reference in its entirety.

The plurality of neural networks can correspond to different frequency groups in the wavelet domain. In the depicted example, the four U-Net networks are responsible for low frequency, high frequency (horizontal), high frequency (vertical), and high frequency (diagonal), respectively. In signal processing low frequency signals correspond to very large features with respect to the size of the image (for example when imaging cells, having a size magnitude of the order of the cytoplasm or the nucleus). High frequency information are very fine small image features (for example, having a size magnitude of the order of mitochondria, microtubules). Low frequency signals correspond to the first scale of wavelet coefficients. The high frequency are encoded in higher scale wavelet coefficients. In some embodiments, the plurality of neural networks operate independently and do not share weights.

As shown, three of the four U-Net branches correspond to high frequency blocks. Low frequency information is relatively easy to recover; thus, having more computing power dedicated to the high frequency guarantee the reconstruction of fine details in the images. Therefore, the loss function operating in the wavelet domain benefits from this organization of the signal (3 times more high frequency information than low frequency information)

Each neural network is configured to output (or predict) wavelet coefficients for the respective frequency group. A loss function is applied to the predicted wavelet coefficients 356 and the true wavelet coefficients of the real fluorescence image. The loss function is described further below with reference to FIGS. 3C and 3D.

The generated fluorescence image 358 in the image domain can be obtained by applying inverse wavelet transform on predicted coefficients 356.

FIG. 3C illustrates the back-propagation process of the discriminator 304, according to some embodiments. The discriminator 304 is a model (e.g., a neural network) trained to provide an output based on a given image. The training data of the discriminator 304 comprises real images of the second type 314 (e.g., real fluorescence images) and synthetic images of the second type 312 (e.g., generated fluorescence images) generated by the generator 302.

In some embodiments, the discriminator 304 is a Patch-GAN network. Details of the design and implementation of the PatchGAN network can be found, for example, in Isola et al., "Image-to-Image Translation with Conditional Adversarial Networks," which is incorporated by reference in its entirety.

During training of the discriminator 304, a discriminator loss 322 can be calculated based on the generator's outputs (i.e., the predicted wavelet coefficients). In some embodiments, the discriminator loss function is a Wasserstein discriminator loss and calculated as follows:

$$\nabla_w \frac{1}{m} \sum_{i=1}^{m} [f(x^{(i)}) - f(G(z^{(i)}))]$$

where f(x) is the discriminator's output based on wavelet coefficients of a real fluorescence image, w is the model weights of the discriminator, m is the size of the mini-batch, f is the discriminator model, x is the real image, z is the input (bright-field), G is the generator model, and f(G(z)) is the discriminator's output based on the predicted wavelet coefficients corresponding to a synthetic fluorescence image.

The discriminator 304 is configured to maximize this function. In other words, it tries to maximize the difference between its output based on real images and its output based on synthetic images. As depicted in FIG. 3C, the discriminator updates its weights through back-propagation based on the discriminator loss 332 through the discriminator network.

FIG. 3D illustrates the back-propagation process of the generator 302, according to some embodiments. The generator 302 is a neural network configured to receive a first type of images 310 and generate a second type of images 312, as described with reference to FIGS. 3A and 3B. The predicted wavelet coefficients by the generator are inputted into the discriminator 304. Depending on the discriminator's outputs, a generator loss 324 can be calculated. In some embodiments, the generator loss function is a Wasserstein generator loss and calculated as follows:

$$\nabla_\theta \frac{1}{m} \sum_{i=1}^{m} [f(G(z^{(i)}))]$$

where f(x) is the discriminator's output based on wavelet coefficients of a real fluorescence image, m is the size of the mini-batch, f is the discriminator model, z is the input (bright-field), G is the generator model, and f(G(z)) is the discriminator's output based on the predicted wavelet coefficients.

The reconstruction loss, operating in the wavelet domain, has the property to naturally balance the contribution of low and high frequencies. As shown in FIG. 3B, the wavelet coefficients can be split into two categories: low (one block) and high frequency (3 blocks). Three of the four UNet branches can be dedicated to the high frequency blocks. Low frequency information can more easily be recovered; therefore, having more computing power dedicated to the high frequency helps with the reconstruction of fine details in the images. The loss function operating in the wavelet domain, benefits from this organization of the signal (three times more high frequency information than low frequency information). In some embodiments, the wavelet coefficients can be split into more than two categories, for example, three categories (high, medium, low frequencies), four categories, or more than four categories.

The generator 302 is configured to maximize this function. In other words, it tries to maximize the discriminator's output based on its synthetic images. In some embodiments, the generator loss is back-propagated through both the discriminator 304 and the generator 302 to obtain gradients, which are in turn used to adjust the generator weights.

In some embodiments, the generator 302 and the discriminator 304 are trained in alternating periods. In each period, the discriminator trains for one or more epochs, and the generator trains for one or more epochs. During the discriminator training, the generator may remain constant. Similarly, during the generator training, the discriminator may remain constant.

In some embodiments, the generator can translate the input image into a third type of image (e.g., phase shift image). For example, in addition to the generated fluorescence images, the generator may also output phase shift images in which each pixel indicates local value of the phase in the image (e.g., −5 to 5 phase information) that can be converted. A physics-based image formation model can be used to generate real phase shift images (i.e., the ground-truth phase shift images). The image formation model generates images given an absolute knowledge of the microscope (e.g., the aberrations of the optical system) as well as the optical properties of the sample captured (e.g., refractive index, phase). Because the optical properties of the sample can be compared between samples, the risk of batch effects in downstream tasks is almost null. A physics based model allows the incorporation of solid a priori knowledge in the generative process.

With reference to FIG. 4, during training, S, the illumination source, is optimized in order to retrieve X with high fidelity. The microscope PSF (or pupil function) can also be optimized with a spatial light modulator or a set of micromirrors. Additionally, the polarization of S can also be modulated in order to inject more contrast in the collected images.

$$I = \int |\int X(r) e^{ifr} P(f-r) dr|^2 S(f) df$$

In the formula above, S(f) refers to the partially coherent illumination source (LED array). X(r) refers to the sample's complex electronic field. P(r) refers to the microscope's point spread function (PSF). RI(r) refers to the refractive index. I refers to the image. The forward model is applied outside of the training loop to obtain the ground truth phase.

In some embodiments, the generator can translate the input image into a fourth type of image. In some embodiments, the fourth type of image include image data indicative of segmentation data (e.g., cell boundaries). In some embodiments, the loss function depends on the image modality supported. For semantic segmentation, a L1 norm can be used to infer the discrete labels in the images. For another image modality, another branch can be added to the generator to output the new modality.

Turning back to FIG. 2A, at block 208, metadata can be associated with the trained machine-learning model. The metadata can include the default illumination pattern (e.g., parameters of the bright-field microscope).

At block 210, one or more images of the first type (e.g., bright-field images) are obtained. In some embodiments, the images are obtained using the same illumination pattern (e.g., as indicated in the metadata in block 208).

At block 212, the one or more images are inputted into the generator (e.g., generator 302) of the trained machine-learning model. The generator has been trained to translate the first type of images into the second type of images (e.g., fluorescence images). At block 214, one or more images of the second type are obtained. As described below, the generated fluorescence images in turn can be used as training data for other machine-learning models, thus eliminating the need to obtain real fluorescence images as training data.

FIG. 2B illustrate the process when the parameters of the microscope can be changed during acquisition of the training data and thus an optimal illumination pattern can be identified. For example, the parameters of the microscope can be programmable such that multiple illumination patterns can be provided by the microscope.

At block 252, an illumination pattern is loaded onto a microscope. At block 254, bright-field training images are captured according to the illumination pattern (e.g., bright-field images) and fluorescence training images are also captured by a fluorescence microscope. Blocks 252 and 254 can be repeatedly performed, as indicated by the arrow 253. In other words, a sequence of illumination patterns can be loaded onto the microscope and training data corresponding to the sequence of illumination patterns can be obtained. The sequence of illumination patterns is also referred to an illumination scheme herein.

At block 256, a machine-learning model is trained based on the training data. The model can be a GAN model that operates as described with reference to FIGS. 3A-D. For example, the GAN network can be a conditional GAN ("cGAN") model.

During training, the model updates the illumination pattern iteratively. The illumination pattern is updated by back-propagating the gradient of the loss (e.g., generator loss) to the parameters of the microscope. The training procedure of the model minimizes the overall imaging time and minimizes the loss functions associated with translation or classification tasks.

During training, the system determines which illumination pattern leads to the smallest loss (e.g., generator loss). In some embodiments, the model produces a first generator loss when translating a first image, produces a second generator loss when translating a second image, etc. The losses can be compared and the smallest loss can be identified. At block 260, the illumination pattern that has produced the smallest loss can be identified and a new illumination scheme can be identified accordingly. For example, the new illumination scheme can include the best illumination pattern and/or one or more new illumination patterns similar to the best illumination pattern. The new illumination scheme can also exclude previously included illumination patterns that have resulted in the biggest loss. As indicated by arrow 258, the identified illumination scheme can be loaded to the microscope to obtain additional training data. This process can be repeated until no more improvement (e.g., on the generator loss) is observed. The optimal illumination scheme can be stored at block 261.

At block 262, one or more images of the first type (e.g., bright-field images) are obtained. In some embodiments, the images are obtained using the optimal illumination scheme stored in block 261.

At block 264, the one or more images are inputted into the generator (e.g., generator 302) of the trained machine-learning model. The generator has been trained to translate the first type of images into the second type of images (e.g., fluorescence images). At block 266, one or more images of the second type are obtained. As described below, the generated fluorescence images in turn can be used as training data for other machine-learning models, thus eliminating the need to obtain real fluorescence images as training data.

Figure 5:
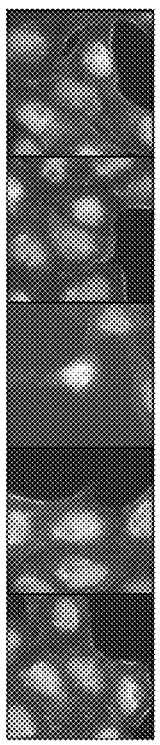
FIG. 5 illustrates outputs of an exemplary trained generator using a static microscope setup, in accordance with some embodiments.

FIG. 5 illustrates outputs of an exemplary trained generator using a static microscope setup. The trained generator receives input bright-field images and generates phase images and fluorescence images 504. For comparison, FIG. 5 also shows the corresponding real phase images and fluorescence images 506. In FIG. 5, each input image is a composite of four different illuminations. In some embodiments, the input image is a false color image representing the different illumination patterns.

Figure 6A:
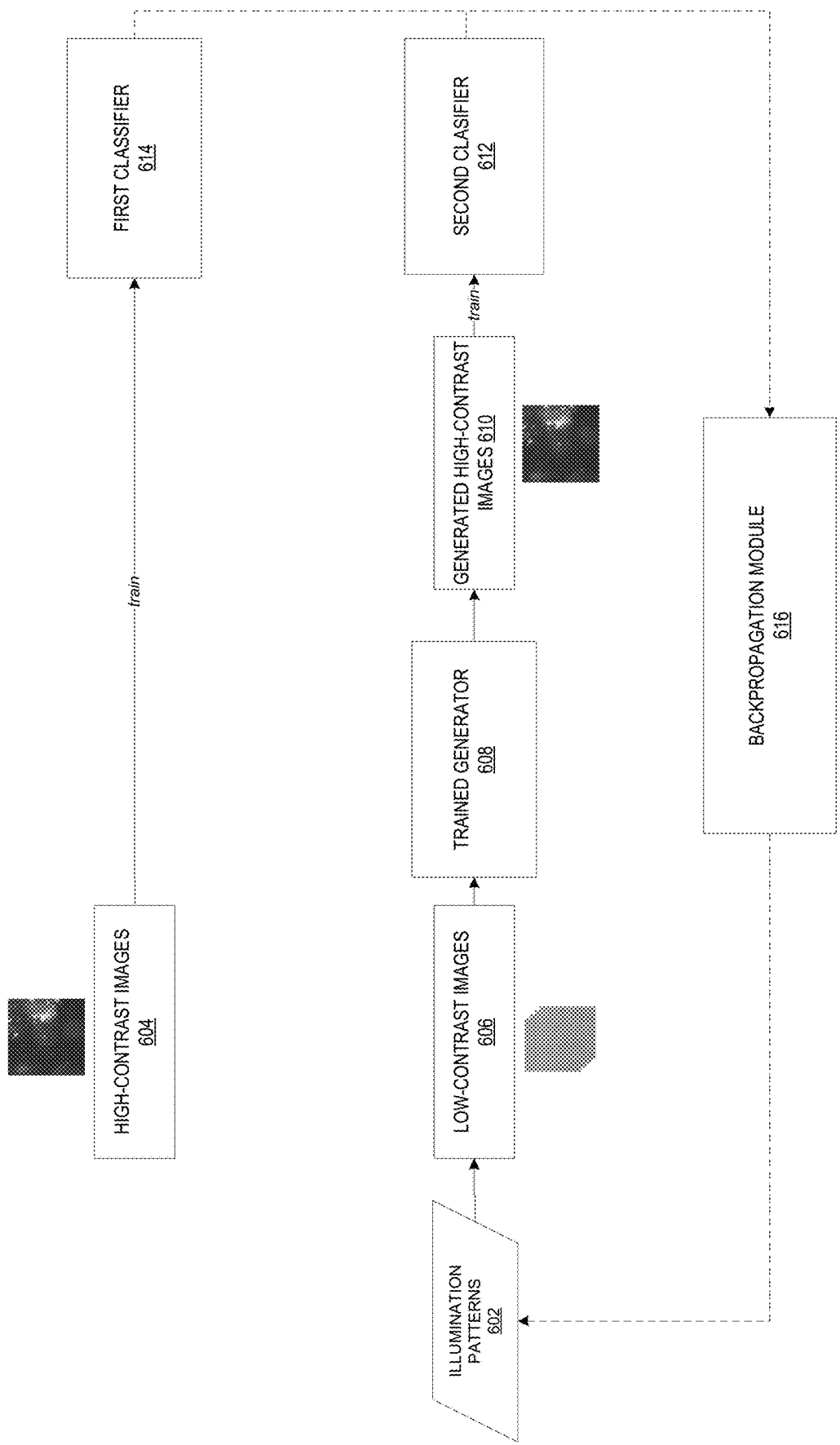
FIG. 6A illustrates an exemplary process for determining the robustness of the generated images, in accordance with some embodiments.

FIG. 6A illustrates an exemplary process for determining the robustness of the generated images, in accordance with some embodiments. Two classifiers 612 and 614 are trained to receive a fluorescence image and provide an output (e.g., a phenotype classification result). Classifier 614 is trained based on real fluorescence images 604 (e.g., real fluorescence images), while classifier 612 is trained based on generated fluorescence images 610. The generated fluorescence images are generated by a trained generator 608 (e.g., generator 102, 302) based on bright-field images 506.

In some embodiments, classifier 612 is validated using generated images, while classifier 614 is validated using real images.

Figure 6B:
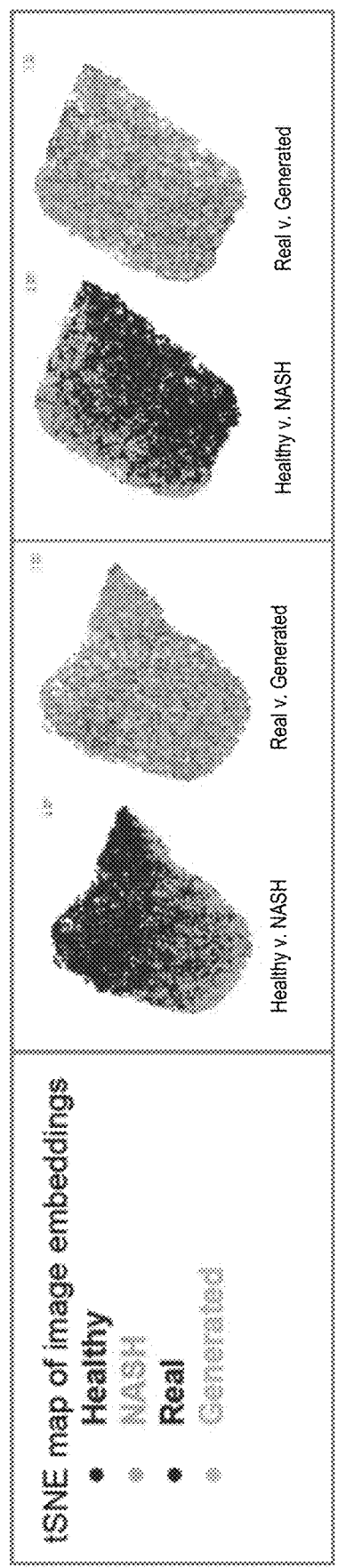
FIG. 6B illustrates an exemplary comparison between two classifiers, in accordance with some embodiments.

The performance of the classifiers 612 and 614 can be compared to determine the robustness of the generated images. FIG. 6B illustrates an exemplary comparison between two such classifiers. In this particular setup, the dataset is made of fluorescence images and 3D bright-field images of primary hepatocytes from 12 healthy donors and 12 NASH donors. A GAN model is trained to generate fluorescence images from a stack of out of focus bright-field images.

A comparison is made to determine whether a classifier trained on generated images and validated on real images performs equally well when trained on real images and validated on generated images. As shown in FIG. 6B, there is no drop in the classification accuracy and more importantly, the geometry of the embeddings space of the real images is conserved on the generated images.

Some embodiments include a back-propagation module 616. Back-propagation module 616 can be used, for example, to improve the image acquisition parameters used for acquiring bright-field images that are to be enhanced. For example, Xi can include a set parameters for the illumination patterns applied to a LED illumination array of a bright-field microscope. Xi can also include imaging parameters related to the focus position of the microscope objective and or activation parameters of a spatial light modulator (SLM). All elements of Xi may be variables of the optimization procedure. Therefore in 616 the gradient of the loss function estimated on downstream task [612] (e.g. classification, image to image translation, regression) may be back-propagated to optimize the parameters, Xi. For each update to the values of Xi a new set of images may be acquired generating a new data set of images.

In some embodiments, the data used to train the generator 608, the data used to train the first classifier 614 or the second classifier 612, and the data used to evaluate the performance of the classifiers can include overlapping images. Images used in any of the above-described processes can be annotated based on the biological samples captured (e.g., type of cells, whether diseased or healthy) and the perturbations. These annotations can be used for downstream classification tasks (e.g., as training data to train classifiers 612 and 614 in FIG. 6A) and validation of the predictive models (e.g., to evaluate the performance of the trained classifiers 612 and 614).

Figure 7A:
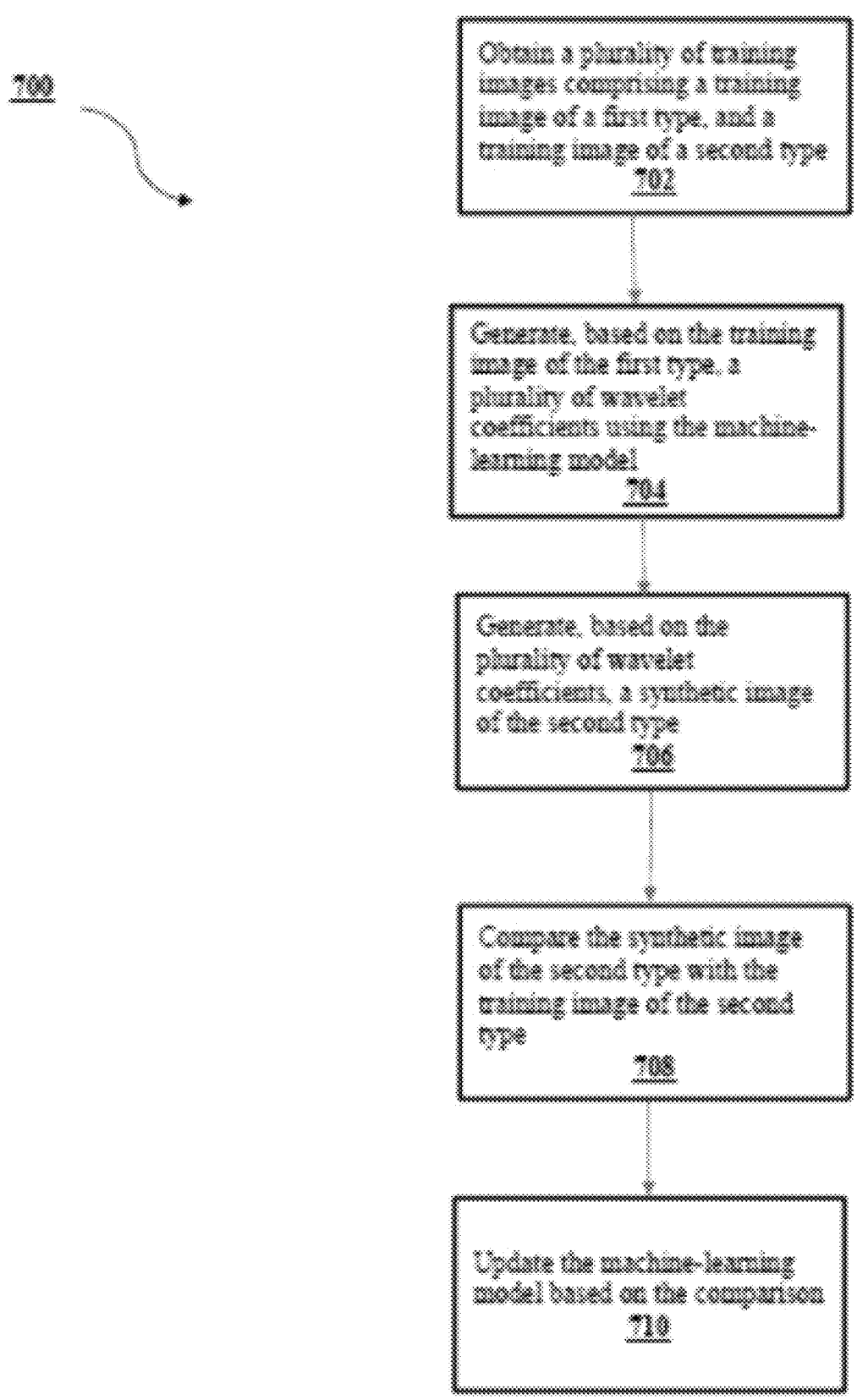
FIG. 7A illustrates an exemplary method for training a machine-learning model to generate images of biological samples.

FIG. 7A illustrates an example of a method 700 for training a machine-learning model to generate images of biological samples in accordance with one embodiment. The method includes obtaining a plurality of training images comprising a training image of a first type, and a training image of a second type at 702. The method further includes generating, based on the training image of the first type, a plurality of wavelet coefficients using the machine-learning model at 704; generating, based on the plurality of wavelet coefficients, a synthetic image of the second type at 706; comparing the synthetic image of the second type with the training image of the second type at 708; and updating the machine-learning model based on the comparison at 710.

Figure 7B:
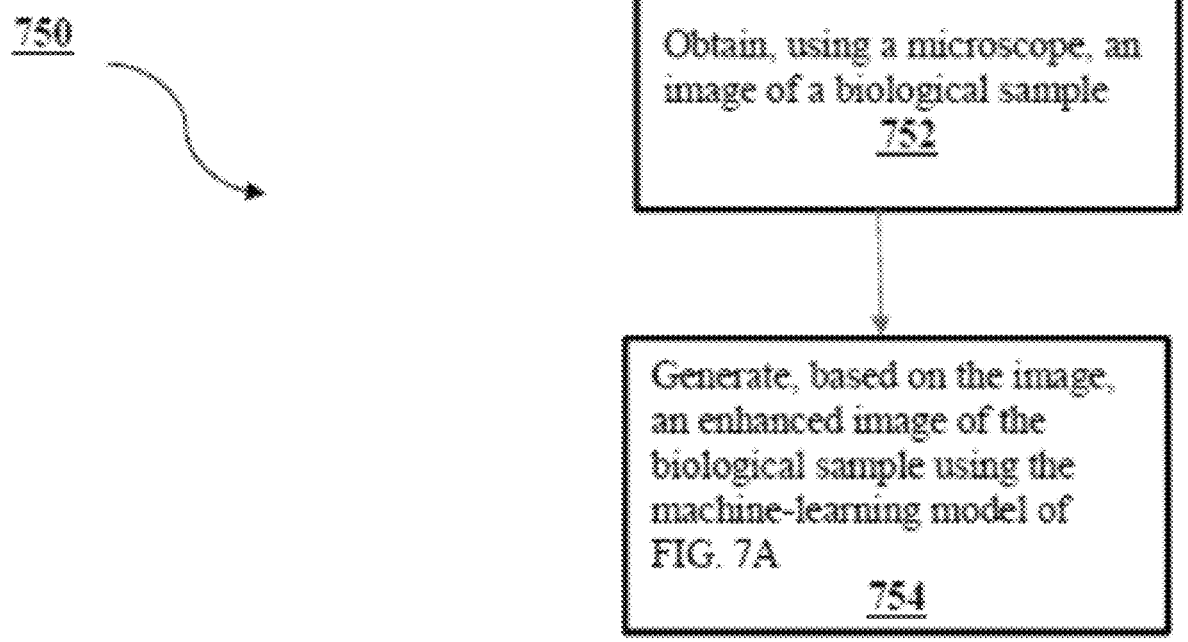
FIG. 7B illustrates an exemplary method for generating enhanced images of biological samples.

FIG. 7B illustrates an example of a method 750 for generating enhanced images of biological samples in accordance with one embodiment. The method includes obtaining, using a microscope, an image of a biological sample at 752. The method also includes at 754 generating, based on the image, an enhanced image of the biological sample using the machine-learning model of FIG. 7A.

Figure 8:
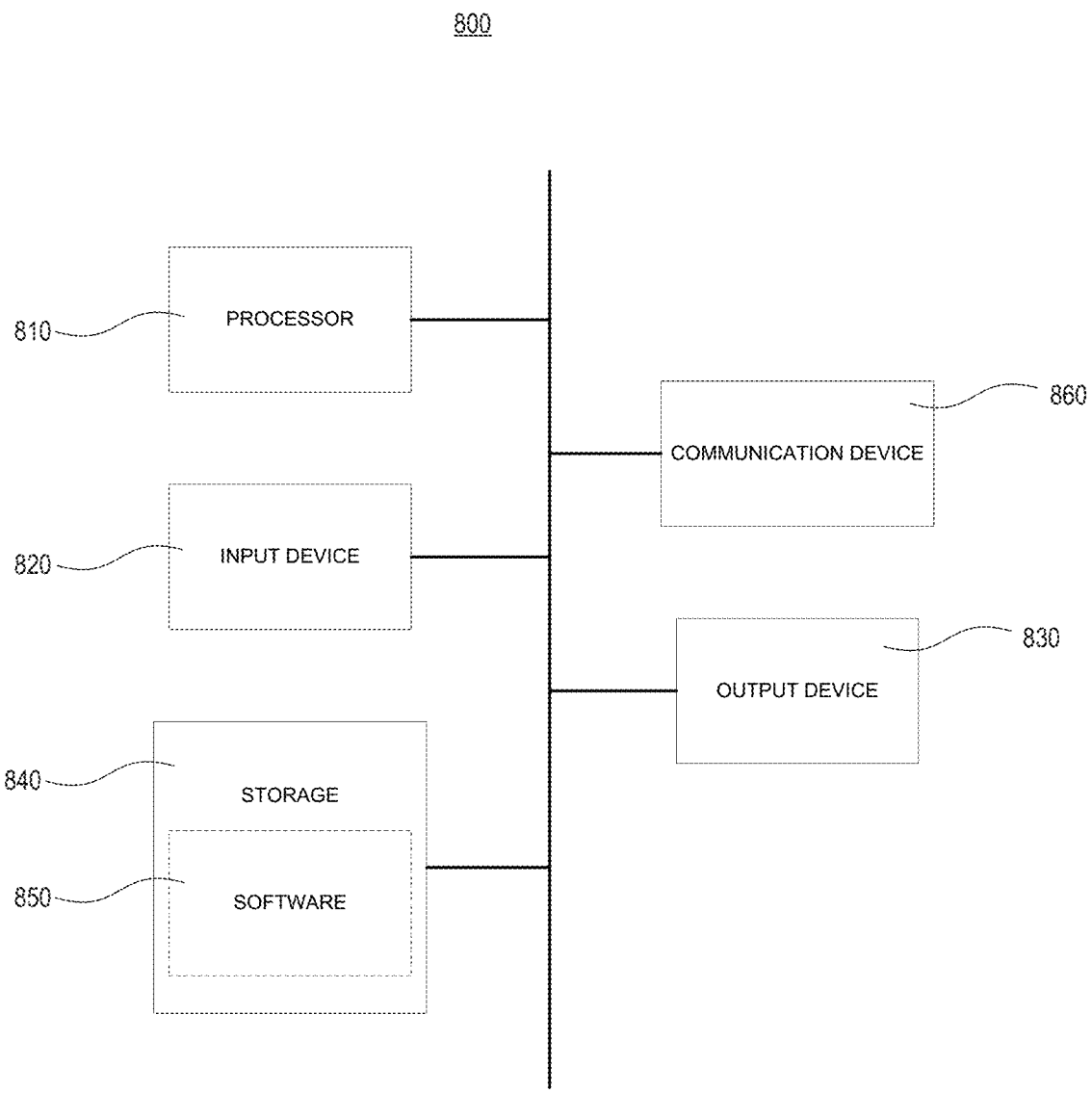
FIG. 8 illustrates an exemplary electronic device in accordance with some embodiments.

FIG. 8 illustrates an example of a computing device in accordance with one embodiment. Device 800 can be a host computer connected to a network. Device 800 can be a client computer or a server. As shown in FIG. 8, device 800 can be any suitable type of microprocessor-based device, such as a personal computer, workstation, server or handheld computing device (portable electronic device) such as a phone or tablet. The device can include, for example, one or more of processor 810, input device 820, output device 830, storage 840, and communication device 860. Input device 820 and output device 830 can generally correspond to those described above, and can either be connectable or integrated with the computer.

Input device 820 can be any suitable device that provides input, such as a touch screen, keyboard or keypad, mouse, or voice-recognition device. Output device 830 can be any suitable device that provides output, such as a touch screen, haptics device, or speaker.

Storage 840 can be any suitable device that provides storage, such as an electrical, magnetic or optical memory including a RAM, cache, hard drive, or removable storage disk. Communication device 860 can include any suitable device capable of transmitting and receiving signals over a network, such as a network interface chip or device. The components of the computer can be connected in any suitable manner, such as via a physical bus or wirelessly.

Software 850, which can be stored in storage 840 and executed by processor 810, can include, for example, the programming that embodies the functionality of the present disclosure (e.g., as embodied in the devices as described above).

Software 850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 800 can implement any operating system suitable for operating on the network. Software 850 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Optimization Using Spatial Light Modulators

In some embodiments, an exemplary optical system comprises a programmable SLM. An exemplary SLM comprise a high-resolution liquid crystal panel with micron-sized individually addressable pixels, which can be used to shape the wavefront of an optical beam. Grey-level values on the panel are converted into phase shifts. SLM can be used as programmable Fourier filters for generating contrast enhancement or as programmable diffractive optical elements for quantitative phase microscopy, in some embodiments.

The SLM can be programmed to generate various images during the training stage and/or during the inference stage of machine-learning models to improve the performance of the machine-learning models, as described herein.

During the inference stage of a trained machine-learning model, the SLM can be programmed to generate different input images for the trained machine-learning model. For example, the SLM can be programmed to generate input images for a trained image transformation model to obtain enhanced versions of the input images. The enhanced images can in turn be used for downstream operations. As another example, the SLM can be programmed to generate input images for a trained classification model to obtain more accurate classification results.

Further, the SLM can be programmed to generate different images as training data during the training stage of a machine-learning model. Further, SLM can be iteratively programmed, during either the training stage or the inference stage, to identify an optimal setting for capturing images that leads to the best performance of a given machine-learning model.

Accordingly, the SLM of the optical system can improve the performance of a machine-learning model via the training stage (e.g., by providing a rich training dataset) and/or via the inference stage (e.g., by providing input data under a variety of settings or the optimal setting). The SLM is programmed without requiring any mechanical movement or modifications to the optical system (e.g., a microscope). The SLM provides additional degrees of freedom to control the microscope. Multi focus acquisitions are possible without any mechanical movements, thus accelerating and improving the downstream tasks in an efficient manner.

Figure 9:
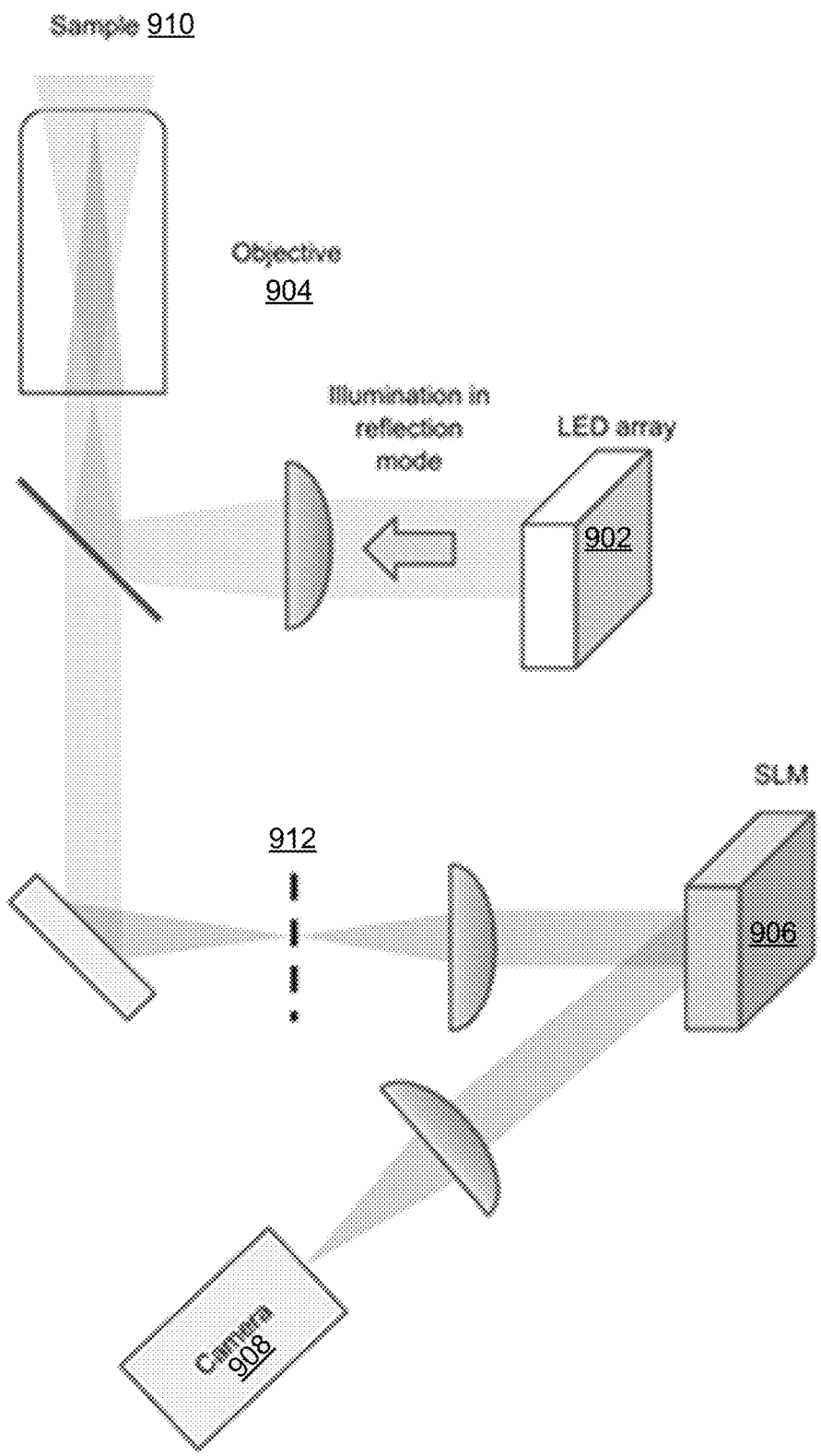
FIG. 9 illustrates an exemplary optical system, in accordance with some embodiments.

FIG. 9 illustrates an exemplary optical system, in accordance with some embodiments. An exemplary optical system comprises a light source 902 (e.g., an LED array), objective lens 904, an SLM 906, and a camera 908. The optical system has a reflection mode. In the reflection mode, the light source 902 provides illumination to a biological sample 910, which generates reflected light. The reflected light travels through the objective lens 904 and is captured by the camera 908.

With reference to FIG. 9, the dash line 912 indicates the intermediate image plane. As shown, the SLM is placed in the imaging path between the biological sample 910 and the camera 908. The SLM is configured to impose spatially varying modulations on the reflected light. For example, the SLM allows shaping of an alternative Fourier plane before the reflected light is focused on the camera 908.

In some embodiments, both the light source 902 and the SLM 906 can be programmable, thus allowing additional degrees of freedom to control and optimize the optical system without mechanically moving components of the optical system.

The configuration of the optical system in FIG. 9 is merely exemplary. One of ordinary skill in the art would appreciate that other configurations of the optical system can be used to place the SLM in the imaging path of the optical system to apply optimization techniques described herein.

Figure 10:
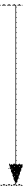
FIG. 10 illustrates an exemplary method for analyzing images of a biological sample using a programmable SLM of an optical system, in accordance with some embodiments.

FIG. 10 illustrates an exemplary method for analyzing images of a biological sample using a programmable SLM of an optical system, in accordance with some embodiments. Process 1000 is performed, for example, using one or more electronic devices implementing a software platform. In some examples, process 1000 is performed using a client-server system, and the blocks of process 1000 are divided up in any manner between the server and one or more client devices. In other examples, process 1000 is performed using only one or more client devices. In process 1000, some blocks are, optionally, combined, the order of some blocks is, optionally, changed, and some blocks are, optionally, omitted. In some examples, additional steps may be performed in combination with the process 1000. Accordingly, the operations as illustrated (and described in greater detail below) are exemplary by nature and, as such, should not be viewed as limiting.

At block 1002, an exemplary system (e.g., one or more electronic devices) obtains a plurality of images of the biological sample (e.g., sample 910 in FIG. 9). The plurality of images are generated using a plurality of configurations of an SLM of an optical system (e.g., SLM 906 in FIG. 9). The SLM is located in an optical path between the biological sample and an image recording device (e.g., camera 908).

In some embodiments, at least one configuration of the SLM is to generate one or more optical aberrations in the resulting image(s). The optical aberrations can include spherical aberration, astigmatism, defocus, tilt, or any combination thereof. In some embodiments, more information can be captured in and/or derived from images with optical aberrations. As an example, astigmatism allows collection of multi focus plane information in one image. As another example, defocus allows the system to scan a sample without any mechanical movements. An exemplary method of generating optical aberrations is provided in "Quantitative Phase Imaging and Complex Field Reconstruction by Pupil Modulation Differential Phase Contrast" by Lu et al., the content of which is incorporated by reference herein in its entirety.

In some embodiments, at least one configuration of the SLM is to enhance one or more features. The one or more features can comprise a cell border, an actin filament, nuclear shape, cytoplasm segmentation, or any combination thereof. In some embodiments, the system provides enhancement of neurites with specific convolution kernel encoded in the transfer function of the microscope. In some embodiments, the system provides enhancement of the response function of the microscope for certain liquid phase separated biological objects (protein, RNA, lipid). This enhancement would provide the capability to detect and characterize the composition of these objects. For example, using a helical phase pattern as phase filter in a Fourier plane gives rise to a doughnut-like point spread function. Convolution with an extended amplitude or phase-object leads to strong isotropic edge enhancement in the image. In a homogeneous (region of the) sample, destructive interference occurs because of the 7E phase shift across the doughnut (for any angle along the ring). Structure in the sample can give rise to less imperfect cancellation and thus to a local brightening in the image. Consequently the light is redistributed into edges and borderlines within the sample. Exemplary methods of enhancing features are provided in "Spiral phase contrast imaging in microscopy" by Fürhapter et al., "Shadow effects in spiral phase contrast microscopy" by Fürhapter et al., "Quantitative imaging of complex samples in spiral phase contrast microscopy" by Bernet et al., "Upgrading a microscope with a spiral phase plate" by Maurer et al., the content of which is incorporated by reference herein in their entirety.

In some embodiments, at least one configuration of the SLM is to reduce optical aberrations. For example, for live imaging and continuous monitoring of the cells, it is critical to reduce variability of the samples coming from the plates or debris in the wells. The SLM can allow these aberrations to be corrected. In some embodiments, the SLM can be used for iterative corrections of phase aberrations, e.g. based the Gerchberg-Saxton algorithm. For example, the dark center of a single optical vortex cam be used as a critical sensor for residual phase aberrations. Exemplary methods of enhancing features are provided in "Wavefront correction of spatial light modulators using an optical vortex image" by Jesacher et al. and "Phase contrast microscopy with full numerical aperture illumination" by Maurer et al., the content of which is incorporated by reference herein in their entirety.

In some embodiments, the plurality of SLM configurations is to obtain images of the biological sample at different depths. For example, the SLM allows for flexible image multiplexing, e.g., to combine images from different depths of the sample or for different settings of imaging parameters in one recorded image. Image multiplexing can facilitate quantitative phase microscopy. Imaging live sample has to be as fast as possible to minimize stress on the cells. Mechanical movements for 3D scanning of the samples are prohibitive. This system allows Fourier ptychography to be performed and reconstruction of large 3D volumes out of low resolution images of a whole well. Exemplary methods of multiplexing are provided in "Depth-of-field-multiplexing in microscopy" by Maurer et al., "Differential interference contrast imaging using a spatial light modulator" by McIntyre et al., and "Quantitative SLM-based differential interference contrast Imaging" by McIntyre et al., the content of which is incorporated by reference herein in their entirety.

In some embodiments, the system allows reconstruction of high-resolution images through optimized Fourier ptychography. Fourier ptychography is a computational imaging technique based on optical microscopy that includes the synthesis of a wider numerical aperture from a set of full-field images acquired using different optical settings, resulting in increased resolution compared to a conventional microscope. The images in an image set can be acquired using different configurations of the LED and/or the SLM; the acquired image set can then be combined using an iterative phase retrieval algorithm into a final high-resolution image that can contain up to a billion pixels (a gigapixel) with diffraction-limited resolution, resulting in a high space-bandwidth product.

A light source of the optical system can also be programmed. In some embodiments, the plurality of images at block 1002 are obtained using a plurality of configurations of the light source (e.g., light source 902) of the optical system. Exemplary methods for programming the light source are described herein, for example, with reference to FIGS. 1 and 2B.

Turning back to FIG. 10, at block 1004, the system inputs the plurality of images of the biological sample into a trained machine-learning model to obtain one or more outputs.

In some embodiments, the trained model is an image transformation model configured to generate, based on an input image of a first type, an output image of a second type (e.g., enhanced versions of the input images). In some embodiments, the enhanced versions of the input images comprise enhanced cellular phenotypes. In some embodiments, the trained model is a GAN model or a self-supervised model. For example, the trained model can be model 100 configured to receive bright-field images and generate fluorescence images.

In some embodiments, the trained model is a classification model configured to provide a classification output. For example, the model can receive an input image and detect one or more pre-defined objects in the input image, such as a diseased tissue.

FIG. 11 illustrates an exemplary method for training a machine-learning model, in accordance with some embodiments. Process 1100 is performed, for example, using one or more electronic devices implementing a software platform. In some examples, process 1100 is performed using a client-server system, and the blocks of process 1100 are divided up in any manner between the server and one or more client devices. In other examples, process 1100 is performed using only one or more client devices. In process 1100, some blocks are, optionally, combined, the order of some blocks is, optionally, changed, and some blocks are, optionally, omitted. In some examples, additional steps may be performed in combination with the process 1100. Accordingly, the operations as illustrated (and described in greater detail below) are exemplary by nature and, as such, should not be viewed as limiting.

At block 1102, an exemplary system (e.g., one or more electronic devices) obtains a plurality of images of a biological sample. The plurality of images are generated using a plurality of configurations of an SLM of an optical system (e.g., SLM 906 in FIG. 9). The SLM is located in an optical path between the biological sample and an image recording device (e.g., camera 908).

In some embodiments, the SLM configurations are configured to create desirable effects in the resulting images. As discussed above, some configurations of the plurality of configurations of the SLM can be to generate one or more optical aberrations (e.g., a spherical aberration, astigmatism, defocus, distortion, tilt, or any combination thereof), to enhance one or more features (e.g., a cell border, an actin filament, nuclear shape, cytoplasm segmentation, or any combination thereof), to reduce optical aberrations, to obtain images of the biological sample at different depths, etc.

At block 1104, the system trains the machine-learning model using the plurality of images. In some embodiments, the trained model is an image transformation model configured to generate, based on an input image of a first type, an output image of a second type (e.g., enhanced versions of the input images). In some embodiments, the enhanced versions of the input images comprise enhanced cellular phenotypes. In some embodiments, the trained model is a GAN model or a self-supervised model. For example, the trained model can be model 100 configured to receive bright-field images and generate fluorescence images. Exemplary methods of training the model are described herein with reference to FIGS. 2A-B and 3A-3D.

In some embodiments, the trained model is a classification model configured to provide a classification output. For example, the model can receive an input image and detect one or more pre-defined objects in the input image, such as a diseased tissue. Training of the classification model can be performed using the plurality of images and associated labels.

In some embodiments, at block 1104, the SLM can be iteratively programmed to identify an optimal SLM configuration for capturing images that lead to an improved performance of a given machine-learning model. Specifically, at block 1106, the system trains the machine-learning model using a first image, where the first image is obtained using a first configuration of the SLM of the optical system. At block 1108, the system evaluates the trained machine-learning model. At block 1110, the system, based on the evaluation, identifying a second configuration of the SLM. At block 1112, the system trains the machine-learning model using a second image, wherein the second image is obtained using the second configuration of the SLM of the optical system.

For example, at block 1106, the system trains the model using images corresponding to a first set of SLM configurations. Each image results in a corresponding loss based on a loss function of the model. At block 1108, the system determines which SLM configuration of the first set of SLM configurations results in the smallest loss (e.g., generator loss). At block 1110, the SLM configuration that has produced the smallest loss can be identified and a new second set of SLM configurations can be identified accordingly. For example, the new set of SLM configurations can include the best SLM configuration (i.e., the configuration that produced the smallest loss) from the first set and/or one or more new SLM configurations similar to the best SLM configuration.

The new set of SLM configurations can also exclude SLM configurations that have resulted in the biggest loss from the first set. The new set of SLM configurations can be loaded onto the optical system to obtain additional training data. This steps can be repeated until a threshold is met, for example, when no more improvement (e.g., on the generator loss) is observed. The optimal SLM configuration can be stored and used to obtain input images.

While steps 1106-1112 are described as part of a training process, they can be performed in other stages of the pipeline (e.g., inference stage) to identify the optimal SLM configuration for generating input images. In some embodiments, the light source and the SLM of the optical system can be iteratively programmed together to identify the best combination of illumination pattern and SLM configuration for generating input images.

While FIGS. 9-11 describes optimization techniques using an SLM component of an optical system, it should be appreciated the SLM can be replaced with another hardware component that can alter the optical function (e.g., pupil function) of the system, such as micro-mirrors, without departing from the spirit of the invention.

Figure 12C:
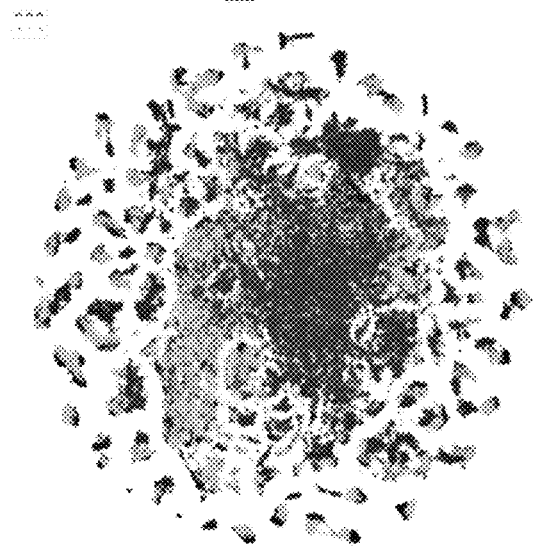
FIGS. 12C and 12D illustrate a side-by-side comparison of the same classification results in FIGS. 9A and 9B, respectively, with a different color scheme to show the two models' resistance to batch effects, in accordance with some embodiments.
Figure 12D:
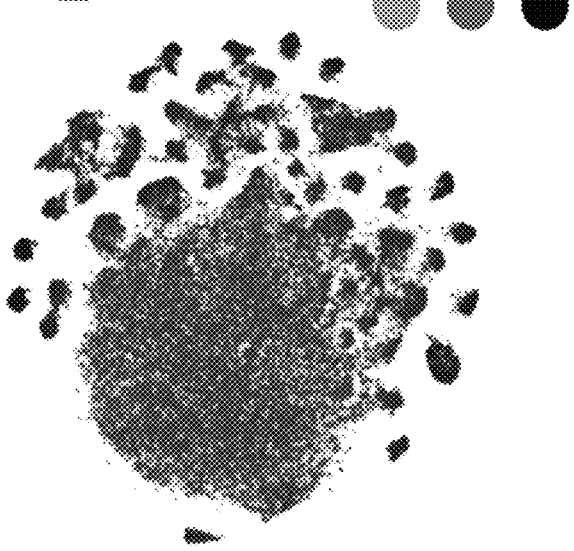
Figure 12A:
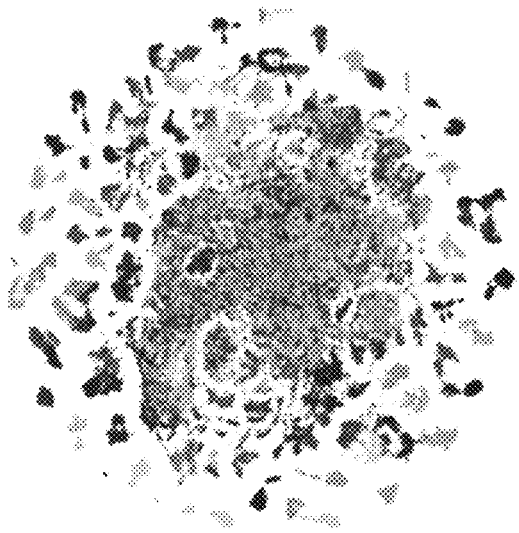
FIGS. 12A and 12B illustrate a side-by-side comparison of classification results of two classification models based on the same input images, in accordance with some embodiments.
Figure 12B:
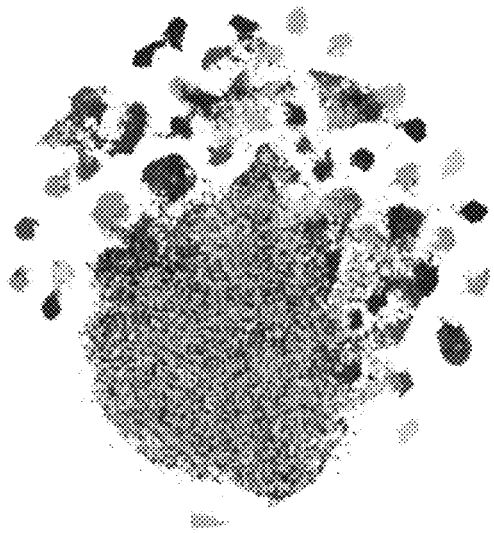

FIGS. 12A and 12B illustrate a side-by-side comparison of classification results of two classification models, in accordance with some embodiments. The classification model in FIG. 12A is trained using real images captured by a microscope (e.g., real fluorescence images), while the classification model in FIG. 12B is trained using synthetic images generated using the techniques described herein (e.g., fluorescence images generated from bright-field images). The classification models determines which chemical compound that tissues depicted in an input image have responded to. Specifically, each model is configured to receive an input image and output a classification result indicative of one of 150 predefined chemical compounds. In the depicted example, each of FIGS. 12A and 12B shows a Uniform Manifold Approximation and Projection (UMAP) in which each input image is represented as a point in the UMAP. The color of the point represents the chemical compound the image is classified as by the classification model. In some embodiments, the input images into the model in FIG. 12A are real images, while the input images into the model in FIG. 12B are generated images.

Figure 12E:
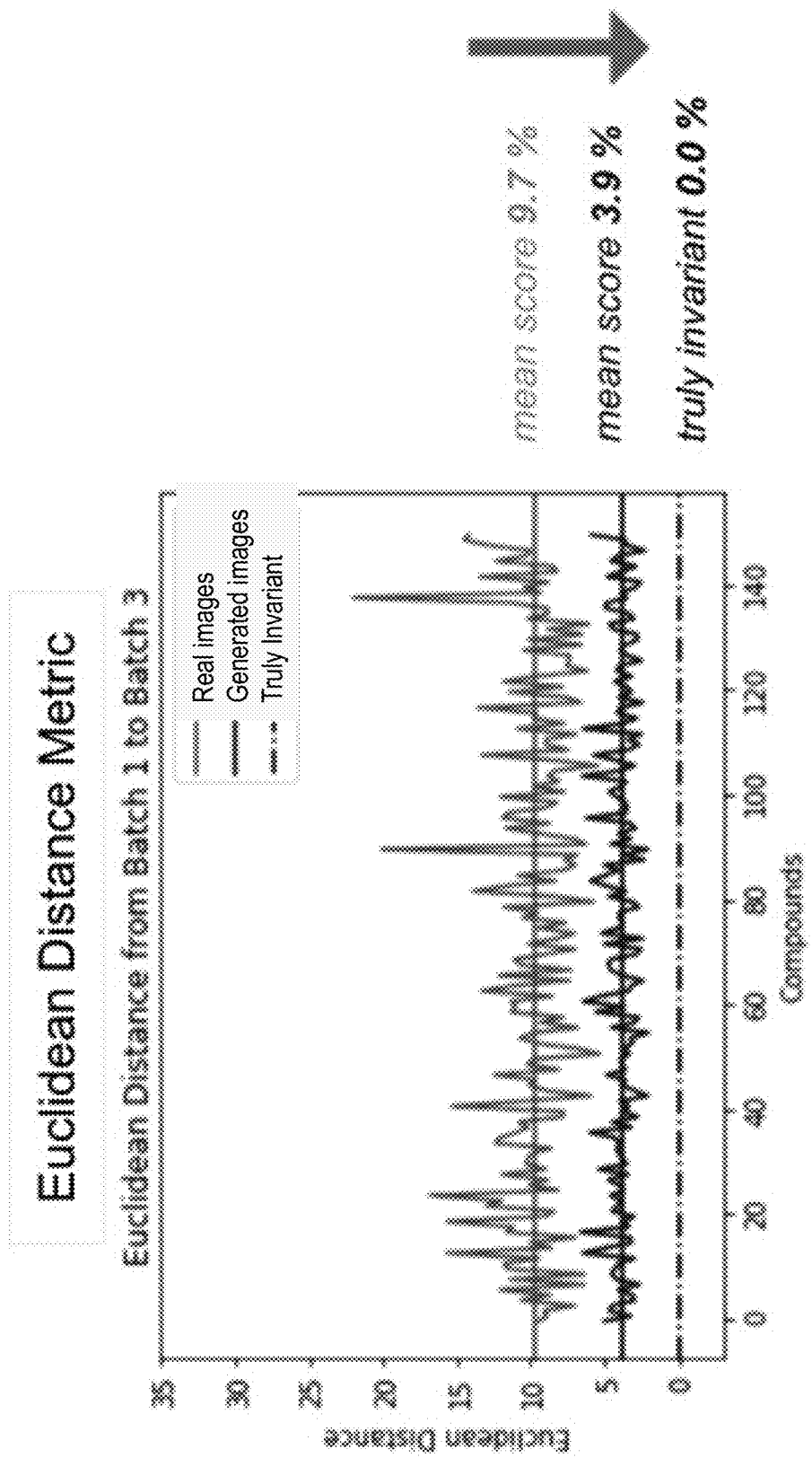
FIG. 12E illustrates the Euclidean distance metric corresponding to a real image set, a generated image set, and a truly batch-invariant image set, in accordance with some embodiments.

FIGS. 12C and 12D illustrate a side-by-side comparison of the same classification results in FIGS. 12A and 12B, respectively, with a different color scheme to demonstrate the two models' resistance to batch effects. Batch effects refer to situations where subsets (i.e., batches) of data significantly differ in distribution due to irrelevant, instrument-related factors. Batch effects are undesirable because they introduce systematic errors, which may cause downstream statistical analysis to produce spurious results and/or obfuscate the signal of interest. In each of FIGS. 12C and 12D, the input images belong to three different batches (e.g., from different plates or experiments), as indicated by different grey levels. As shown, FIG. 12D shows a greater overlap among the points corresponding to the three batches, indicating that the generated images are more resistance to batch effects. FIG. 12E illustrates the Euclidean distance metric corresponding to a real image set (e.g., input images as shown in FIGS. 12A and 12C), a generated image set (e.g., input images as shown in FIGS. 12B and 12D), and a truly batch-invariant image set. The Euclidean distance metric for each image set measures the Euclidean distance between the image embeddings from two separate batches (e.g., Real Image Batch 1 and Real Image Batch 3 in FIG. 12C, Generated Image Batch 1 and Generated Image Batch 3 in FIG. 12D). For a truly batch-invariant image set, the mean score should be 0 (i.e., no batch effects). As shown, the mean score for the generated image set is lower than the mean score for the real images, thus demonstrating superior batch invariance.

Figure 13C:
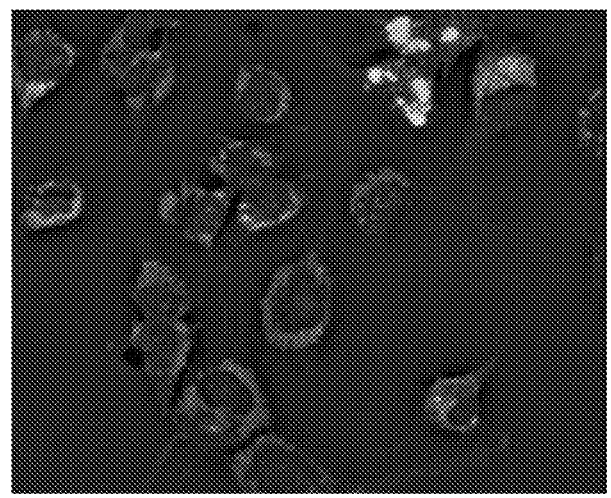
FIG. 13C illustrates an exemplary generated image, in accordance with some embodiments.
Figure 13B:
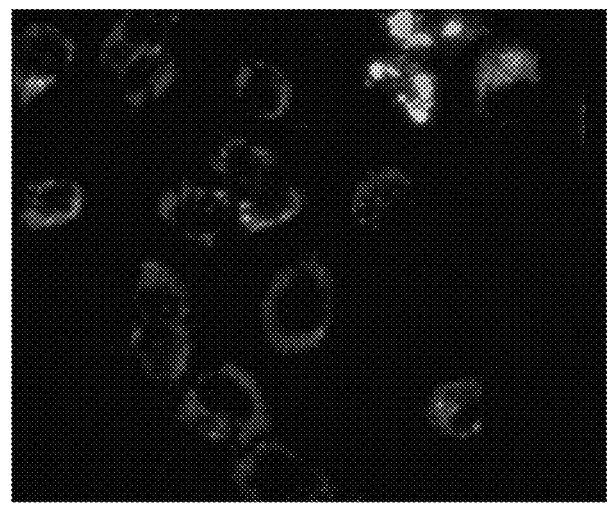
FIG. 13B illustrates an exemplary generated image, in accordance with some embodiments.
Figure 13A:
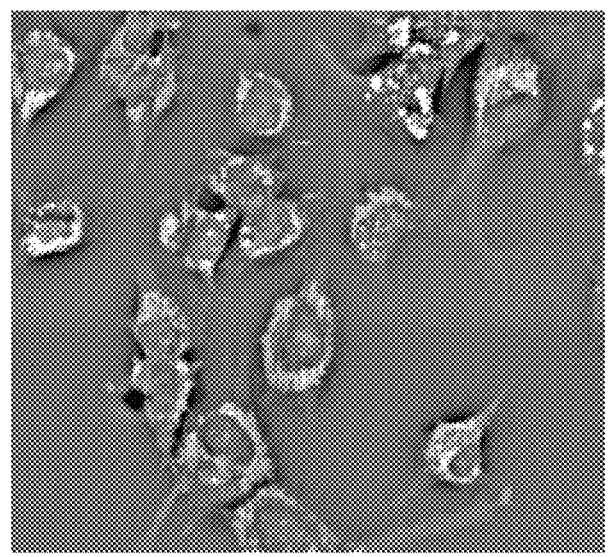
FIG. 13A illustrates an exemplary generated image, in accordance with some embodiments.

FIGS. 13A and 13B illustrate an exemplary generated phase image and an exemplary generated fluorescence image, in accordance with some embodiments. FIG. 13A is a phase image generated by a GAN model described herein, for example, from a bright-field image. FIG. 13B is a fluorescence/bodipy image generated by the GAN from the same bright-field image. The bodipy image includes a virtual green hue to highlight the presence of a biomarker. FIG. 13C shows FIG. 13B overlaid onto the phase image in FIG. 13A. Thus, the GAN model can be used for disease modeling. For example, multiple samples can be obtained and imaged from a subject. The resulting series of bright-field images can be analyzed by the GAN model to generate synthetic phase and fluorescence images to study disease perturbations.

Figure 14A:
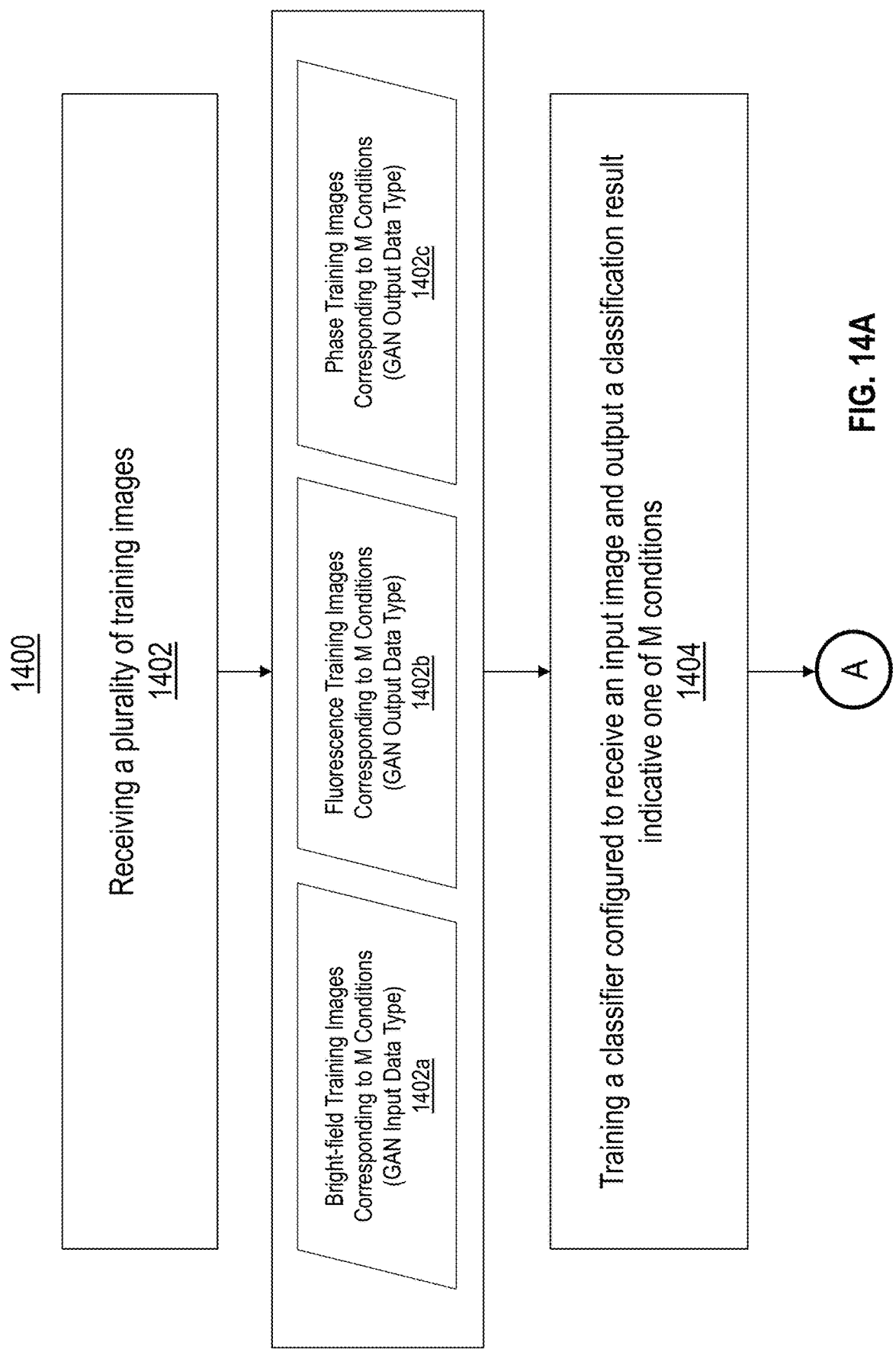

FIGS. 14A-B illustrate an exemplary process for training a machine-learning model (e.g., a GAN model) configured to generate synthetic data (e.g., image data) and identifying an optimal illumination scheme for obtaining input data for the machine-learning model, in accordance with some embodiments. Process 1400 is performed, for example, using one or more electronic devices implementing a software platform. In some examples, process 1400 is performed using a client-server system, and the blocks of process 1400 are divided up in any manner between the server and one or more client devices. In other examples, process 1400 is performed using only one or more client devices. In process 1400, some blocks are, optionally, combined, the order of some blocks is, optionally, changed, and some blocks are, optionally, omitted. In some examples, additional steps may be performed in combination with the process 1400. Accordingly, the operations as illustrated (and described in greater detail below) are exemplary by nature and, as such, should not be viewed as limiting.

At block 1402, an exemplary system (e.g., one or more electronic devices) receives a plurality of training images. The plurality of training images are real images of biological samples and are also referred to as the ground truth data. The plurality of training images comprises the type of image data that the GAN model is configured to receive and the type(s) of image data that the GAN model is configured to output. For example, if the GAN model is configured to receive a bright-field image and output a fluorescence image and a phase image, the received plurality of images would include a plurality of bright-field training images 1402a (i.e., a GAN input data type), a plurality of fluorescence training images 1402b (i.e., a GAN output data type), and a plurality of phase training images (i.e., a GAN output data type).

The bright-field training images in the plurality 1402a can be captured by illuminating in vitro (or biopsy) cell samples with an inexpensive LED array using different illumination settings. The fluorescence training images in the plurality 1402b can be captured after a dye is applied to the biological sample (e.g., to enhance the visibility of a biomarker). The phase training images can be obtained using physics- or optics-based models. It should be appreciated by one of ordinary skill in the art that the plurality of training images used in the process 1400 can differ depending on the type of the image data that the GAN is configured to receive and output. In some embodiments, the plurality of training images comprises paired image data. For example, a bright-field image, a fluorescence image, and a phase image of the same biological sample can be included in the sets 1402a, 1402b, and 1402c, respectively.

In some embodiments, the plurality of training images are acquired to enable training of the GAN model such that the synthetic images (e.g., synthetic fluorescence images, synthetic phase images) generated by the GAN model will provide the same performance in downstream analyses as real images (e.g. real fluorescence images, real phase images). In some embodiments, the downstream analyses include a classification task that classifies an image as corresponding to one class out of M classes. For example, the classification task can involve classifying an image as corresponding to a particular cell state out of multiple cell state classes (e.g., healthy state, diseased state). As another example, the classification task can involve classifying an image as corresponding to a particular perturbation out of multiple perturbation classes. In order to train the GAN model to generate synthetic images that can be classified as accurately as the real images, the training images include images corresponding to the M classes (or conditions). For example, if the M classes include a healthy cell state class and a diseased cell state class, the plurality of bright-field training images 1402a can include bright-field images depicting healthy cells and bright-field images depicting diseased cells, the plurality of fluorescence training images 1402b can include fluorescence images depicting healthy cells and fluorescence images depicting diseased cells, and the plurality of phase training images 1402c can include phase images depicting healthy cells and phase images depicting diseased cells. For example, if the M classes include M perturbations, the plurality of bright-field training images 1402a can include bright-field images depicting the M perturbations, etc. Each training image can be labelled with the corresponding condition. For example, a phase image depicting a diseased cell state can be associated with a diseased label.

In an exemplary implementation, the plurality of training images includes X fields of view per condition. i.e., M×X fields of view in total. Specifically, in the plurality of bright-field images 1402a, each field of view includes N bright-field images captured using N illumination settings, thus resulting in M×X×N bright-field images in total. In the plurality of fluorescence images 1402b, each field of view includes one fluoresce image, thus resulting in M×X fluorescence images in total. In the plurality of phase images 1402c, each field of view includes one phase image, thus resulting in M×X phase images in total. In some embodiments, the bright-field images are at magnification=$m_{in}$, while the fluorescence images are at magnification $m_{out} \geq m_{in}$ and the phase images are at $m_{out} \geq m_{in}$.

At block 1404, the system trains a classifier configured to receive an input image and output a classification result indicative of one of M conditions. For example, if the M conditions include a healthy condition and a diseased condition, the classifier is configured to receive an input image and output a classification result indicative of either the healthy condition or the diseased condition. After the classifier is trained, it is used during the training of the GAN model to ensure that the GAN model can generate synthetic image data that can be classified to the same or similar level of accuracy as real image data, as described below.

In some embodiments, the classifier is trained using the same type of image data that the GAN model is configured to output. In the depicted example in FIGS. 14A and 14B, the GAN model is configured to output a fluorescence image and a phase image; thus, the classifier trained in block 1404 is trained using the plurality of fluorescence training images 1402b and the plurality of phase training images 1402c. During training, each fluorescence image or phase image is inputted into the classifier to obtain a predicted classification result (e.g., healthy or diseased). The predicted classification result is then compared against the actual class associated with the training image (e.g., whether training image in fact depicts a healthy cell state or diseased cell state) and, based on the comparison, the classifier can be updated accordingly. The classifier can be implemented using any classification algorithm, such as a logistic regression model, a naïve Bayes model, a decision tree model, a random forest model, a support vector machine model, etc.

At block 1406, the system trains the GAN model based on the training images. Block 1406 can include steps 1408a-1408e, which can be repeated until the training is complete (e.g., when convergence is reached). The steps 1408a-e are described below with reference to FIG. 15, which is a schematic diagram illustrating the steps, in accordance with some embodiments.

Figure 15:
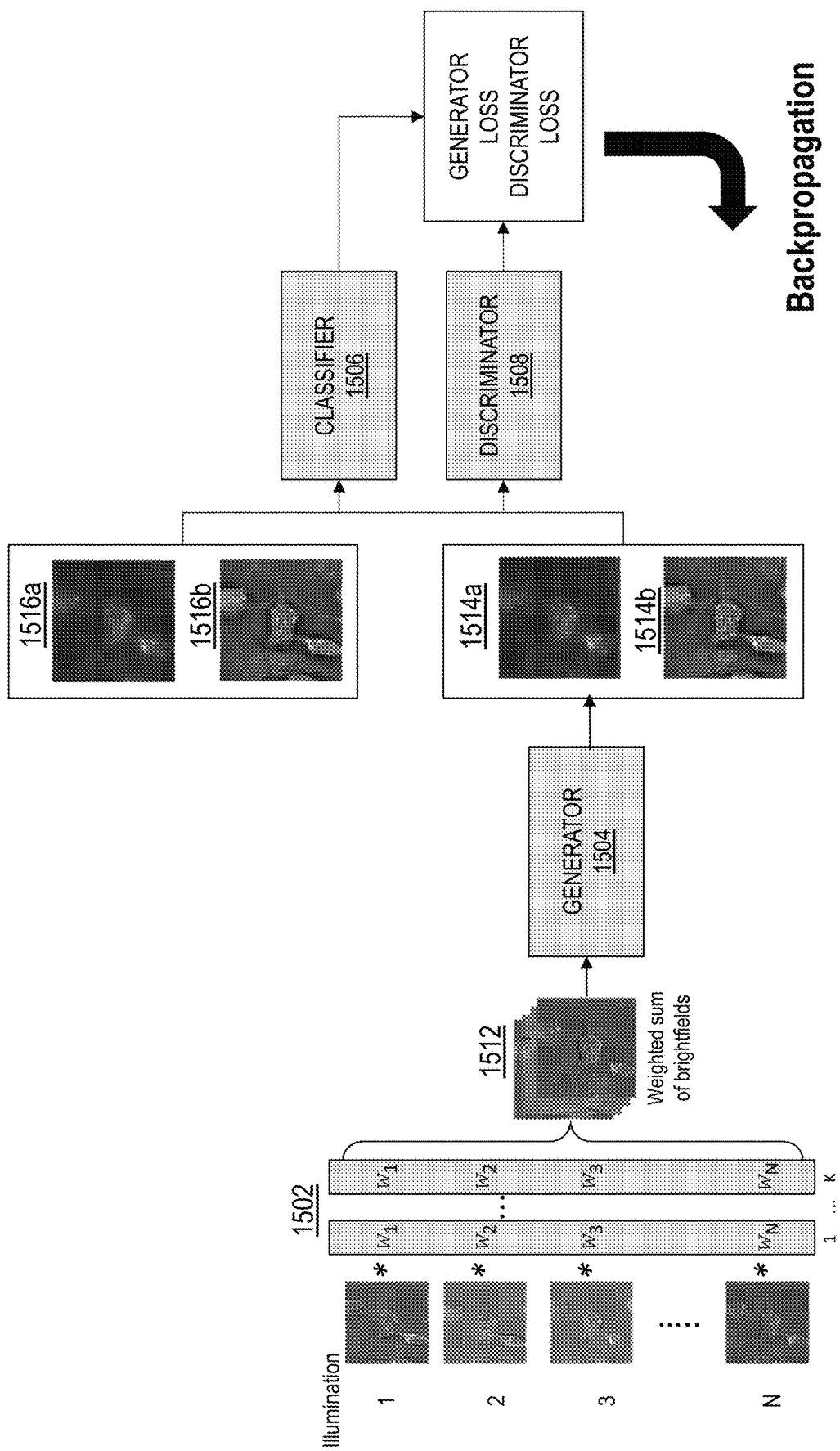
FIG. 15 illustrates a schematic diagram for training a machine-learning model, in accordance with some embodiments.

As shown in FIG. 15, the GAN model includes a multi-head attention layer 1502 comprising a matrix of weights, specifically, K sets of weights $w_1$-$w_n$, a generator 1504, a discriminator 1508, and the trained classifier 1506 from block 1404. During training of the GAN model, the classifier remains fixed while the generator, the discriminator, and the attention layer are updated, as described below.

At block 1408a, the system applies each of K sets of weights in the attention layer of the GAN model to a set of bright-field training images. The set of bright-field training images are obtained from the plurality of bright-field images 1402a. In some embodiments, the set of bright-field training images correspond to the same field of view and depict the same biological sample, but are captured using different illumination settings. For example, if a LED array comprises N illumination emitters (e.g., LEDs), each illumination emitter can be turned on one at a time and a bright-field image of the biological sample illuminated by each illumination emitter can be captured, thus resulting in a set of N bright-field training images.

In the depicted example in FIG. 15, the system receives a set of N bright-field training images corresponding to illumination settings 1-N. For example, the first bright-field image depicts the biological sample being illuminated using the illumination setting 1 (e.g., only the first LED in the array is turned on), the second bright-field image depicts the biological sample being illuminated using the illumination setting 2 (e.g., only the second LED in the array is turned on), . . . and the N-th bright-field image depicts the biological sample being illuminated using the illumination setting N (e.g., only the N-th LED in the array is turned on).

The attention layer generates K sets of weights and each set comprises N weights. Each set of weights $w_1$-$w_n$ is applied to the N images to generate an aggregated image. For each set of weights, the attention layer 1502 assigns a continuous weight (e.g., a normalized scalar weight) in the set to each of the set of bright-field training images. These weights correspond to intensity values of the corresponding illumination settings (e.g., the corresponding LEDs). As shown, $w_1$ is applied to (e.g., multiplied with) the first bright-field image, $w_2$ is applied to the second bright-field image, $w_n$ is applied to the N-th bright-field image. After the weights are applied, the weighted images can be aggregated (e.g., summed) to obtain one aggregated bright-field image. Because there are K sets of weights, K aggregated images 1512 can be generated. In some embodiments, the attention layer is an adapted multi-head attention layer. The attention mechanism allows the natural generation of K linear combination of bright-field images (i.e., aggregated images). These aggregated images are fed to the rest of the network as described herein.

At block 1408*b*, the system inputs each of the aggregated bright-field images into the GAN model. With reference to FIG. 15, each of the aggregated bright-field images 1512 is inputted into the generator 1504, which outputs a synthetic fluorescence image 1514*a* and a synthetic phase image 1514*b*. The generator can be implemented in a similar manner as the generator described above with reference to FIGS. 3A-D.

During training, the generator output (i.e., the generated fluorescence image 1514*a* and the generated phase image 1514*b*) can be connected directly to the discriminator input. The discriminator 1508 is trained to distinguish generated images and real images. During training, a generated image can be inputted into the discriminator 1508 to obtain a discriminator loss and a generator loss as described above. Further, a real image can also be inputted into the discriminator 1508 to generate a discriminator loss and a generator loss. The real image can be the real fluorescence image 1516*a* (from the plurality of fluorescence training images 1402*b* in FIG. 14A) corresponding to the same field of view as the input bright-field images, or the real phase image 1516*b* (from the plurality of phase training images 1402*c* in FIG. 14A) corresponding to the same field of view as the input bright-field images.

In some embodiments, the discriminator loss function is a Wasserstein discriminator loss and calculated as follows:

$$\nabla_w \frac{1}{m}\sum_{i=1}^{m}[f(x^{(i)}) - f(G(z^{(i)}))]$$

where f(x) is the discriminator's output based on wavelet coefficients of a real fluorescence or phase image, w is the model weights of the discriminator, m is the size of the mini-batch, f is the discriminator model, x is the real image, z is the input (bright-field image 1512), G is the generator model, and f(G(z)) is the discriminator's output based on the predicted wavelet coefficients corresponding to a synthetic fluorescence or phase image.

In some embodiments, the generator loss function is a Wasserstein generator loss and calculated as follows:

$$\nabla_\theta \frac{1}{m}\sum_{i=1}^{m}[f(G(z^{(i)}))]$$

where f(x) is the discriminator's output based on wavelet coefficients of a real fluorescence or phase image, m is the size of the mini-batch, f is the discriminator model, z is the input (bright-field image 1512), G is the generator model, and f(G(z)) is the discriminator's output based on the predicted wavelet coefficients.

At block 1408*c*, the system inputs each generated image and a real image corresponding to the generated image into the trained classifier to obtain a classifier loss. For example, the generated fluorescence image 1514*a* is inputted into the classifier 1506 to obtain a first classification result; the real fluorescence image 1516*a* is inputted into the classifier 1506 to obtain a second classification result; a classifier loss can be calculated based on the difference between the first classification result and the second classification result. As another example, the generated phase image 1514*b* is inputted into the classifier 1506 to obtain a third classification result; the real phase image 1516*b* is inputted into the classifier 1506 to obtain a fourth classification result; a classifier loss can be calculated based on the difference between the third classification result and the fourth classification result.

At block 1408*d*, the system augments the generator loss based on the classifier loss. For example, the generator loss can be augmented with a L2 norm of the classification score from the real images. In some embodiments, if no classifier is available or no classification is wanted, the classifier loss is replaced by a constant (e.g. 0).

At block 1408*e*, the system updates the GAN model based on the augmented generator loss. The backpropagation follows the same procedure as described above. The discriminator updates its weights through back-propagation based on the discriminator loss through the discriminator network. Further, the augmented generator loss is back-propagated to update the weights in the attention layer (e.g., the weights with which the aggregated image is calculated) and the generator. For example, the generated loss calculated based on an aggregated image corresponding to the K-th set of weights can be used to update the K-th set of weights in the attention layer.

At block 1410, the system obtains one or more optimal illumination patterns based on the weights in the attention layer of the trained GAN model. As described above, the weights in the attention layer (e.g., $w_1$-$w_n$) can be indicative of the intensity values of the corresponding illumination settings (e.g., the corresponding LEDs in the LED array). As discussed above, the attention layer can be a multi-head attention layer that provide K sets of weights (i.e., K linear combinations), thus resulting in K illumination patterns.

In some embodiments, before the block 1406, the generator and the discriminator of the GAN model are pre-trained using bright-field images in which all LEDs in the LED array are turned on. After the pre-training, block 1406 is performed to update the attention weights while the generator and the discriminator remain fixed. The optimal combination of the illuminations can be obtained based on the updated weights.

FIG. 16A illustrates synthetic images generated by an exemplary GAN model to study the NASH disease, in accordance with some embodiments. In the depicted example, Hepg2 cells with NASH genetic background are illuminated using an optimal illumination pattern identified using techniques described herein, and a bright-field image is captured. The bright-field image is inputted into a GAN model, which outputs a generated phase image and a generated fluorescence/bodipy image in FIG. 16A. The GAN model used in FIG. 16A can be configured to include a trained classifier as described with reference to FIGS. 14A-B and 15. The classifier has two conditions: a healthy condition (e.g., no perturbations) and a diseased condition (e.g., inflammation cocktail plus fatty acid). As described, the GAN model can be trained such that the generated images can be classified by the classifier to the same or similar degree of accuracy as real images.

The synthetic images generated by the GAN model can be used to create disease models. FIG. 16B illustrates downstream analyses of the generated images, in accordance with some embodiments. As shown, the generated images can be used to perform nucleus segmentation and blob detection (e.g., using image-processing algorithms). Thus, the generated images can be used to create a disease model for the NASH disease and study chemical perturbations in NASH.

The synthetic images generated by the GAN model can also be used to evaluate the efficacy of a treatment. The system processes three groups of generated images: a first group of images depicting healthy tissues that do not have the disease, a second group of images depicting untreated diseased tissues, and a third group of images depicting diseased tissues that have been treated (e.g., using a particular drug). In the depicted example in FIG. 16C, the first group of images (labelled "untreated") comprises images of healthy tissues that do not have the non-alcoholic steatohepatitis (NASH) disease, the second group of images (labelled "NASH 2X") comprises images of untreated tissues having the NASH disease, and the third group of images (labelled "NASH 2X+ACC inhibitor") comprise images of tissues with NASH that have been treated with a drug (e.g., 50 uM ACC inhibitor or firsocostate). In some embodiments, the three groups of images capture tissues of the same subject at different times. In some embodiments, the three groups of images capture tissues of different subjects. The images can be phase images or fluorescence images generated using the techniques described herein (e.g., from bright-field images). Each phase or fluorescence image can be generated based on multiple bright-field images and thus comprises richer information such as phase shift information. Accordingly, the generated phase or fluorescence images can allow for higher precision in downstream analyses, as described below.

Specifically, to evaluate the efficacy of the drug, the system generates a distribution for each group of images to determine whether the distributions reflect an effect of the drug on the disease state. In FIG. 16C, three probability distributions are generated using a classifier trained on generated images. The X-axis indicates the probability outputted by the classifier upon receiving an input image (e.g., a generated phase image). As shown by the three distributions, generated images of healthy tissues (i.e., distribution 1620) are generally classified as having lower probabilities of having the disease than generated images of the diseased tissues (i.e., distribution 1624). Further, generated images of treated tissues (i.e., distribution 1622) are generally classified as having lower probabilities of having the disease than generated images of diseased tissues. A comparison of these distributions may indicate that the drug is effective at reversing or reducing the disease state, because the treatment has caused the diseased tissues to include features more similar to the healthy state and less similar to the diseased state. Thus, the synthetic images can enable biophysics understanding of the distribution of lipids in the cells and provide insight for treatment.

Figure 16D:
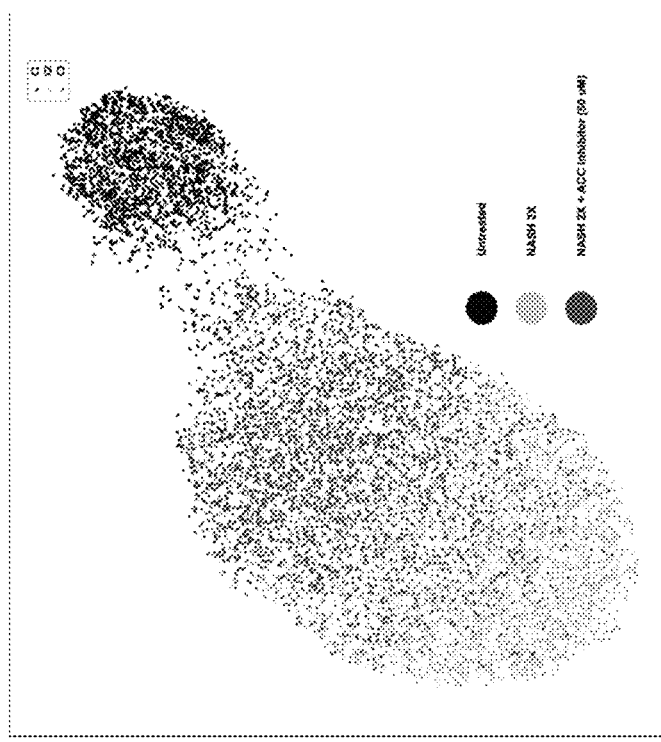
FIG. 16D illustrates an exemplary process for evaluating a candidate treatment, in accordance with some embodiments.
Figure 16C:
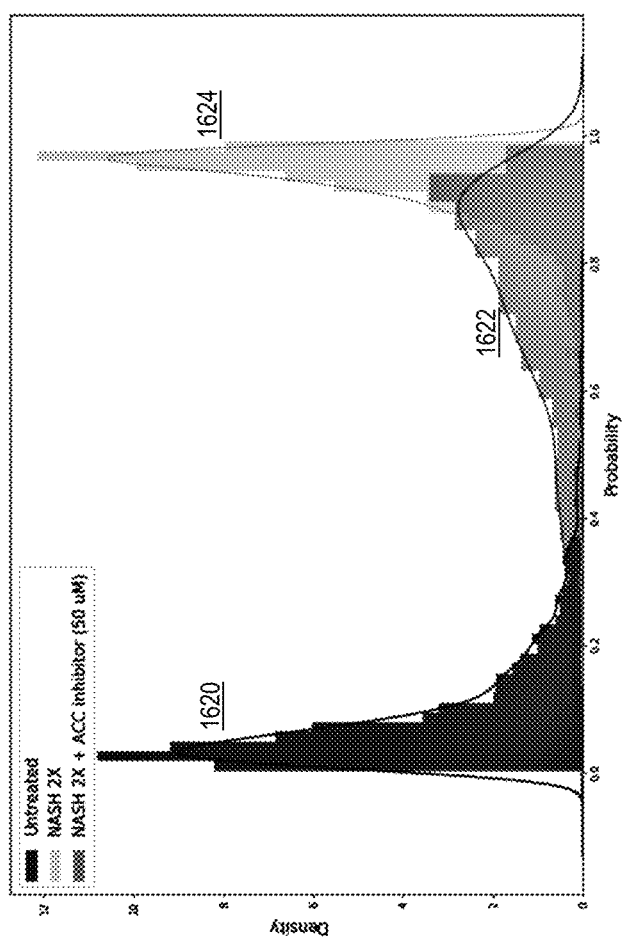
FIG. 16C illustrates an exemplary process for evaluating a candidate treatment, in accordance with some embodiments.

In some embodiments, rather than using distributions, the system can identify image clusters in an embedding space (e.g., UMAP), as shown in FIG. 16D. In the UMAP, each point represents an image embedding of an image (e.g., a generated phase image). As shown, the generated images of treated tissues form a cluster that moves away from the cluster of generated diseased images and toward the cluster of generated healthy images, which may indicate that the drug is effective at reversing or reducing the disease state.

The analysis in FIGS. 16C and 16D can applied to evaluate a plurality of drug candidates with respect to a disease of interest. For example, tissues treated by each drug candidate can be imaged, for example, by a microscope, to obtain bright-field images. The bright-field images can be transformed into phase images using the techniques described herein. Distribution or cluster can be generated for phase images of each treatment. Accordingly, the resulting plot can comprise a distribution or cluster representing the disease state, a distribution or cluster representing the health state, and a plurality of distributions or clusters each representing a candidate drug. The system can then identify the distribution or cluster closest to the healthy state to identify the most effective candidate drug candidate.

Figure 17A:
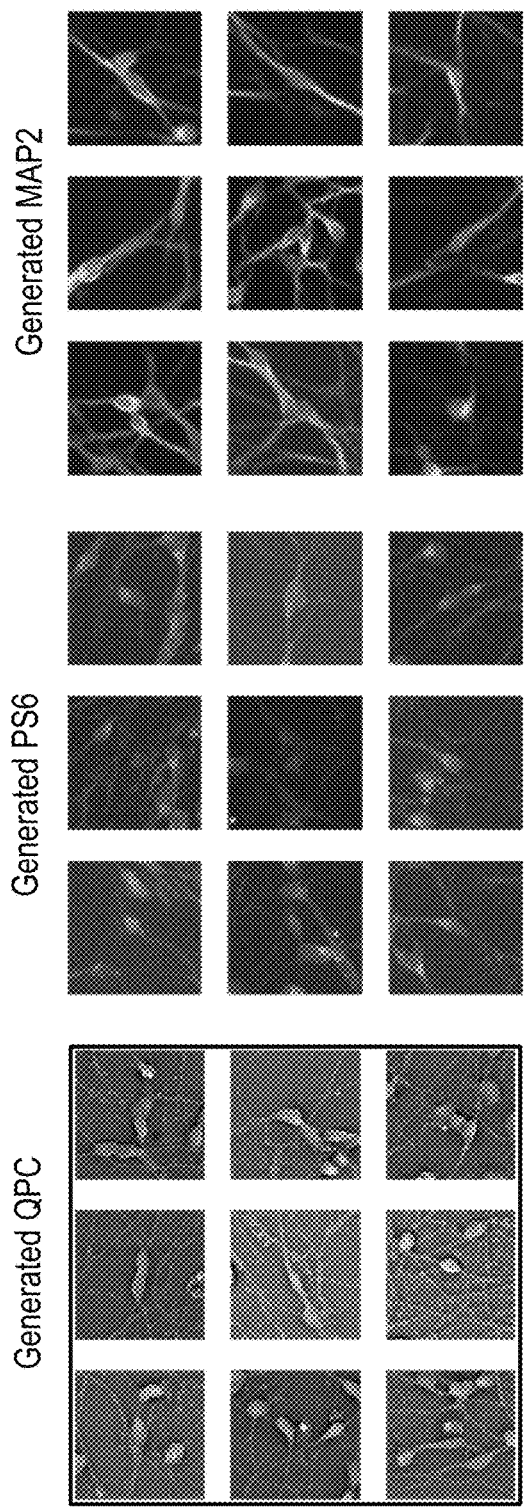
FIG. 17A illustrates synthetic images generated by an exemplary GAN model to study tuberous sclerosis ("TSC"), in accordance with some embodiments

FIG. 17A illustrates synthetic images generated by an exemplary GAN model to study tuberous sclerosis ("TSC"), in accordance with some embodiments. In the depicted example, NGN2 neurons are illuminated using an optimal illumination pattern identified using techniques described herein, and bright-field images are captured. The bright-field images are inputted into a GAN model, which outputs generated phase images and generated fluorescence/bodipy images in FIG. 17A. The GAN model used in FIG. 17A can be configured to include a trained classifier as described with reference to FIGS. 14A-B and 15. The classifier has 2 conditions: a healthy condition (e.g., wild type) and a diseased condition (e.g., TSC KO). As described, the GAN model can be trained such that the generated images can be classified by the classifier to the same or similar degree of accuracy as real images.

The synthetic images generated by the GAN model can also be used to evaluate the efficacy of a treatment. The system processes three groups of generated images: a first group of images depicting healthy tissues that do not have the disease, a second group of images depicting untreated diseased tissues, and a third group of images depicting diseased tissues that have been treated (e.g., using a particular drug). In the depicted example in FIG. 17B, the first group of images (labelled "Wildtype") comprises images of healthy tissues that do not have the TSC disease, the second group of images (labelled "TSC") comprises images of untreated tissues having the TSC disease, and the third group of images (labelled "TSC+Rapamycin") comprise images of tissues with TSC that have been treated with a drug. In some embodiments, the three groups of images capture tissues of the same subject at different times. In some embodiments, the three groups of images capture tissues of different subjects. The images are phase images generated using the techniques described herein (e.g., from bright-field images).

Figure 17B:
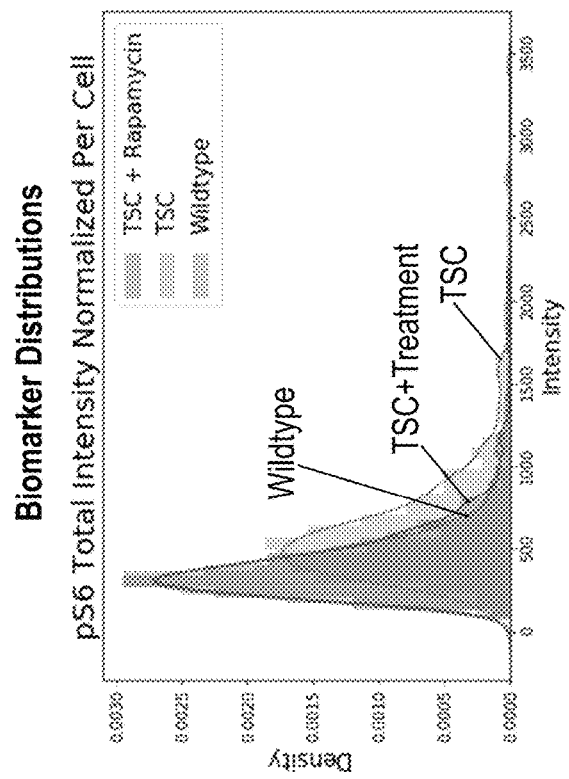
FIG. 17B illustrates an exemplary process for evaluating a candidate treatment, in accordance with some embodiments.

Specifically, to evaluate the efficacy of the drug, the system generates a distribution for each group of images to determine whether the distributions reflect an effect of the drug on the disease. In FIG. 17B, three biomarker distributions are generated. As shown by these distributions, the drug appears to be effective at reversing or reducing the disease state, because the treatment has caused the diseased tissues to include features more similar to the healthy state and less similar to the diseased state. The analysis in FIG. 17B can applied to evaluate a plurality of drug candidates with respect to a disease of interest, as described above.

Exemplary methods, non-transitory computer-readable storage media, systems, and electronic devices are set out in the following items:

1. A method for training a machine-learning model to generate images of biological samples, comprising:
   obtaining a plurality of training images comprising:
     a training image of a first type, and
     a training image of a second type;
   generating, based on the training image of the first type, a plurality of wavelet coefficients using the machine-learning model;
   generating, based on the plurality of wavelet coefficients, a synthetic image of the second type;
   comparing the synthetic image of the second type with the training image of the second type; and updating the machine-learning model based on the comparison.
2. The method of item 1, wherein the training image of the first type is a bright-field image of a biological sample.
3. The method of item 2, wherein the training image of the second type is a fluorescence image of the biological sample.
4. The method of any of items 1-3, wherein the machine-learning model comprises a generator and a discriminator.
5. The method of item 4, wherein the machine-learning model comprises a conditional GAN model.
6. The method of any of items 4-5, wherein the generator comprises a plurality of neural networks corresponding to a plurality of frequency groups.
7. The method of item 6, wherein each neural network of the plurality of neural networks is configured to generate wavelet coefficients for a respective frequency group.
8. The method of any of items 6-7, wherein the plurality of neural networks comprises a plurality of U-Net neural networks.
9. The method of any of items 5-8, wherein the discriminator is a PatchGAN neural network.
10. The method of any of items 1-9, further comprising: generating, based on the training image of the first type, an image of a third type.
11. The method of item 10, wherein the image of the third type is a phase shift image.
12. The method of any of items 1-11, further comprising: generating, based on the training image of the first type, an image of a fourth type.
13. The method of item 12, wherein the image of the fourth type comprises segmentation data.
14. The method of any of items 1-13, wherein the training image of the first type is captured using a microscope according to a first illumination scheme.
15. The method of item 14, wherein the first illumination scheme comprises one or more illumination patterns.
16. The method of any of items 14-15, wherein the training image of the first type is part of a bright-field image array.
17. The method of any of items 14-16, wherein the plurality of training images is a first plurality of training images, the method further comprising:
based on the comparison, identifying a second illumination scheme;
obtaining a second plurality of training images comprising one or more images of the first type, wherein the one or more images of the first type are obtained based on the second illumination scheme;
training the machine-learning model based on the second plurality of training images.
18. The method of any of items 1-16, further comprising:
obtaining, using a microscope, a plurality of images of the first type; and
generating, based on the obtained plurality of images, a plurality of synthetic images of the second type using the machine-learning model.
19. The method of item 18, further comprising: training a classifier based on the plurality of synthetic images of the second type.
20. The method of item 19, wherein the microscope is a first microscope, wherein the classifier is a first classifier, further comprising:
obtaining, using a second microscope, a plurality of images of the second type;
training a second classifier based on the plurality of images of the second type;
comparing performance of the first classifier and the second classifier.
21. The method of item 20, wherein the second microscope is a fluorescence microscope.
22. A method for generating enhanced images of biological samples, comprising:
obtaining, using a microscope, an image of a biological sample; and
generating, based on the image, an enhanced image of the biological sample using a machine-learning model, wherein the machine-learning model has been trained by:
obtaining a plurality of training images comprising
a training image of a first type, and
a training image of a second type;
generating, based on the training image of the first type, a plurality of wavelet coefficients using the machine-learning model;
generating, based on the plurality of wavelet coefficients, a synthetic image of the second type;
comparing the synthetic image of the second type with the training image of the second type; and
updating the machine-learning model based on the comparison.
23. The method of item 22, wherein the training image of the first type is a bright-field image of a biological sample.
24. The method of item 22, wherein the training image of the second type is a fluorescence image of the biological sample.
25. The method of any of items 22-24, wherein the machine-learning model comprises a generator and a discriminator.
26. The method of item 25, wherein the machine-learning model comprises a conditional GAN model.
27. The method of any of items 25-26, wherein the generator comprises a plurality of neural networks corresponding to a plurality of frequency groups.
28. The method of item 27, wherein each neural network of the plurality of neural networks is configured to generate wavelet coefficients for a respective frequency group.
29. The method of any of items 27-28, wherein the plurality of neural networks comprises a plurality of U-Net neural networks.
30. The method of any of items 26-29, wherein the discriminator is a PatchGAN neural network.
31. The method of any of items 23-30, further comprising: generating, based on the training image of the first type, an image of a third type.
32. The method of item 31, wherein the image of the third type is a phase shift image.
33. The method of any of items 23-32, further comprising: generating, based on the training image of the first type, an image of a fourth type.
34. The method of item 33, wherein the image of the fourth type comprises segmentation data.
35. The method of any of items 23-34, wherein the training image of the first type is captured using a microscope according to a first illumination scheme.
36. The method of item 35, wherein the first illumination scheme comprises one or more illumination patterns.
37. The method of any of items 35-36, wherein the training image of the first type is part of a bright-field image array.

38. The method of any of items 35-37, wherein the plurality of training images is a first plurality of training images, the method further comprising:
   based on the comparison, identifying a second illumination scheme;
   obtaining a second plurality of training images comprising one or more images of the first type, wherein the one or more images of the first type are obtained based on the second illumination scheme;
   training the machine-learning model based on the second plurality of training images.
39. The method of any of items 35-38, further comprising:
   obtaining, using a microscope, a plurality of images of the first type; and
   generating, based on the obtained plurality of images, a plurality of synthetic images of the second type using the machine-learning model.
40. The method of item 39, further comprising: training a classifier based on the plurality of synthetic images of the second type.
41. The method of item 40, wherein the microscope is a first microscope, wherein the classifier is a first classifier, further comprising:
   obtaining, using a second microscope, a plurality of images of the second type;
   training a second classifier based on the plurality of images of the second type;
   comparing performance of the first classifier and the second classifier.
42. The method of item 41, wherein the second microscope is a fluorescence microscope.
43. A system for training a machine-learning model to generate images of biological samples, comprising:
   a computing system comprising one or more processors, and one or more memories storing a machine-learning model, wherein the computing system is configured to receive a plurality of training images of a first type and one a training image of a second type, and wherein the computing system is configured to:
   generate, based on the training images of the first type, a plurality of wavelet coefficients using the machine-learning model;
   generate, based on the plurality of wavelet coefficients, a synthetic image of the second type;
   compare the synthetic image of the second type with the training image of the second type; and
   update the machine-learning model based on the comparison.
44. The system of item 43, wherein the training image of the first type is a bright-field image of a biological sample.
45. The system of any of items 43-44, wherein the training image of the second type is a fluorescence image of the biological sample.
46. The system of any of items 43-45, wherein the machine-learning model comprises a generator and a discriminator.
47. The system of item 46, wherein the machine-learning model comprises a conditional GAN model.
48. The system of any of items 46-47, wherein the generator comprises a plurality of neural networks corresponding to a plurality of frequency groups.
49. The system of item 48, wherein each neural network of the plurality of neural networks is configured to generate wavelet coefficients for a respective frequency group.
50. The system of any of items 48-49, wherein the plurality of neural networks comprises a plurality of U-Net neural networks.
51. The system of any of items 46-50, wherein the discriminator is a PatchGAN neural network.
52. The system of any of items 43-51, wherein the computing system is further configured to: generate, based on the training image of the first type, an image of a third type.
53. The system of item 52, wherein the image of the third type is a phase shift image.
54. The system of any of items 43-53, wherein the computing system is further configured to: generate, based on the training image of the first type, an image of a fourth type.
55. The system of item 54, wherein the image of the fourth type comprises segmentation data.
56. The system of any of items 43-55, wherein the training image of the first type is captured using a microscope according to a first illumination scheme.
57. The system of item 56, wherein the first illumination scheme comprises one or more illumination patterns.
58. The system of any of items 56-57, wherein the training image of the first type is part of a bright-field image array.
59. The system of any of items 56-58, wherein the plurality of training images is a first plurality of training images, and wherein the computing system is further configured to:
   based on the comparison, identify a second illumination scheme;
   obtain a second plurality of training images comprising one or more images of the first type, wherein the one or more images of the first type are obtained based on the second illumination scheme;
   train the machine-learning model based on the second plurality of training images.
60. The system of any of items 43-59, wherein the computing system is further configured to:
   obtain, using a microscope, a plurality of images of the first type; and
   generate, based on the obtained plurality of images, a plurality of synthetic images of the second type using the machine-learning model.
61. The system of item 59, wherein the computing system is further configured to: train a classifier based on the plurality of synthetic images of the second type.
62. The system of item 61, wherein the microscope is a first microscope, wherein the classifier is a first classifier, wherein the computing system is further configured to:
   obtain, using a second microscope, a plurality of images of the second type;
   train a second classifier based on the plurality of images of the second type;
   compare performance of the first classifier and the second classifier.
63. The system of item 62, wherein the second microscope is a fluorescence microscope.
64. A system for generating enhanced images of biological samples, comprising:
   a computing system comprising one or more processors, and one or more memories storing a machine-learning model, wherein the computing system is configured to receive an image of a biological sample obtained from a microscope and generate, based on the image, an enhanced image of the biological sample using a machine-learning model, wherein the machine-learning model has been trained by:
obtaining a plurality of training images comprising:
a training image of a first type, and
a training image of a second type;
generating, based on the training image of the first type, a plurality of wavelet coefficients using the machine-learning model;
generating, based on the plurality of wavelet coefficients, a synthetic image of the second type;
comparing the synthetic image of the second type with the training image of the second type; and
updating the machine-learning model based on the comparison.

65. The system of item 64, wherein the training image of the first type is a bright-field image of a biological sample.

66. The system of item 64, wherein the training image of the second type is a fluorescence image of the biological sample.

67. The system of any of items 64-66, wherein the machine-learning model comprises a generator and a discriminator.

68. The system of item 67, wherein the machine-learning model comprises a conditional GAN model.

69. The system of any of items 67-68, wherein the generator comprises a plurality of neural networks corresponding to a plurality of frequency groups.

70. The system of item 69, wherein each neural network of the plurality of neural networks is configured to generate wavelet coefficients for a respective frequency group.

71. The system of any of items 69-70, wherein the plurality of neural networks comprises a plurality of U-Net neural networks.

72. The system of any of items 67-71, wherein the discriminator is a PatchGAN neural network.

73. The system of any of items 64-72, wherein the machine learning model is further trained by generating, based on the training image of the first type, an image of a third type.

74. The system of item 73, wherein the image of the third type is a phase shift image.

75. The system of any of items 64-74, wherein the machine-learning model has been trained by: generating, based on the training image of the first type, an image of a fourth type.

76. The system of item 75, wherein the image of the fourth type comprises segmentation data.

77. The system of any of items 64-76, wherein the training image of the first type is captured using a microscope according to a first illumination scheme.

78. The system of item 77, wherein the first illumination scheme comprises one or more illumination patterns.

79. The system of any of items 77-78, wherein the training image of the first type is part of a bright-field image array.

80. The system of any of items 77-79, wherein the plurality of training images is a first plurality of training images, wherein the machine-learning model has been trained by:
based on the comparison, identifying a second illumination scheme;
obtaining a second plurality of training images comprising one or more images of the first type, wherein the one or more images of the first type are obtained based on the second illumination scheme;
training the machine-learning model based on the second plurality of training images.

81. The system of any of items 77-80, wherein the machine-learning model has been trained by:
obtaining, using a microscope, a plurality of images of the first type; and
generating, based on the obtained plurality of images, a plurality of synthetic images of the second type using the machine-learning model.

82. The system of item 81, wherein the machine-learning model has been trained by: training a classifier based on the plurality of synthetic images of the second type.

83. The system of item 82, wherein the microscope is a first microscope, wherein the classifier is a first classifier, wherein the machine-learning model has been trained by:
obtaining, using a second microscope, a plurality of images of the second type;
training a second classifier based on the plurality of images of the second type;
comparing performance of the first classifier and the second classifier.

84. The system of item 83, wherein the second microscope is a fluorescence microscope.

85. A method of processing images of a biological sample to obtain one or more output images, comprising:
obtaining a plurality of images of the biological sample using a plurality of configurations of a SLM of an optical system, wherein the SLM is located in an optical path between the biological sample and an image recording device; and
inputting the plurality of images of the biological sample into a trained machine-learning model to obtain the one or more outputs images.

86. The method of item 85, wherein at least one configuration of the plurality of configurations of the SLM is to generate one or more optical aberrations.

87. The method of item 86, wherein generating one or more optical aberrations comprises a spherical aberration, astigmatism, defocus, distortion, tilt, or any combination thereof 88. The method of any of items 85-86, wherein at least one configuration of the plurality of configurations of the SLM is to enhance one or more features.

89. The method of item 88, wherein the one or more features comprise a cell border, an actin filament, nuclear shape, cytoplasm segmentation, or any combination thereof 90. The method of any of items 85-89, wherein at least one configuration of the plurality of configurations of the SLM is to reduce optical aberrations.

91. The method of any of items 85-90, wherein the plurality of SLM configurations is to obtain images of the biological sample at different depths.

92. The method of any of items 85-91, wherein the machine-learning model is configured to generate, based on an image of a first type, an image of a second type.

93. The method of item 92, wherein the first type of images are bright-field images.

94. The method of item 92, wherein the second type of images are fluorescence images.

95. The method of item 92, wherein the second type of images are enhanced versions of the first type of images.

96. The method of any of items 92-95, wherein the machine-learning model is a GAN model or a self-supervised model.
97. The method of any of items 85-96, wherein the plurality of images are obtained using a plurality of configurations of a light source of the optical system.
98. The method of item 97, wherein the light source is a LED array of the optical system.
99. The method of any of items 85-98, wherein at least one configuration of the plurality of SLM configurations is obtained by:
   training the machine-learning model;
   evaluating the trained machine-learning model; and
   identifying the at least one configuration based on the evaluation.
100. The method of any of items 85-99, wherein the trained machine-learning model is configured to receive an input image and output an enhanced version of the input image.
101. The method of item 100, wherein the enhanced version of the input image comprises one or more enhanced cellular phenotypes.
102. An electronic device for processing images of a biological sample to obtain one or more output images, comprising:
   one or more processors;
   a memory; and
   one or more programs, wherein the one or more programs are stored in the memory and configured to be executed by the one or more processors, the one or more programs including instructions for:
      obtaining a plurality of images of the biological sample using a plurality of configurations of a SLM of an optical system, wherein the SLM is located in an optical path between the biological sample and an image recording device; and
      inputting the plurality of images of the biological sample into a trained machine-learning model to obtain the one or more output images.
103. A non-transitory computer-readable storage medium storing one or more programs for processing images of a biological sample to obtain one or more output images, the one or more programs comprising instructions, which when executed by one or more processors of an electronic device, cause the electronic device to:
   obtain a plurality of images of the biological sample using a plurality of configurations of a SLM of an optical system, wherein the SLM is located in an optical path between the biological sample and an image recording device; and input the plurality of images of the biological sample into a trained machine-learning model to obtain the one or more output images.
104. A method of classifying images of a biological sample, comprising:
   obtaining a plurality of images of the biological sample using a plurality of configurations of an SLM of an optical system, wherein the SLM is located in an optical path between the biological sample and an image recording device; and
   inputting the plurality of images of the biological sample into a trained machine-learning model to obtain one or more classification outputs.
105. The method of item 104, wherein at least one configuration of the plurality of configurations of the SLM is to generate one or more optical aberrations.
106. The method of item 105, wherein generating one or more optical aberrations comprises a spherical aberration, astigmatism, defocus, distortion, tilt, or any combination thereof
107. The method of any of items 104-106, wherein at least one configuration of the plurality of configurations of the SLM is to enhance one or more features.
108. The method of item 107, wherein the one or more features comprise a cell border, an actin filament, nuclear shape, cytoplasm segmentation, or any combination thereof
109. The method of any of items 104-108, wherein at least one configuration of the plurality of configurations of the SLM is to reduce optical aberrations.
110. The method of any of items 104-109, wherein the plurality of SLM configurations is to obtain images of the biological sample at different depths.
111. The method of any of items 104-110, wherein the plurality of images are obtained using a plurality of configurations of a light source of the optical system.
112. The method of item 111, wherein the light source is a LED array of the optical system.
113. The method of any of items 104-112, wherein at least one configuration of the plurality of SLM configurations is obtained by:
   training the machine-learning model;
   evaluating the trained machine-learning model; and
   identifying the at least one configuration based on the evaluation.
114. The method of any of items 104-113, wherein the trained machine-learning model is configured to receive an input image and detect one or more pre-defined objects in the input image.
115. The method of item 114, wherein the pre-defined objects include a diseased tissue.
116. An electronic device for classifying images of a biological sample, comprising:
   one or more processors;
   a memory; and
   one or more programs, wherein the one or more programs are stored in the memory and configured to be executed by the one or more processors, the one or more programs including instructions for:
      obtaining a plurality of images of the biological sample using a plurality of configurations of an SLM of an optical system, wherein the SLM is located in an optical path between the biological sample and an image recording device; and
      inputting the plurality of images of the biological sample into a trained machine-learning model to obtain one or more classification outputs.
117. A non-transitory computer-readable storage medium storing one or more programs for classifying images of a biological sample, the one or more programs comprising instructions, which when executed by one or more processors of an electronic device, cause the electronic device to:
   obtain a plurality of images of the biological sample using a plurality of configurations of an SLM of an optical system, wherein the SLM is located in an optical path between the biological sample and an image recording device; and
   input the plurality of images of the biological sample into a trained machine-learning model to obtain one or more classification outputs.

118. A method for training a machine-learning model, comprising:
   obtaining a plurality of images of a biological sample using a plurality of configurations of an SLM of an optical system, wherein the SLM is located in an optical path between the biological sample and an image recording device; and
   training the machine-learning model using the plurality of images.
119. The method of item 118, wherein at least one configuration of the plurality of configurations of the SLM is to generate one or more optical aberrations.
120. The method of item 119, wherein generating one or more optical aberrations comprises a spherical aberration, astigmatism, defocus, distortion, tilt, or any combination thereof
121. The method of any of items 118-120, wherein at least one configuration of the plurality of configurations of the SLM is to enhance one or more features.
122. The method of item 121, wherein the one or more features comprise a cell border, an actin filament, nuclear shape, cytoplasm segmentation, or any combination thereof
123. The method of any of items 118-122, wherein at least one configuration of the plurality of configurations of the SLM is to reduce optical aberrations.
124. The method of any of items 118-123, wherein at least one configuration of the plurality of configurations of the SLM is to obtain images of the biological sample at different depths.
125. The method of any of items 118-124, wherein the machine-learning model is configured to generate, based on an image of a first type, an image of a second type.
126. The method of item 125, wherein the first type of images are bright-field images.
127. The method of item 125, wherein the second type of images are fluorescence images.
128. The method of any of items 118-127, wherein the machine-learning model is a GAN model or a self-supervised model.
129. The method of any of items 118-128, wherein the machine-learning model is a classification model.
130. The method of any of items 118-129, wherein the plurality of images are obtained using a plurality of configurations of a light source of the optical system.
131. The method of item 130, wherein the light source is a LED array of the optical system.
132. The method of any of items 118-131, wherein training the machine-learning model comprises:
   (a) training the machine-learning model using a first image, wherein the first image is obtained using a first configuration of the SLM of the optical system;
   (b) evaluating the trained machine-learning model;
   (c) based on the evaluation, identifying a second configuration of the SLM; and
   (d) training the machine-learning model using a second image, wherein the second image is obtained using the second configuration of the SLM of the optical system.
133. The method of item 112, wherein the evaluation is based on a loss function of the machine-learning model.
134. The method of any of items 112-113, further comprising: repeating steps (a)-(d) until a threshold is met.
135. The method of item 114, wherein the threshold is indicative of convergence of the training.
136. The method of any of items 118-135, wherein the trained machine-learning model is configured to receive an input image and output an enhanced version of the input image.
137. The method of item 136, wherein the enhanced version of the input image comprises one or more enhanced cellular phenotypes.
138. The method of any of items 118-135, wherein the trained machine-learning model is configured to receive an input image and detect one or more pre-defined objects in the input image.
139. The method of item 138, wherein the pre-defined objects include a diseased tissue.
140. An electronic device for training a machine-learning model, comprising:
   one or more processors;
   a memory; and
   one or more programs, wherein the one or more programs are stored in the memory and configured to be executed by the one or more processors, the one or more programs including instructions for:
      obtaining a plurality of images of a biological sample using a plurality of configurations of an SLM of an optical system, wherein the SLM is located in an optical path between the biological sample and an image recording device; and
      training the machine-learning model using the plurality of images.
141. A non-transitory computer-readable storage medium storing one or more programs for training a machine-learning model, the one or more programs comprising instructions, which when executed by one or more processors of an electronic device, cause the electronic device to:
   obtain a plurality of images of a biological sample using a plurality of configurations of an SLM of an optical system, wherein the SLM is located in an optical path between the biological sample and an image recording device; and train the machine-learning model using the plurality of images.
142. A method of generating enhanced images of biological samples, comprising:
   obtaining, using a microscope, an image of a biological sample illuminated using an illumination pattern of an illumination source, wherein the illumination pattern is determined by:
      training a classification model configured to receive an input image and output a classification result,
      training, using the trained classification model, a machine-learning model having an plurality of weights corresponding to a plurality of illumination settings, and
      identifying the illumination pattern based on the plurality of weights of the trained machine-learning model; and
   generating an enhanced image of the biological sample by inputting the obtained image of the biological sample into the trained machine-learning model.
143. The method of item 142, wherein the obtained image is a bright-field image.
144. The method of any of items 142-143, wherein the enhanced image is a fluorescence image, a phase image, or a combination thereof
145. The method of any of items 142-144, wherein the illumination source comprises an array of illumination emitters.

146. The method of item 145, wherein the illumination source is a LED array.

147. The method of any of items 142-146, wherein the illumination pattern indicates whether each illumination emitter is turned on or off and the intensity of each illumination emitter.

148. The method of any of items 145-147, wherein each illumination setting of the plurality of illumination settings corresponds to a respective illumination emitter of the illumination source; and wherein each weight corresponds to an intensity of the respective illumination emitter.

149. The method of any of items 142-148, wherein the classification model is configured to receive an input phase image or an input fluorescence image and output a classification result indicative of one class out of a plurality of pre-defined classes.

150. The method of item 149, wherein the plurality of pre-defined classes comprises a healthy class and a diseased class.

151. The method of item 150, wherein the machine-learning model is a GAN model comprising an attention layer comprising the plurality of weights, a discriminator, and a generator.

152. The method of item 151, wherein the machine-learning model is a conditional GAN model.

153. The method of any of items 151-152, wherein the generator comprises a plurality of neural networks corresponding to a plurality of frequency groups.

154. The method of item 153, wherein each neural network of the plurality of neural networks is configured to generate wavelet coefficients for a respective frequency group.

155. The method of any of items 153-154, wherein the plurality of neural networks comprises a plurality of U-Net neural networks.

156. The method of any of items 151-155, wherein the discriminator is a PatchGAN neural network.

157. The method of any of items 151-156, wherein training, using the trained classification model, the machine-learning model comprises:
applying the plurality of weights to a plurality of bright-field training images;
aggregating the plurality of weighted bright-field training images into an aggregated bright-field image;
inputting the aggregated bright-field training image into the machine-learning model to obtain an enhanced training image and a generator loss;
inputting the enhanced training image into the trained classifier to obtain a classifier loss;
augmenting the generator loss based on the classifier loss; and
updating the plurality of weights based on the augmented generator loss.

158. The method of any of items 142-157, further comprising: classifying the enhanced image using the trained classifier.

159. The method of any of items 142-158, further comprising: displaying the enhanced image.

160. A system for generating enhanced images of biological samples, comprising:
one or more processors;
a memory; and
one or more programs, wherein the one or more programs are stored in the memory and configured to be executed by the one or more processors, the one or more programs including instructions for:
obtaining, using a microscope, an image of a biological sample illuminated using an illumination pattern of an illumination source, wherein the illumination pattern is determined by:
training a classification model configured to receive an input image and output a classification result,
training, using the trained classification model, a machine-learning model having an plurality of weights corresponding to a plurality of illumination settings, and
identifying the illumination pattern based on the plurality of weights of the trained machine-learning model; and
generating an enhanced image of the biological sample by inputting the obtained image of the biological sample into the trained machine-learning model.

161. A non-transitory computer-readable storage medium storing one or more programs for generating enhanced images of biological samples, the one or more programs comprising instructions, which when executed by one or more processors of an electronic device, cause the electronic device to:
obtain, using a microscope, an image of a biological sample illuminated using an illumination pattern of an illumination source, wherein the illumination pattern is determined by:
training a classification model configured to receive an input image and output a classification result,
training, using the trained classification model, a machine-learning model having an plurality of weights corresponding to a plurality of illumination settings, and
identifying the illumination pattern based on the plurality of weights of the trained machine-learning model; and
generate an enhanced image of the biological sample by inputting the obtained image of the biological sample into the trained machine-learning model.

162. A method of evaluating a treatment with respect to a disease of interest, comprising:
receiving a first plurality of images depicting a first set of healthy biological samples not affected by the disease of interest;
receiving a second plurality of images depicting a second set of untreated biological samples affected by the disease of interest;
receiving a third plurality of images depicting a third set of treated biological samples affected by the disease of interest and treated by the treatment;
inputting the first plurality of images into a trained machine-learning model to obtain a first plurality of enhanced images;
inputting the second plurality of images into the trained machine-learning model to obtain a second plurality of enhanced images;
inputting the third plurality of images into the trained machine-learning model to obtain a third plurality of enhanced images;
comparing the first plurality of enhanced images, the second plurality of enhanced images, and the third plurality of enhanced images to evaluate the treatment.

163. The method of item 162, wherein the first plurality of images, the second plurality of images, and the third plurality of images are bright-field images.

164. The method of any of items 162-163, wherein the first plurality of enhanced images, the second plurality of enhanced images, and the third plurality of enhanced images are fluorescence images.
165. The method of any of items 162-163, wherein the first plurality of enhanced images, the second plurality of enhanced images, and the third plurality of enhanced images are phase images.
166. The method of any of items 162-165, wherein comparing the first plurality of enhanced images, the second plurality of enhanced images, and the third plurality of enhanced images to evaluate the treatment comprises: identifying, in each image, a signal associated with a biomarker.
167. The method of item 166, wherein comparing the first plurality of enhanced images, the second plurality of enhanced images, and the third plurality of enhanced images to evaluate the treatment further comprises:
    determining a first distribution based on signals of the biomarker in the first plurality of enhanced images;
    determining a second distribution based on signals of the biomarker in the second plurality of enhanced images; and
    determining a third distribution based on signals of the biomarker in the third plurality of enhanced images.
168. The method of item 167, wherein comparing the first plurality of enhanced images, the second plurality of enhanced images, and the third plurality of enhanced images to evaluate the treatment further comprises:
    comparing the first distribution, the second distribution, and the third distribution to evaluate the treatment.
169. The method of any of items 162-165, wherein comparing the first plurality of enhanced images, the second plurality of enhanced images, and the third plurality of enhanced images to evaluate the treatment comprises: determining, for each image, a score indicative of the statement of the disease of interest.
170. The method of item 169, wherein comparing the first plurality of enhanced images, the second plurality of enhanced images, and the third plurality of enhanced images to evaluate the treatment further comprises:
    determining a first distribution based on scores of the first plurality of enhanced images;
    determining a second distribution based on scores of the second plurality of enhanced images; and
    determining a third distribution based on scores of the third plurality of enhanced images.
171. The method of item 170, wherein comparing the first plurality of enhanced images, the second plurality of enhanced images, and the third plurality of enhanced images to evaluate the treatment further comprises:
    comparing the first distribution, the second distribution, and the third distribution to evaluate the treatment.
172. The method of any of items 162-171, wherein the treatment is a first treatment, the method further comprising:
    receiving a fourth plurality of images depicting a fourth set of treated biological samples affected by the disease of interest and treated by a second treatment;
    inputting the fourth plurality of images into the trained machine-learning model to obtain a fourth plurality of enhanced images;
    comparing the first plurality of enhanced images, the second plurality of enhanced images, the third plurality of enhanced images, and the fourth plurality of enhanced images to compare the first treatment and the second treatment.
173. The method of item 172, further comprising: selecting a treatment out of the first treatment and the second treatment based on the comparison.
174. The method of item 173, further comprising: administering the selected treatment.
175. The method of item 173, further comprising: providing a medical recommendation based on the selected treatment.
176. The method of any of items 162-175, wherein the trained machine-learning model is is a GAN model comprising a discriminator and a generator.
177. The method of item 176, wherein the machine-learning model is a conditional GAN model.
178. The method of any of items 176-177, wherein the generator comprises a plurality of neural networks corresponding to a plurality of frequency groups.
179. The method of item 178, wherein each neural network of the plurality of neural networks is configured to generate wavelet coefficients for a respective frequency group.
180. The method of any of items 176-179, wherein the discriminator is a PatchGAN neural network.
181. A system for evaluating a treatment with respect to a disease of interest, comprising:
    one or more processors;
    a memory; and
    one or more programs, wherein the one or more programs are stored in the memory and configured to be executed by the one or more processors, the one or more programs including instructions for:
    receiving a first plurality of images depicting a first set of healthy biological samples not affected by the disease of interest;
        receiving a second plurality of images depicting a second set of untreated biological samples affected by the disease of interest;
        receiving a third plurality of images depicting a third set of treated biological samples affected by the disease of interest and treated by the treatment;
        inputting the first plurality of images into a trained machine-learning model to obtain a first plurality of enhanced images;
        inputting the second plurality of images into the trained machine-learning model to obtain a second plurality of enhanced images;
        inputting the third plurality of images into the trained machine-learning model to obtain a third plurality of enhanced images;
        comparing the first plurality of enhanced images, the second plurality of enhanced images, and the third plurality of enhanced images to evaluate the treatment.
182. A non-transitory computer-readable storage medium storing one or more programs for evaluating a treatment with respect to a disease of interest, the one or more programs comprising instructions, which when executed by one or more processors of an electronic device, cause the electronic device to:
    receiving a first plurality of images depicting a first set of healthy biological samples not affected by the disease of interest;
    receiving a second plurality of images depicting a second set of untreated biological samples affected by the disease of interest;
    receiving a third plurality of images depicting a third set of treated biological samples affected by the disease of interest and treated by the treatment;

inputting the first plurality of images into a trained machine-learning model to obtain a first plurality of enhanced images;
inputting the second plurality of images into the trained machine-learning model to obtain a second plurality of enhanced images;
inputting the third plurality of images into the trained machine-learning model to obtain a third plurality of enhanced images;
comparing the first plurality of enhanced images, the second plurality of enhanced images, and the third plurality of enhanced images to evaluate the treatment.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

What is claimed is:

1. A method for generating enhanced images of biological samples, comprising:
obtaining, using a microscope, an image of a biological sample; and
generating, based on the image, an enhanced image of the biological sample using a machine-learning model, wherein the machine-learning model has been trained by:
obtaining a plurality of training images comprising
a training image of a first type, and
a training image of a second type;
generating, based on the training image of the first type, a plurality of wavelet coefficients using the machine-learning model;
generating, based on the plurality of wavelet coefficients, a synthetic image of the second type;
comparing the synthetic image of the second type with the training image of the second type; and
updating the machine-learning model based on the comparison.

2. The method of claim 1, wherein the training image of the first type is a bright-field image of a biological sample.

3. The method of claim 2, further comprising: generating, based on the training image of the first type, an image of a third type.

4. The method of claim 3, wherein the image of the third type is a phase shift image.

5. The method of claim 2, further comprising: generating, based on the training image of the first type, an image of a fourth type.

6. The method of claim 5, wherein the image of the fourth type comprises segmentation data.

7. The method of claim 2, wherein the training image of the first type is captured using a microscope according to a first illumination scheme.

8. The method of claim 7, wherein the first illumination scheme comprises one or more illumination patterns.

9. The method of claim 7, wherein the training image of the first type is part of a bright-field image array.

10. The method of claim 7, wherein the plurality of training images is a first plurality of training images, the method further comprising:
based on the comparison, identifying a second illumination scheme;
obtaining a second plurality of training images comprising one or more images of the first type, wherein the one or more images of the first type are obtained based on the second illumination scheme;
training the machine-learning model based on the second plurality of training images.

11. The method of claim 7, further comprising:
obtaining, using a microscope, a plurality of images of the first type; and
generating, based on the obtained plurality of images, a plurality of synthetic images of the second type using the machine-learning model.

12. The method of claim 11, further comprising: training a classifier based on the plurality of synthetic images of the second type.

13. The method of claim 12, wherein the microscope is a first microscope, wherein the classifier is a first classifier, further comprising:
obtaining, using a second microscope, a plurality of images of the second type;
training a second classifier based on the plurality of images of the second type;
comparing performance of the first classifier and the second classifier.

14. The method of claim 13, wherein the second microscope is a fluorescence microscope.

15. The method of claim 1, wherein the training image of the second type is a fluorescence image of the biological sample.

16. The method of claim 1, wherein the machine-learning model comprises a generator and a discriminator.

17. The method of claim 16, wherein the machine-learning model comprises a conditional GAN model.

18. The method of claim 17, wherein the discriminator is a PatchGAN neural network.

19. The method of claim 16, wherein the generator comprises a plurality of neural networks corresponding to a plurality of frequency groups.

20. The method of claim 19, wherein each neural network of the plurality of neural networks is configured to generate wavelet coefficients for a respective frequency group.

21. The method of claim 19, wherein the plurality of neural networks comprises a plurality of U-Net neural networks.

22. The method of claim 1, wherein the image of the biological sample is illuminated using an illumination pattern of an illumination source, wherein the illumination pattern is determined by:
training a classification model configured to receive an input image and output a classification result,
training, using the trained classification model, the machine-learning model having a plurality of weights corresponding to a plurality of illumination settings, and
identifying the illumination pattern based on the plurality of weights of the trained machine-learning model.

23. The method of claim 22, wherein the illumination source comprises an array of illumination emitters.

24. The method of claim 23, wherein the illumination source is a LED array.

25. The method of claim 23, wherein each illumination setting of the plurality of illumination settings corresponds to a respective illumination emitter of the illumination source; and wherein each weight corresponds to an intensity of the respective illumination emitter.

26. The method of claim 22, wherein the illumination pattern indicates whether each illumination emitter is turned on or off and the intensity of each illumination emitter.

27. The method of claim 22, wherein the classification model is configured to receive an input phase image or an input fluorescence image and output a classification result indicative of one class out of a plurality of pre-defined classes.

28. A method for training a machine-learning model to generate images of biological samples, comprising:
    obtaining a plurality of training images comprising:
        a microscopic training image of a first type, and
        a microscopic training image of a second type;
    generating, based on the training microscopic image of the first type, a plurality of wavelet coefficients using the machine-learning model;
    generating, based on the plurality of wavelet coefficients, a synthetic image of the second type;
    comparing the synthetic image of the second type with the microscopic training image of the second type; and
    updating the machine-learning model based on the comparison.

\* \* \* \* \*